(12) United States Patent
Gardelli et al.

(10) Patent No.: US 7,091,209 B2
(45) Date of Patent: Aug. 15, 2006

(54) DIHYDROXYPYRIDMIDINE CARBOXYLIC ACIDS AS VIRAL POLYMERASE INHIBITORS

(75) Inventors: Cristina Gardelli, Rome (IT); Claudio Giuliano, Rome (IT); Steven Harper, Rome (IT); Uwe Koch, Rome (IT); Frank Narjes, Rome (IT); Jesus Maria Ontoria Ontoria, Rome (IT); Marco Poma, Rome (IT); Simona Ponzi, Rome (IT); Ian Stansfield, Rome (IT); Vincenzo Summa, Rome (IT)

(73) Assignee: Merck & Co., Inc., Rahway, NJ (US)

( * ) Notice: Subject to any disclaimer, the term of this patent is extended or adjusted under 35 U.S.C. 154(b) by 334 days.

(21) Appl. No.: 10/333,431

(22) PCT Filed: Jul. 11, 2001

(86) PCT No.: PCT/EP01/07955

§ 371 (c)(1),
(2), (4) Date: Jul. 9, 2003

(87) PCT Pub. No.: WO02/06246

PCT Pub. Date: Jan. 24, 2002

(65) Prior Publication Data
US 2004/0106627 A1 Jun. 3, 2004

(30) Foreign Application Priority Data
Jul. 19, 2000 (GB) .................................. 0017676

(51) Int. Cl.
C07D 239/557 (2006.01)
C07D 409/04 (2006.01)
C07D 409/12 (2006.01)
C07D 417/14 (2006.01)
C07D 401/12 (2006.01)

(52) U.S. Cl. .................. 514/262.1; 544/263; 544/319; 544/237; 544/123; 514/274; 540/523

(58) Field of Classification Search ............ 514/262.1, 514/274; 544/263, 319, 237, 123; 540/523
See application file for complete search history.

(56) References Cited

U.S. PATENT DOCUMENTS

| 4,769,458 A | * | 9/1988 | Arold et al. ................. 544/319 |
| 5,420,129 A | | 5/1995 | Breu et al. |
| 6,436,943 B1 | | 8/2002 | Stoltefuss et al. |

FOREIGN PATENT DOCUMENTS

| WO | WO 92/05159 A1 | 4/1992 |
| WO | 19817265 A1 | 4/1998 |
| WO | WO 00/13708 A1 | 3/2000 |

OTHER PUBLICATIONS

Roberts et al. "Basic principles of Organic Chemistry" (Benjamin, INC 1964) p. 531.*
Methyl 2-(4-chlorophenyl)-5,6-dihydroxyprimidine-4-carboxylate, 1999 Maybridge plc catalog.*
T. P. Culbertson, "Synthesis of 5,6-Dihydroxy-2-phenyl-4-pyrimidinecarbxylic Acid, Methyl Ester, a Corrected Structure," J. Heterocyclic Chem., 1979, vol. 16, pp. 1423-1424.
A. A. Santilli et al., "Synthesis of 1,2,4-Oxadiazines and Their Rearrangement to Pyrimidines", J. Heterocyclic Chem., 1979, vol. 16, pp. 213-216.
Translation of Claims of WO 92/05159.

* cited by examiner

*Primary Examiner*—Mark L. Berch
(74) *Attorney, Agent, or Firm*—K. R. Walton; M. Winokur

(57) ABSTRACT

A class of 2-aryl-4,5-dihydroxy-6-carboxypyrimidines of formula (I): wherein Ar is an optionally substituted aryl or heterocyclicgroup; as well as compounds of formula (I) which are derivatized at one or more of the 4-hydroxy, 5-hydroxy or 6-carboxy groups; and tautomers thereof, and pharmaceutically acceptable salts or esters thereof; and inhibitors of viral polymerases, especially the hepatitis C virus (HCV) polymerase enzyme

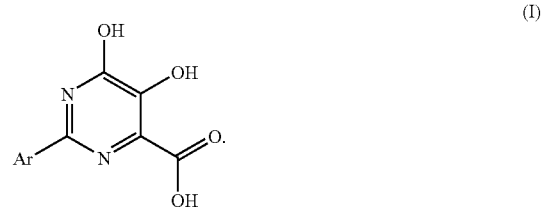

(I)

16 Claims, No Drawings

DIHYDROXYPYRIDMIDINE CARBOXYLIC ACIDS AS VIRAL POLYMERASE INHIBITORS

This application is the National Stage of International Application No. PCT/EP01/07955, filed on Jul. 11, 2001, which claims the benefit of United Kingdom Application No. 001767.8, filed Jul. 19, 2000.

This invention relates to compounds which can act as inhibitors of viral polymerases, especially the hepatitis C virus (HCV) polymerase, to uses of such compounds and to their preparation.

The hepatitis C virus (HCV) is the major causative agent of parenterally-transmitted and sporadic non-A, non-B hepatitis (NANB-H). Some 1% of the human population of the planet is believed to be affected. Infection by the virus can result in chronic hepatitis and cirrhosis of the liver, and may lead to hepatocellular carcinoma. Currently no vaccine nor established therapy exists, although partial success has been achieved in a minority of cases by treatment with recombinant interferon-a, either alone or in combination with ribavirin. There is therefore a pressing need for new and broadly-effective therapeutics.

Several virally-encoded enzymes are putative targets for therapeutic intervention, including a metalloprotease (NS2-3), a serine protease (NS3), a helicase (NS3), and an RNA-dependent RNA polymerase (NS5B). Of these, the polymerase plays an essential role in replication of the virus and is therefore an important target in the fight against hepatitis C.

It has now been found that certain 2-aryl-4,5-dihydroxy-6-carboxypyrimidines act as inhibitors of hepatitis C virus (HCV) polymerase enzyme.

According to a first aspect of the present invention there is provided a 2-aryl-4,5-dihydroxy-6-carboxypyrimidine of formula (I) below, as well as pharmaceutically acceptable salts and esters thereof:

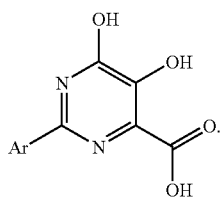

(I)

in which Ar is an optionally substituted aryl group.

It will be appreciated that the compound of formula (I) as depicted above may exist in equilibrium with its other tautomeric forms, including in particular the structure of formula (IA):

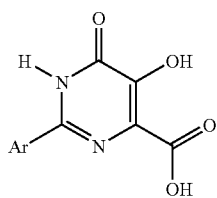

(IA)

wherein Ar is as defined above. It is to be understood that all tautomeric forms of the compounds of formula (I), as well as all possible mixtures thereof in any proportion, are included within the scope of the present invention.

In a second aspect, the present invention provides a compound of formula (I), or a tautomer thereof, or a pharmaceutically acceptable salt or ester thereof, for use in therapy, especially for pharmaceutical use in humans.

Before discussing preferred embodiments of the first and second aspects of the invention it is helpful to define certain terms used throughout the specification.

By "lower alkyl" and "lower alkoxy" are intended groups having from 1 to 10, preferably 1 to 6, most preferably 1 to 4, carbon atoms. "Lower alkenyl" and "lower alkynyl" groups have from 2 to 10, preferably 2 to 6, carbon atoms.

Typical examples of lower alkyl groups include methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical examples of lower alkenyl groups include vinyl, allyl and dimethylallyl groups.

Typical examples of lower alkynyl groups include ethynyl and propargyl groups.

Cycloalkyl and cycloalkenyl groups contain from 3 to 8 carbon atoms, preferably 5 to 7. Heterocycloalkyl and heterocycloalkenyl groups are 3 to 8 membered rings which contain one or more heteroatoms selected from O, N and S.

Typical cycloalkyl groups include cyclopropyl, cyclobutyl, cyclopentyl and cyclohexyl.

Suitable heterocycloalkyl groups include azetidinyl, pyrrolidinyl, piperidinyl, piperazinyl, morpholinyl and thiomorpholinyl groups.

The term "aryr" as used herein is intended to encompass heteroaromatic as well as carbocyclic groups and implies an aromatic (or heteroaromatic) ring optionally fused, e.g. benzofused, with one to three cycloalkyl, aromatic, heterocyclic or heteroaromatic rings. Preferred groups containing a carbocyclic aromatic radical have from 6 to 14, more preferably 6 to 10, carbon atoms prior to any optional substitution. Examples of such groups include phenyl and naphthyl. Heteroaryl groups include a 3 to 7 membered heterocyclic aromatic ring consisting of one or more carbon atoms and from one to four heteroatoms selected from nitrogen, oxygen and sulphur. Aryl groups, in general, and prior to any optional substitution, contain from 1 to 14 carbon atoms, preferably 3 to 10 carbon atoms.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

Aralkyl and aralkoxy groups generally contain from 2 to 20, preferably 4 to 15, carbon atoms.

Typical aralkyl groups include benzyl, phenylethyl, phenylpropyl, naphthylmethyl, furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl. Derived expressions such as "aralkoxy" are to be construed accordingly.

Where a compound or group such as the aryl group, Ar, is described as "optionally substituted" one or more substituents may be present. Optional substituents are not particularly limited and may, for instance, be selected from lower alkyl or alkenyl, cycloalkyl, cycloalkenyl, heterocycloalkyl, heterocycloalkenyl, aryl, aralkyl, lower alkoxy, aryloxy or aralkoxy, amino, nitro, halo, hydroxy, carboxy, formyl, cyano and trihalomethyl groups. Furthermore, optional substituents may be attached to the compounds or groups which they substitute in a variety of ways, either directly or through a connecting group of which the following are examples: amine, amide, ester, ether, thioether, sulphonamide, sulphamide, sulphoxide, urea, thiourea and urethane. As appropriate an optional substituent may itself be substituted by another substituent, the latter being connected directly to the former or through a connecting group such as those exemplified above.

In preferred embodiments of the first and second aspects of the invention the group "Ar" may be selected from the following, all of which may, optionally, be substituted: phenyl, thienyl, oxazolyl, thiazolyl, furyl, isoquinolinyl, indolyl, isoxazolyl, pyrazolopyrimidinyl and pyrazinyl groups. These groups may be joined to the 2-position of the pyrimidine at any available position of the aryl ring. However, connection at certain positions may be preferred and this is considered in some more detail below.

Preferred optional substituents on the aryl group may be selected from a wide variety of groups. For instance, they may be simple, relatively small groups such as halogen (especially chlorine and bromine), hydroxy, —$NO_2$, —$NH_2$, —$CO_2H$, lower alkyl (especially methyl), lower alkenyl or alkynyl, —CN, or lower alkoxy (especially methoxy). As appropriate any of these substituents may be substituted by one or more of the others. However, in general at least one substituent is a group of formula (IV):

$$—X—R^3 \quad\quad\quad (IV)$$

where $R^3$ is a generally hydrophobic moiety containing one or more, but generally at least 3, preferably 4 to 20, particularly 4 to 14, carbon atoms. Preferably, R includes one or more of the following groups, any of which may, optionally, be substituted: aryl, aralkyl, cycloalkyl, lower alkyl (especially branched lower alkyl), heterocycloalkyl, lower alkenyl, cycloalkenyl and heterocycloalkenyl. The group X is preferably selected from —NH—$SO_2$—, —NH—$SO_2$—NH—, —$CH_2$—$SO_2$—, —$SO_2$—NH—, —NH—CO—NH—, —NH—CS—NH—, —NH—CO—O—, —NH—CO—, —CO—NH—, —NH—CO—NH—$SO_2$—, —NH—CO—NH—CO—, —O—, —S—, —NH—, —$CH_2$—, —$CH_2$O— and —$CH_2$S—.

The hydrogen atom of any NH group may, optionally, be replaced by a lower alkyl group.

One preferred class of compounds may be represented by formula (II) below:

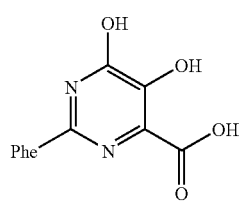

(II)

where Phe is an optionally substituted phenyl group. For instance, examples of compounds within this class are those of formula (III):

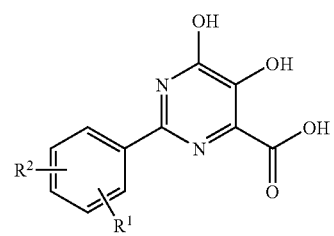

(III)

where each of $R^1$ and $R^2$ may independently be selected from H or a substituent group. Preferably, one of $R^1$ and $R^2$ is hydrogen, while the other is a substituent. Where a substituent is present it may be at any of the 2-, 3- or 4-positions—i.e. ortho, meta or para to the pyrimidine group. However, where a single substituent is present, substitution at the ortho or meta positions is preferred.

The substituents $R^1$ and $R^2$ may be selected from a wide variety of groups. For instance, they may be simple, relatively small groups such as halogen (especially chlorine and bromine), hydroxy, —$NO_2$, —$NH_2$, —$CO_2H$, lower alkyl (especially methyl), lower alkenyl or alkynyl, —CN, or lower alkoxy (especially methoxy). As appropriate any of these substituents may be substituted by one or more of the others.

Although some such compounds are of high activity, it is generally preferable that substituent $R^1$ and/or $R^2$ include a relatively hydrophobic group $R^3$ which is bonded to the phenyl group through a linkage X. In this case the substituents $R^1$ and/or $R^2$ may be represented by the formula (IV):

$$—X—R^3 \quad\quad\quad (IV)$$

where $R^3$ and X are as defined above.

For instance, examples of preferred classes of compound are those in which a single ortho or meta substituent is present, and that substituent is selected from the following formulae (V), (VI), (VII), (VIII) and (IX):

$$—X—(CH_2)_n—R^4 \quad\quad\quad (V)$$

$$—X—CH{=}CH—R^4 \quad\quad\quad (VI)$$

(VII)

$$—X—(CHR^5)_p—(CH_2)_m—(CHR^5)_q—R^4 \quad\quad\quad (VIII)$$

$$—X—(CH_2)_r\text{-}Z\text{-}R^4 \quad\quad\quad (IX)$$

wherein n is zero or an integer from 1 to 6, and preferably is from zero to 3, especially 0 or 1;

m is zero or an integer from 1 to 6, but preferably is 0 or 1;

each of p and q is independently 0 or 1, but preferably they are not simultaneously 1;

r is an integer from 1 to 6, preferably 1;

R⁴ is an optionally substituted aryl, cycloalkyl, cycloalkenyl, heterocycloalkyl, heterocycloalkenyl or branched lower alkyl group;

each R⁵ is independently a lower alkyl group (especially methyl), a cycloalkyl group, an optionally substituted aryl group (especially phenyl), hydroxy or hydroxy lower alkyl (especially hydroxymethyl), any of which may be optionally etherified, or —NH₂, optionally protonated, alkylated or derivatised as a urethane group; and Z is selected from —O—, —S— and —NH—.

In each of the formulae (IV) to (IX) the linkage X may be any of the X groups specified above.

Among the groups X, the sulfonamide (—NH—SO²—), urea (—NH—CO—NH—), urethane (—NH—CO—O—) and amide (—NH—CO—) groups are most preferred. A particular value of X is —NH—CO—NH—SO₂—.

The group R⁴ is preferably an aryl group, of which optionally substituted phenyl, naphthyl, thienyl, benzothienyl, pyridyl, quinolyl and thiazolyl are particularly preferred examples. Each of these may, optionally, be substituted by another optionally substituted aryl or heteroaryl group of the same or different type.

Examples of compounds of formula (II) can be found in Tables I, II, III and IV. All of the compounds in these Tables have IC₅₀ values below 100 μM when measured in the assay described below. In many cases the IC₅₀ is below 10 μM, and in some cases it is 1 μM or below.

A further preferred class of compounds may be represented by formula (X) below:

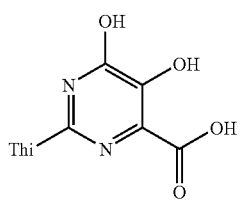

(X)

wherein Thi represents a thienyl group, optionally carrying one or more substituents. Preferred compounds in this class are those in which the thienyl group is unsubstituted, or carries a single substituent R⁶, and may be represented by formula (XI) below:

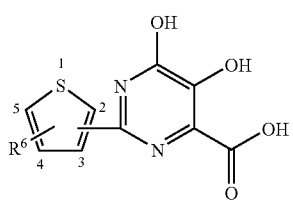

(XI)

The pyrimidine group and the R⁶ substituent may be at any position on the thiophene ring. However, it is preferred that when the pyrimidine is at position 2 on the thiophene ring, then substituent R⁶ is at the 3-position, substitution at the 4- or 5-positions being less preferred. When the pyrimidine group is at the 3-position of the thiophene ring, then R⁶ is preferably at the 2- or 4-position of the thiophene ring, more preferably at the 4-position.

Substituent R⁶ may be selected from a wide variety of groups. For instance, like substituents R¹ and R² discussed above it may be a simple, relatively small group such as halogen (especially chlorine and bromine), hydroxy, —NO₂, —NH₂, —CO₂H, lower alkyl (especially methyl), lower alkenyl or alkynyl, —CN, or lower alkoxy (especially methoxy). As appropriate any of these substituents may be substituted by one or more of the others.

More preferably, however, R⁶ includes a relatively hydrophobic group which is bonded to the thienyl group through a linkage X. In this case, the group R⁶ may be represented by the formula (IV):

—X—R³     (V)

where X and R³ are as defined above.

Preferred X groups are amide, sulphonamide, urea and urethane linkages. A particularly preferred X group is —NH—CO—NH—SO²—. Preferred R³ groups are those shown in formulas (V)–(IX) already discussed above, and which include a group R⁴. Advantageously, R³ is naphthyl.

Preferred R⁴ groups are aromatic groups, especially phenyl, naphthyl, thienyl, pyridyl, benzothienyl, indolyl, benzimidazolyl and oxazolyl groups. When R⁴ comprises fused aromatic rings, the connection to the remainder of the R³ group may be through any ring.

Preferred optional substituents on R⁴, especially in the case where R⁴ is an aryl group, include the following: halogen (e.g. fluorine, chlorine and/or bromine), nitro (—NO₂), lower alkyl (especially methyl), trifluoromethyl and aryl (especially phenyl).

Suitably, n is zero.
Suitably, R⁴ is naphthyl.

Examples of compounds of formula (X) may be found in Tables V–IX. The compounds exemplified all have IC₅₀ values of less than 100 μm as measured in the assay described infra. In fact, virtually all have an IC₅₀ of less than 25 μM, mostly less than 10 μM. Very many of the compounds have submicromolar IC₅₀ values.

Examples of other compounds of formula (I) can be found in Tables X and XI. The compounds of these Tables have IC₅₀ values less than 100 μM, some less than 10 μM.

In another aspect, the invention provides compounds of formula (I) which are derivatised at one or more of the 4-hydroxy, 5-hydroxy or 6-carboxy groups, and tautomers thereof, as well as salts and esters thereof. These compounds also are suitable for pharmaceutical use.

For instance, either or both of the 4- and 5-hydroxy groups may be etherified, e.g. with an optionally substituted alkyl, aryl or aralkyl group. The 6-carboxy group may be esterified with a variety of alcohols, most preferably an optionally substituted lower alkyl alcohol.

Examples of compounds derivatised at the 4-hydroxy, 5-hydroxy or 6-carboxy group are set out in Tables XIIa to XIIc. Although generally less active than the underivatised compounds in the IC₅₀ assay, the exemplified compounds nevertheless all have IC₅₀ values below 50 μM.

According to a further aspect of the invention there is provided the use of a compound of formula (I) above, of a compound of formula (I) which is derivatised at one or more of the 4-hydroxy, 5-hydroxy or 6-carboxy groups, of a tautomer thereof, or of a pharmaceutically acceptable salt or ester thereof, for the manufacture of a medicament for treatment or prevention of infection by hepatitis C virus in a human or animal.

A still further aspect of the invention provides a pharmaceutical composition comprising a compound of formula (I)

above, a compound of formula (I) which is derivatised at one or more of the 4-hydroxy, 5-hydroxy or 6-carboxy groups, a tautomer thereof, or a pharmaceutically acceptable salt or ester thereof, and a pharmaceutically acceptable excipient, diluent or carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

A yet further aspect of the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) above, a compound of formula (I) which is derivatised at one or more of the 4-hydroxy, 5-hydroxy or 6-carboxy groups, a tautomer thereof, or a pharmaceutically acceptable salt or ester thereof "Effective amount" means an amount sufficient to cause a benefit to the subject or at least to cause a change in the subject's condition.

The dosage rate at which the compound, salt or ester is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound, salt or ester may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound selected from a compound of formula (I) above, a compound of formula (I) which is derivatised at one or more of the 4-hydroxy, 5-hydroxy or 6-carboxy groups, a tautomer thereof, or a pharmaceutically acceptable salt or ester thereof, with one or more pharmaceutically acceptable adjuvants, diluents or carriers and/or with one or more other therapeutically or prophylactically active agents.

According to one more aspect of the invention there is provided a method for the production of compounds of formula (I). These may be prepared by hydrolysis of the corresponding methyl or other ester of formula 2:

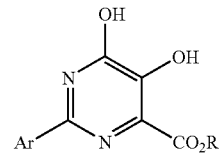

2 where R is a methyl or other lower alkyl group.

The esters of formula 2 may be prepared by cyclization of oximes of formula 3:

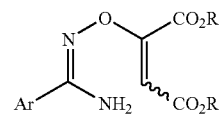

3

Oximes of formula 3 may be prepared by reaction of amide-oximes of formula 4 with diesters of acetylenedicarboxylate:

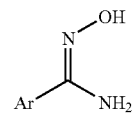

4

Amide-oximes of formula 4 may be prepared by reaction of nitriles of formula 5 with hydroxylamine:

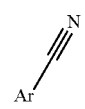

5

Nitriles of formula 5 may be obtained from commercial sources or may be prepared from the corresponding primary amides of formula 6 using established methods known to those skilled in the art:

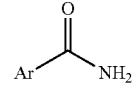

6

Primary amides of formula 6 may be obtained from commercial sources or may be prepared from the corresponding esters or carboxylic acids using established methods known to those skilled in the art.

Compounds of formula (I) which are derivatised at one or more of the 4-hydroxy, 5-hydroxy or 6-carboxy groups may be prepared by analogous methods.

Specific procedures are described in the following Examples:

EXAMPLE 1

2-(4-Chlorophenyl)-4,5-dihydroxyprimidine-6-carboxylate (7)

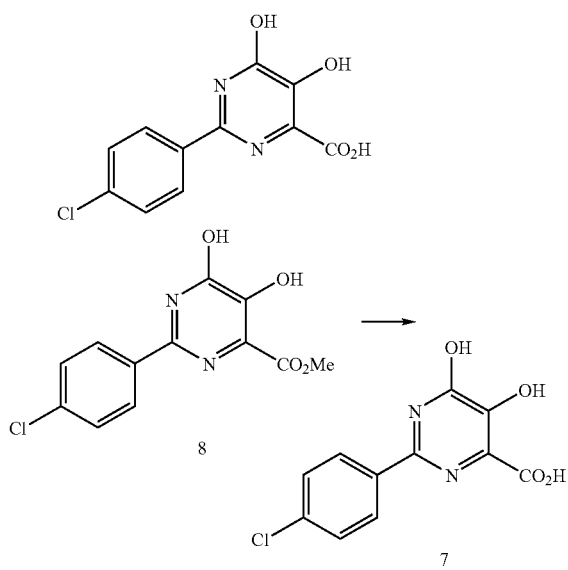

To a suspension of 0.120 g (0.43 mmol) of methyl 2-(4-chlorophenyl)-4,5-dihydroxypyrimidine-6-carboxylate (Aldrich) in 1 ml of MeOH was added 3N NaOH (3 ml) and the mixture was stirred overnight at room temperature. The reaction mixture was acidified by addition of aqueous hydrochloric acid (1N, 5 ml) and the precipitate was filtered off and dried under vacuum to give the title compound (0.11 g, 0.41 mmol, 95% yield). $^1$H NMR (DMSO-d$_6$): δ 8.06 (2H, d, J 8.54), 8.01 (2H, d, J 8.52).

EXAMPLE 2

2-[2-(2-Chlorobenzylureyl)phenyl]-4,5-dihydroxy-6-carboxypyrimidine (9)

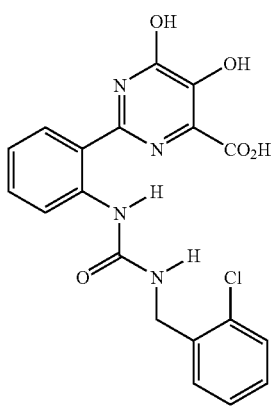

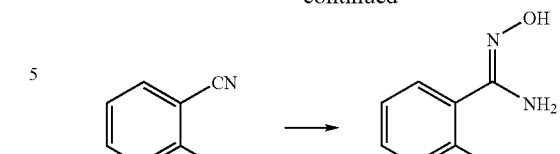

2-Nitrobenzonitrile 10 (10.0 g, 67.51 mmol) was heated at 80° C. in water (120 ml) with sodium carbonate (114.77 mmol, 12.164 g) and hydroxylamine hydrochloride (243 mmol, 16.89 g) for 2 h, sufficient EtOH being added to help dissolution of the reaction mixture. The cooled mixture was filtered to remove solids, the aqueous layer was extracted several times with EtOAc, and the extracts were dried and concentrated under reduced pressure. The resulting yellow solid was purified by flash chromatography, or by recrystallization, to give the title compound (50%). $^1$H NMR (DMSO-d$_6$): δ 9.68 (1H, s), 7.84 (1H, d, J 8), 7.71 (1H, t, J 7.47), 7.64 (1H, d, J 6.3), 7.61 (1H, t, J 8.11), 6.00 (2H, br s). MS m/z 182 (M+1).

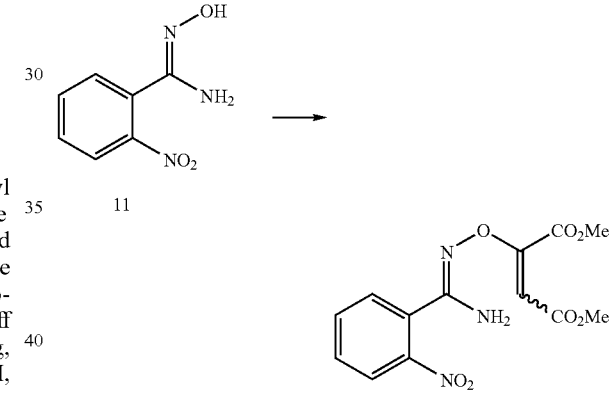

A solution of dimethyl acetylenedicarboxylate (2.60 ml, 21.12 mmol, 1.3 eq) and 11 (2.943 g, 16.246 mmol) in CHCl$_3$ was heated under reflux for 4 h. After concentration of the solvent the crude product was purified by flash chromatography (eluent 1:1 petroleum ether:ethyl acetate) on silica gel to give 12 as a 1:3.7 mixture of the two geometrical isomers (3.15 g, 60%). $^1$H NMR (DMSO-d$_6$): δ 8.04 (1H, d, J 7.83), 7.81 (1H, t, J 7.46), 7.75 (1H, t, J 7.39), 7.70 (1H, d, J 7.40 (64%)), 7.64 (1H, d, J 7.48 (36%)), 7.30 (2H, br s (64%)), 6.92 (2H, br s (36%)), 5.70 (1H, s (36%)), 5.53 (1H, s (36%)), 3.78 (3H, s (64%)), 3.73 (3H, s (36%)), 3.59 (3H, s (64%)), 3.55 (3H, s (36%)). MS m/z 324 (M+1).

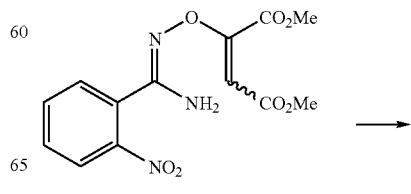

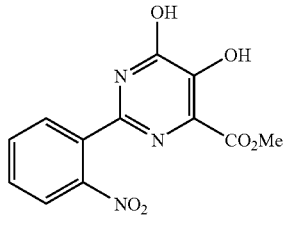

The mixture of adducts 12 (1.28 g, 3.96 mmol) was heated under reflux in ortho-xylenes (15 ml) for 6 h. The hot solution was filtered to give 13 as a yellow solid (0.807 g, 70%). $^1$H NMR (DMSO-d$_6$): δ 13.36 (1H, br s), 10.63 (1H, br s), 8.18 (1H, d, J 7.97), 7.88 (1H, t, J 7.53), 7.80 (1H, d, J 7.79), 7.77 (1H, t, J 7.56), 3.80 (3H, s). MS m/z 292 (M+1).

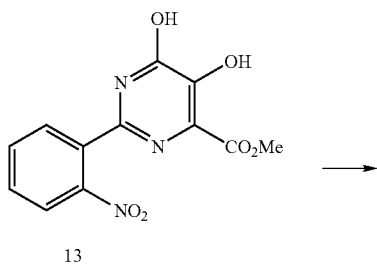

The nitro compound 13 (4.6 g, 15.79 mmol) was dissolved in 450 ml of methanol. Palladium-on-carbon (10% by weight, 200 mg) was added and the mixture was stirred under a hydrogen atmosphere for 2 h. After two hours the reaction was complete (as indicated by reverse-phase tlc) and a green solid had precipitated. Dilute hydrochloric acid (1N) was added dropwise until the precipitate had dissolved. The catalyst was removed by filtration, the filtrate was concentrated in vacuo, and the resulting solid washed with diethyl ether to give 14 (4.5 g, 96%). $^1$H NMR (DMSO-d$_6$): δ 3.85 (3H, s), 6.77 (1H, bt), 6.94 (1H, d, J 8), 7.24 (1H, t, J 7.4), 7.71 (1H, d, J 8). MS m/z 262 (M+1).

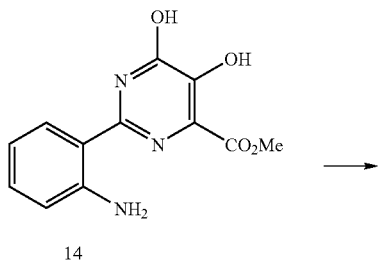

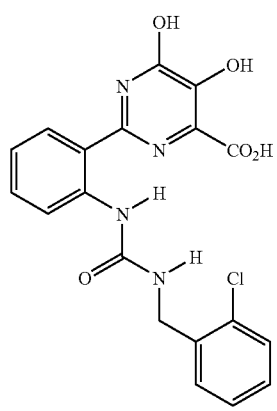

The amino-pyrimidine 14 (95 mg, 0.319 mmol) was dissolved in 4 ml of pyridine and 2-chlorobenzyl isocyanate (0.6 ml, 0.419 mmol), dissolved in 2 ml of CHCl$_3$, was added dropwise. The mixture was stirred at room temperature overnight. The solution was concentrated in vacuo and the resulting solid washed with HCl (1N), MeOH and diethyl ether to give 75 mg (53%) of ester urea which was used without further purification. $^1$H NMR (DMSO-d$_6$): δ 3.80 (3H, s), 4.36 (2H, d, J 5.8), 6.99–7.04 (2H, m), 7.28–7.44 (5H, m), 7.64 (1H, d, J 7.8), 8.23 (1H, d, J 8.10), 10.30 (1H, s), 10.60 (1H, br s), 13.00 (1H, br s). MS m/z 429 (M+1).

To the ester urea was added a 0.5 M solution of NaOH (2 ml) and the resulting mixture was heated under reflux for 30 min. To the cooled solution, HCl (1N) was added dropwise, and a solid precipitate formed. The solid was isolated by filtration, then washed with methanol and diethyl ether to give 31 mg (43%) of the title compound. $^1$H NMR (DMSO-d$_6$): δ 4.35 (2H, d, J 5.8), 6.93 (1H, bt), 7.00 (1H, t, J 7.4), 7.27–7.43 (5H, m), 7.68 (1H, d, J 7.8), 8.22 (1H, d, J 8.2), 10.90 (1H, s), 12.90 (1H, s). MS m/z 415 (M+1).

EXAMPLE 3

2-[3-(Diphenylmethylureyl)phenyl]-4,5-dihydroxy-6-carboxypyrimidine (15)

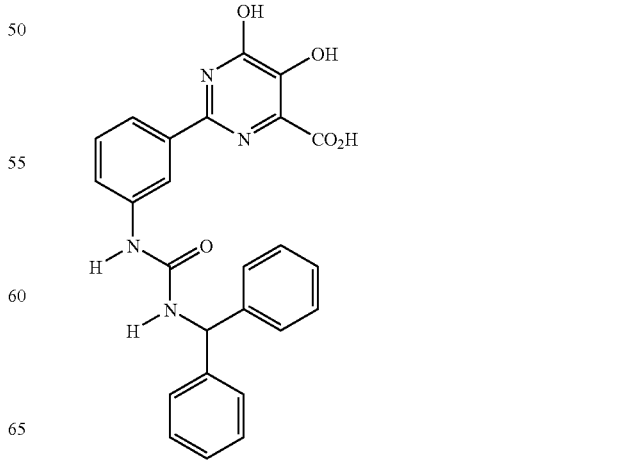

-continued

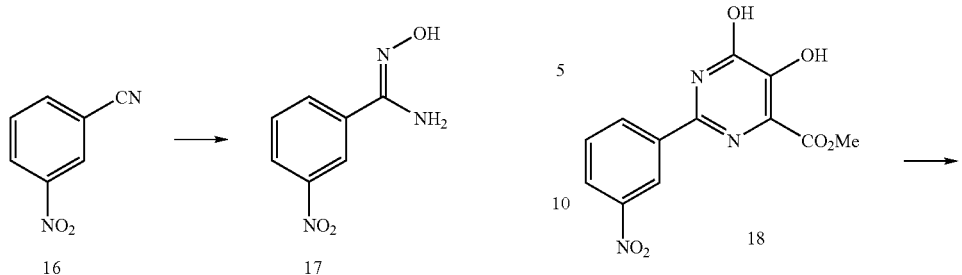

A mixture of 3-nitrobenzonitrile 16 (20 g, 135 mmol) and hydroxylamine hydrochloride (46.9 μg, 675 mmol) in a water/ethanol mixture (600 ml, 5:1) was heated to 60° C. under vigorous stirring. Sodium carbonate (35.8 g, 337.5 mmol) was added portionwise and the temperature was increased to 100° C. The mixture was stirred at 100° C. for 1.5 h. When cooled to room temperature, a solid precipitated which was isolated by filtration to give amidoxime 17 (24 g) as yellow crystals (98%). $^1$H NMR (DMSO-$d_6$): δ 9.94 (1H, s), 8.50 (1H, s), 8.35 (1H, d, J 8), 8.15 (1H, d, J 8), 7.67 (1H, t, J 8), 6.07 (3H, s). MS m/z 182 (M+1).

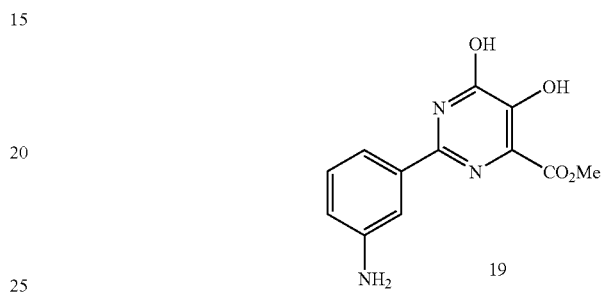

A mixture of amidoxime 17 (22 g, 121.5 mmol) and dimethyl acetylenedicarboxylate (16.4 ml, 133.6 mmol) in a chloroform/methanol mixture (200 ml, 3:1) was refluxed for 3 h which gave a brown solution. The solution was concentrated in vacuo and the resulting oil was dissolved in xylene (150 ml), heated under reflux for 4 h at which point there was precipitation of a solid. The mixture was cooled to room temperature and the solid was isolated by filtration and dried in vacuo to give a brown solid (31 g) that was recrystallized from hot acetic acid (150 ml) to give 18 (28 g, 72%). $^1$H NMR (DMSO-$d_6$): δ 13.43 (1H, br s), 10.71 (1H, br s), 8.86 (1H, s), 8.44 (1H, d, J 8), 8.36 (1H, d, J 8), 7.80 (1H, t, J 8), 3.87 (3H, s). MS m/z 292 (M+1).

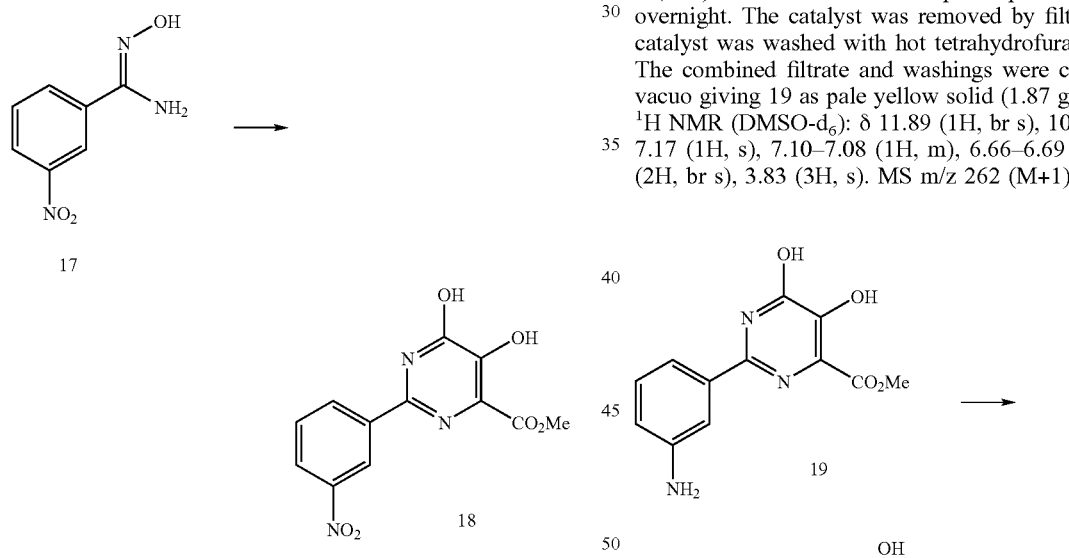

A mixture of compound 18 (2.1 g) and 10% palladium-on-carbon in a mixture of methanol and ethyl acetate (250 ml, 4:1) was stirred under atmospheric pressure of hydrogen overnight. The catalyst was removed by filtration and the catalyst was washed with hot tetrahydrofuran (4×100 ml). The combined filtrate and washings were concentrated in vacuo giving 19 as pale yellow solid (1.87 g, quantitative). $^1$H NMR (DMSO-$d_6$): δ 11.89 (1H, br s), 10.45 (1H, br s), 7.17 (1H, s), 7.10–7.08 (1H, m), 6.66–6.69 (1H, m), 5.32 (2H, br s), 3.83 (3H, s). MS m/z 262 (M+1).

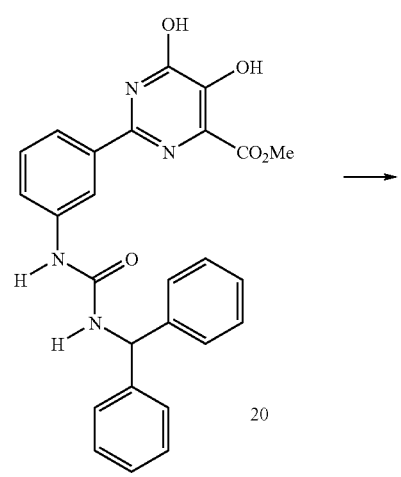

-continued

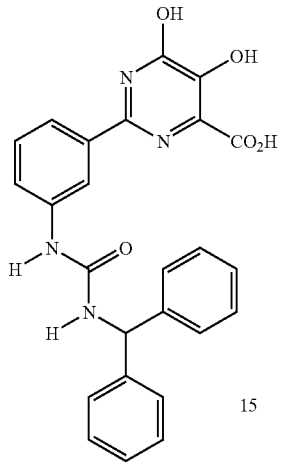

15

Diphenylmethyl isocyanate (1.2 eq) was added neat to a 0.1N solution of pyrimidine 19 (100 mg) in dry pyridine stirring at room temperature overnight in a 15 ml centrifuge tube. Solvent was removed in vacuo using a Speedvac and the resulting solid triturated with 1N hydrochloric acid (3×5 ml), methanol (3×5 ml), diethyl ether (3×5 ml), and solid separated by centrifugation (5 min at 4000 rpm) and dried under vacuum. The residue (ester 20) was suspended in 2.5 eq of 0.5N sodium hydroxide and stirred at 65° C. for 20 min. The pH was adjusted to 3.5 with 1N hydrochloric acid which precipitated a solid. The solid was separated by centrifugation and the residue triturated with water (3×5 ml), methanol (3×5 ml) and diethyl ether (3×5 ml) using centrifuge each time to separate the solid. Removal of the remaining solvent under high vacuum gave desired free acid 15 as a white solid.

$^1$H NMR (DMSO-$d_6$) of 20: δ 13.05 (1H, br s), 8.65 (1H, s), 7.92 (1H, s), 7.59 (1H, d, J 8), 7.52 (1H, d, J 8), 7.37–7.16 (12H, m), 5.91 (1H, d, J 8), 3.79 (3H, s). MS m/z 471 (M+1).

$^1$H NMR (DMSO-$d_6$) of 15: δ (1H, br s), 8.67 (1H, s), 7.93 (1H, s), 7.59 (1H, d, J 8), 7.52 (1H, d, J 8), 7.37–7.16 (12H, m), 5.96 (1H, d, J 8). MS m/z 457 (M+1).

EXAMPLE 4

2-[2-(2,4,6-Trichlorophenylsulfonylamino)phenyl]-4,5-dihydroxy-6-carboxypyrimidine (21)

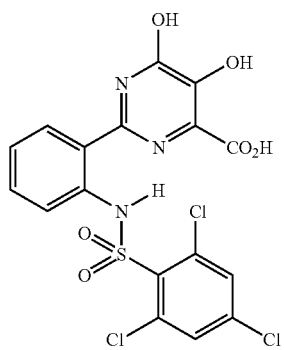

21

-continued

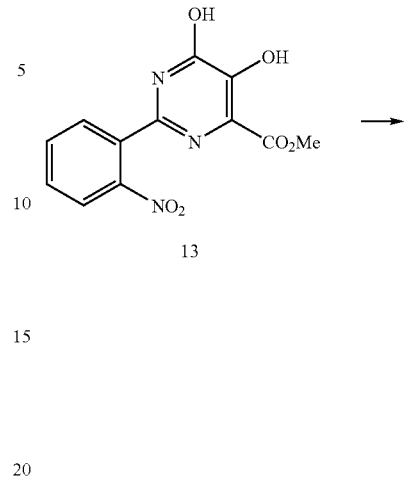

Cesium fluoride (12.1 g, 79.7 mmol) was added to methyl 2-(2-nitrophenyl)-4,5-dihydroxy-6-carboxylate (13) (4.6 g, 15.8 mmol) in N,N-dimethylformamide (120 ml) at room temperature under nitrogen and the resultant suspension stirred vigorously for 20 min. Dibromomethane (1.2 ml, 17.1 mmol) was introduced and the reaction immersed in a pre-heated oil bath at 120° C. After 30 min, a further aliquot of dibromomethane (1.2 ml, 17.1 mmol) was added and heating continued for another 30 min. Additional dibromomethane (0.6 ml, 8.6 mmol) was introduced and heating continued for a further 20 min before the reaction was allowed to cool to room temperature and partitioned between ethyl acetate and water. The aqueous phase was extracted with ethyl acetate and the combined organics washed with 1N aqueous hydrochloric acid, water and then brine. The organics were dried over anhydrous sodium sulfate, filtered and concentrated in vacuo to leave a brown foam. Flash chromatography on silica gel (using 40% ethyl acetate/petroleum ether as eluent) gave the cyclic methyleneacetal (22) as an off-white powder (2.92 g, 61%): $R_f$ (40% ethyl acetate/petroleum ether)=0.25; $^1$H NMR (DMSO-$d_6$; 400 MHz): δ 7.94 (1H, dd, J 7.7, 1.2, (O$_2$N)CCH or (pyrimidine)CCH), 7.93 (1H, dd, J 7.7, 1.5, (O$_2$N)CCH or (pyrimidine)CCH), 7.80 (1H, td, J 7.7, 1.2, (pyrimidine)CC(H)CH or (O$_2$N)CC(H)CH), 7.71 (1H, td, J 7.7, 1.5, pyrimidine)CC(H)CH or (O$_2$N)CC(H)CH), 6.40 (2H, s, OCH$_2$O), 3.88 (3H, s, CO$_2$Me); $^{13}$C NMR (DMSO-$d_6$; 75.5 MHz): δ 167.8, 162.0, 153.4, 149.1, 140.5, 132.5, 130.9, 130.8, 130.7, 129.1, 124.0, 102.7, 52.5; m/z (ES+) 326 (55%, [M+Na]$^+$), 304 (100%, [M+H]$^+$), 272 (20%), 243 (10%), 198 (15%), 186 (15%), 134 (25%).

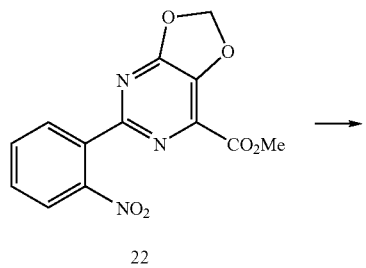

22

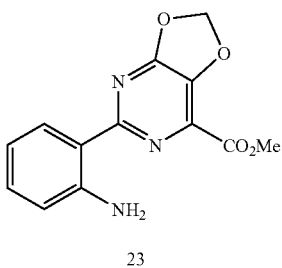

23

A slurry of palladium on carbon (300 mg, 10% Pd/C) in ethyl acetate (20 ml) was added under nitrogen to the 2-nitrophenylpyrimidine (22) (3.5 g, 11.6 mmol) in ethyl acetate (330 ml). The reaction was stirred vigorously under a hydrogen atmosphere overnight (14 h). The catalyst was removed by filtration on a glass fibre filter, washing thoroughly with warm ethyl acetate and methanol. The resultant yellow solution was concentrated in vacuo to afford the aniline (23) as a yellow solid (3 g, 95%): $R_f$ (40% ethyl acetate/petroleum ether)=0.38; $^1$H NMR (DMSO-$d_6$; 400 MHz): δ 8.11 (1H, dd, J 8.1, 1.6, (pyrimidine)CC$\underline{H}$), 7.29 (2H, br s, N$\underline{H}_2$), 7.12 (1H, td, J 7.6, 1.6, (H$_2$N)CC(H)C$\underline{H}$), 6.76 (1H, d, J 8.1, (H$_2$N)CC$\underline{H}$), 6.56 (1H, t, J 7.6, (pyrimidine)CC(H)C$\underline{H}$), 6.32 (2H, s, OC$\underline{H}_2$O), 3.91 (3H, s, CO$_2$M$\underline{e}$); $^{13}$C NMR (DMSO-$d_6$; 75.5 MHz): δ 167.4, 162.7, 157.3, 149.3, 138.3, 131.4, 129.6, 127.3, 116.8, 115.8, 114.9, 101.9, 52.8; m/z (ES+) 296 (10%, [M+Na]$^+$), 274 (100%, [M+H]$^+$), 214 (40%), 186 (30%), 158 (40%), 131 (50%), 118 (65%).

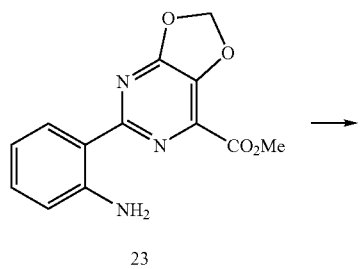

23

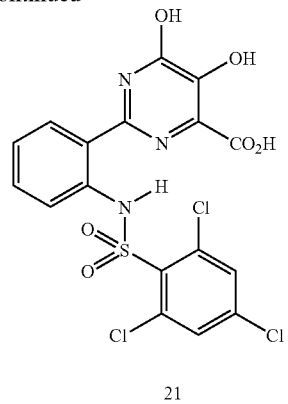

21

Triethylamine (80 μl, 0.574 mmol) was added to the aniline (23) (50 mg, 0.183 mmol) and 2,4,6-trichlorobenzenesulfonyl chloride (Maybridge) (103 mg, 0.368 mmol) in dry acetonitrile (4 ml). The reaction was agitated on an orbital shaker at room temperature overnight followed by removal of volatiles in vacuo in a SpeedVac to afford a brown solid. The solid was suspended in a mixture of 1,4-dioxane (2 ml) and 2N aqueous sodium hydroxide (1 ml, 2 mmol). The reaction was heated, with stirring, at 70° C. for 2 h, then acidified with 4N aqueous hydrochloric acid (1 ml, 4 mmol) and stirred at room temperature for 30 min. The reaction was concentrated in vacuo in a SpeedVac to leave a tan coloured gum. Iterative washing, centrifugation and decanting of the supernatants using first water (3 washings), and then diethyl ether (2 washings), followed by lyophilization (acetonitrile/water) afforded the title compound (21) in crude form as an off-white powder (45 mg, 50%). Purification by reverse phase HPLC (Merck Hibar 250-25, LiChrosorb RP-18 (7 μm) column, using acetonitrile and water (both containing 0.1% trifluoroacetic acid) as eluent gave the title compound (21) as a white powder following lyophilization (21 mg, 23%). $^1$H NMR (DMSO-$d_6$; 400 MHz): δ 12.90 (1.5H, br s, N$\underline{H}$ or O$\underline{H}$), 7.85 (1H, d, J 8.0, (pyrimidine)CC$\underline{H}$), 7.81 (2H, s, (Cl)CC$\underline{H}$), 7.42–7.39 (2H, m, (O$_2$SNH)CC$\underline{H}$ and (pyrimidine)CC(H)C$\underline{H}$ or (O$_2$SNH)CC(H)C$\underline{H}$), 7.18–7.14 (1H, m, pyrimidine)CC(H)C$\underline{H}$ or (O$_2$SNH)CC(H)C$\underline{H}$; m/z (ES−) 515, 513, 511 chlorine isotope cluster (5%, 15%, 15%, [M+Na−1]$^-$), 492, 490, 488 chlorine isotope cluster (15%, 35%, 35%, [M−1]$^-$), 448, 446, 444 chlorine isotope cluster (10%, 25%, 20%, [M−CO$_2$H]$^-$).

EXAMPLE 5

2-(2-Thienyl)-4,5-dihydroxypyrimidine-6-carboxylate (24)

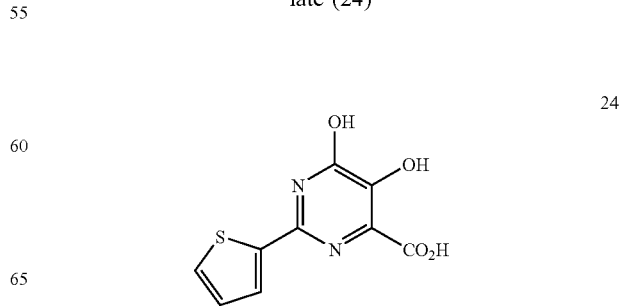

24

-continued

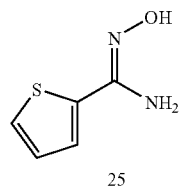

25

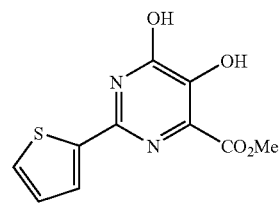

26

A solution of 2-thiophene amidoxime 25 (1.00 g, 7.03 mmol) in chloroform (5 ml) was treated dropwise with dimethyl acetylenedicarboxylate (1.00 g, 7.17 mmol) and the resulting solution was stirred at room temperature for 2 h. The mixture was concentrated in vacuo to give a residue which was taken up in p-xylene (5 ml) and heated under reflux for 5 h. The mixture was cooled to room temperature and the precipitate was collected by filtration. After washing with methanol and diethyl ether the precipitate was crystallized from acetic acid to afford methyl 2-(2-thienyl)-4,5-dihydroxypyrimidine-6-carboxylate 26 (470 mg, 26%) as a solid. $^1$H NMR (DMSO-d$_6$): δ 13.20 (1H, bs), 10.48 (1H, bs), 7.99 (1H, d, J 3.5), 7.76 (1H, d, J 5), 7.16 (1H, dd, J 5, 3.5), 3.84 (3H, s).

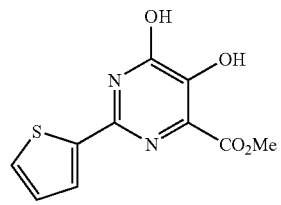

26

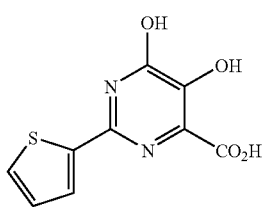

24

A suspension of methyl 2-(2-thienyl)-4,5-dihydroxypyrimidine-6-carboxylate 26 (300 mg, 1.19 mmol) in 1N aqueous sodium hydroxide (2 ml) was heated at 50° C. for 3 h. The resulting mixture was cooled to room temperature and acidified with 1N aqueous hydrochloric acid. The precipitate was collected and washed with water and diethyl ether, and dried to give the title compound 24 (212 mg, 75%) as a brown solid. $^1$H NMR (DMSO-d$_6$): δ 12.40 (1H, bs), 7.84 (1H, d, J 4), 7.61 (1H, d, J 5.5), 7.09 (1H, dd, J 5.5, 4). $^{13}$C NMR (DMSO-d$_6$): δ 169.0, 161.6, 156.0, 138.4, 136.1, 136.2, 128.9, 127.8, 125.7. MS m/z (MH)$^+$ 239.0.

EXAMPLE 6

2-[3-(2-Chlorophenylmethylaminocarbonylamino) thien-2-yl]-4,5-dihydroxypyrimidine-6-carboxylate (27)

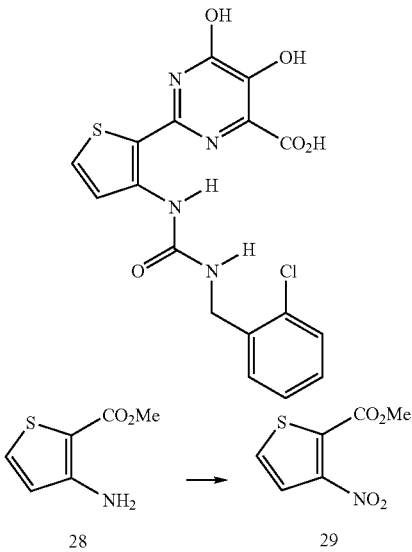

A modification of the method described by Huddleston (*Synth. Commun.*, 1995, 25, 3729) was used, as follows:

Commercial methyl 3-amino-2-thiophenecarboxylate 28 (75 g, 0.48 mol) was suspended in water (125 ml) and treated with concentrated hydrochloric acid (125 ml). The resulting suspension was stirred for 45 min at room temperature then cooled to −10° C. with an ice/salt bath (internal thermometer). A solution of sodium nitrite (33 g, 0.48 mol) in water (80 ml) was carefully added via dropping funnel, while internal temperature was kept between −5 and 0° C. After the addition, the reaction mixture was stirred for 1 h at 0° C., then treated in one portion with a solution of sodium tetrafluoroborate (79 g, 0.72 mol) in water (150 ml). The precipitated salt was isolated by filtration, washed with cold 5% aqueous sodium tetrafluoroborate (2×180 ml), ethanol (2×180 ml) and diethyl ether (2×180 ml), then dried in the air. The beige solid (98.5 g, 81%) thus obtained was used without further purification.

Activated copper bronze (19.1 g, 0.3 mol; see Vogel: *Practical Organic Chemistry*, p. 426 for activation) was added to a mechanically stirred solution of sodium nitrite (82.8 g, 1.2 mol) in water (180 ml). A suspension of the foregoing salt (25.6 g, 0.1 mol) in water (100 ml) was added to the vigorously stirred mixture portionwise over 1 h at room temperature. After the addition, stirring was continued for another hour. The reaction mixture was diluted with dichloromethane (500 ml) and filtered through diatomaceous earth (Celite). After separation of the phases, the aqueous phase was extracted with dichloromethane (4×300 ml) and the combined organic layers were dried over sodium sulfate in the presence of activated charcoal. Filtration and evaporation afforded 17.3 g (92%) of a red solid, which was used without further purification. $^1$H NMR (400 MHz, DMSO-d$_6$): δ 7.48 (1H, d, J 5), 7.43 (1H, d, J 5), 3.90 (3H, s).

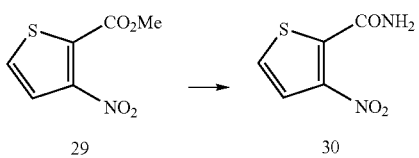

The ester 29 (25 g, 0.13 mol), prepared as described above, was stirred for 24 h at 100° C. in a well-closed Pyrex bottle in the presence of 2M methanolic ammonia (405 ml, 0.8 mol). The volatiles were removed in vacuo and the residue crystallized from hot ethyl acetate to afford 16.5 g (74%) of 3-nitrothiophene-2-carboxamide 30. $^1$H NMR (400 MHz, DMSO-$d_6$): δ 8.21 (1H, bs), 7.91 (1H, bs), 7.73 (1H, d, J 5), 7.57 (1H, d, J 5), 3.28 (3H, s). An analytical sample was obtained by further recrystallization from ethyl acetate; elemental analysis, calc. for $C_5H_4N_2O_3S$: C, 34.88; H, 2.34; N, 16.27. Found: C, 34.75; H, 2.24; N, 15.96.

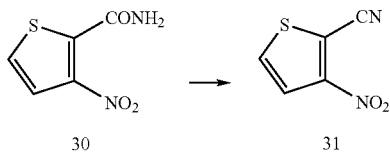

The amide 30 (15.5 g, 90 mmol), prepared as described above, was dissolved in dichloromethane (700 ml). Triethylamine (27.2 g, 37.6 ml, 270 mmol) was added and the solution cooled to 0° C. After dropwise addition of neat trifluoroacetic anhydride (24.6 g, 16.5 ml, 117 mmol), the reaction was allowed to warm to room temperature and stirred for 1 h. The solution was concentrated in vacuo, the residue taken into ethyl acetate and then washed successively with hydrochloric acid (1N, 2×), water (1×), saturated aqueous sodium hydrogencarbonate (2×) and brine. Drying over sodium sulfate and removal of solvent gave a dark solid, which was purified by flash chromatography (400 g of silica gel, petroleum ether:ethyl acetate 7:3+1% MeOH as eluent) yielding 2-cyano-3-nitrothiophene 31 (13.4 g, 96.5%). $^1$H NMR (CDCl$_3$): δ 7.75 (1H, d, J 5.5), 7.68 (1H, d, J 5.5). An analytical sample was obtained by recrystallization from dichloromethane/n-pentane, m.p. 87–88° C.; elemental analysis, calc. for $C_5H_2N_2O_2S$: C, 38.96; H, 1.31; N, 18.17; S, 20.80. Found: C, 38.92; H, 1.20; N, 18.03; S, 21.31.

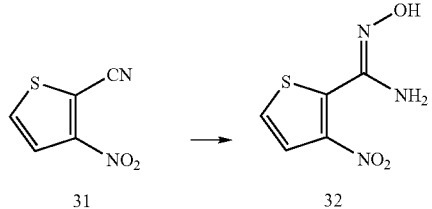

The nitrile 31 (86.93 mmol, 13.4 g), prepared as described above, was suspended in water (360 ml) and ethanol (48 ml). Sodium carbonate (15.7 g, 147.8 mmol) and hydroxylamine (18.7 g, 287 mmol) were added and the mixture was left at room temperature for 24 h. The orange solid was isolated by filtration, washed with a small portion of diethyl ether and dried. The amidoxime 32 (14.0 g, 86%) was obtained as an orange solid. $^1$H-NMR (DMSO-$d_6$): δ 9.95 (1H, bs), 7.68 (1H, d, J 5.3), 7.60 (1H, d, J 5.3), 6.08 (2H, bs). MS (ESI) 188 [M+H]$^+$. An analytical sample was obtained by recrystallization from dichloromethane/n-pentane, m.p. 201–202° C.; elemental analysis, calc. for $C_5H_5N_3O_3S$: C, 32.09; H, 2.69; N, 22.45; S, 17.13. Found: C, 32.34; H, 2.64; N, 21.96; S, 17.47.

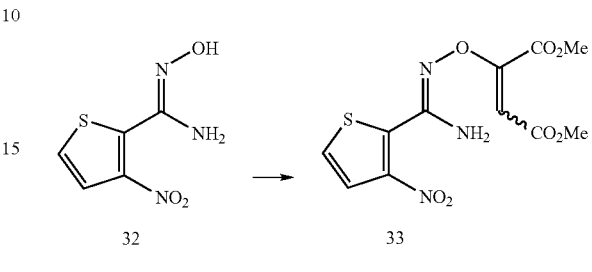

The amidoxime 32 (11.87 g, 63.90 mmol), prepared as described above, was suspended in dichloromethane (250 ml). Triethylamine (0.5 ml) and dimethyl acetylenedicarboxylate (9.53 g, 67.1 mmol, filtered over basic alumina) were added. The mixture was refluxed for 3 h and became homogeneous during this time. Evaporation of the dichloromethane gave a red oil (20.88 g), which was dissolved in ethyl acetate (400 ml). After washing with water and brine, the organic phase was dried over sodium sulfate and the solution was concentrated in vacuo. The residual oil (20.5 g, 97%) was used without further purification. $^1$H NMR (CDCl$_3$), two diastereomers (2.5:1*): δ 7.61*, 7.58 (1H, d, J 5.6), 7.38*, 7.33 (1H, d, J 5.6), 6.10, 5.84* (2H, bs), 5.94, 5.88* (1H, s), 3.90*, 3.83 (3H, s), 3.71, 3.68* (3H, s). MS (ESI) 330 [M+H]$^+$, 352 [M+Na]$^+$.

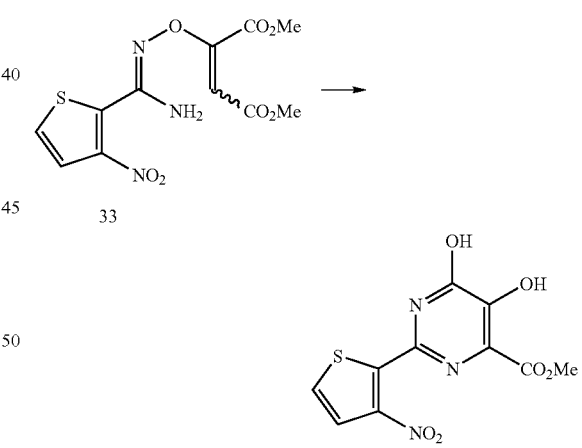

To a flask containing the oxime 33 (30.7 g, 93.28 mmol), prepared as described above, was added xylene (212 ml). The reaction was heated at 140° C. until the disappearance of the starting material was evident by TLC (7 h). The reaction mixture was stored in a refrigerator at 4° C. overnight and the precipitate isolated by filtration. The solid was washed with ethyl acetate and petroleum ether and dried in vacuo. The product was obtained as an off-white powder (13.27 g, 48%). $^1$H NMR (DMSO-$d_6$): δ 13.30 (1H, bs), 11.80 (1H, bs), 7.89 (1H, d, J 5.4), 7.71 (1H, d, J 5.4), 3.82

(3H, s). MS (ESI) 296 [M–H]. (In addition to the desired product, the ¹H NMR spectrum in DMSO showed about 6% of a dehydroxylated product).

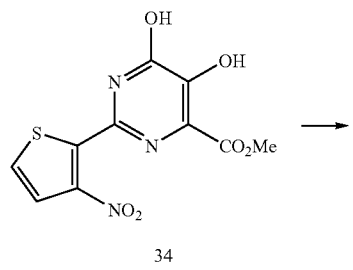

34

The pyrimidine 34 (1.5 g, 5.05 mmol), prepared as described above, was dissolved in a mixture of ethyl acetate and methanol (2:1, 200 ml). Palladium-on-charcoal (10% Pd, 1.5 g) was added, and the reaction stirred under an atmosphere of hydrogen for 5 h at ambient temperature. The catalyst was removed by filtration and washed with hot ethyl acetate and methanol. After evaporation the amine 35 (1.08 g, 80%) was obtained as a yellow solid. ¹H NMR (DMSO-$d_6$): δ 8.80 (3H, bs), 7.48 (1H, d, J 5.2), 6.67 (1H, d, J 5.2), 3.85 (3H, s). MS (ESI) 268 [M+H]⁺.

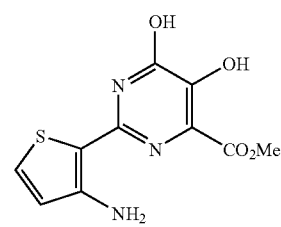

35

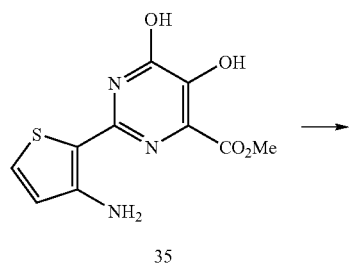

27

The amine 35 (300 mg, 1.12 mmol), prepared as described above, was dissolved in pyridine (10 ml). Commercial 2-chlorobenzyl isocyanate (225 mg, 1.34 mmol) was added dropwise. The reaction was monitored by analytical HPLC. After consumption of amine, the solution was concentrated in vacuo and the residue was dissolved in a large volume of ethyl actetate, washed with hydrochloric acid (1N), brine, and dried over sodium sulfate. The compound (methyl ester) obtained after concentration of the solution in vacuo was hydrolyzed using sodium hydroxide (4.5 ml, 1N) and methanol (3 ml) at 80° C. for 30 min. The solution was then cooled in an ice-bath and acidified with hydrochloric acid (1N) to pH 2. The precipitated solid was isolated by filtration, washed with water and diethyl ether and dried. It was boiled once in ethyl acetate, filtered and washed again with ethyl acetate and diethyl ether, and dried in vacuo to give the crude product. This was purified by preparative reversed phase HPLC using a Waters Prep-NovaPak column (HR C18, 40×100 mm, 6 micron) and 0.05% trifluoroacetic acid in water (solvent A) and 0.05% trifluoroacetic acid in acetonitrile (solvent B) as eluents; gradient: 80% A, 2 min isocratic, in 2 min to 60% A, then in 8 min to 30% A; flow 35 ml/min, giving 105 mg (22%) of the title compound as a yellow powder after lyophilization. ¹H NMR (DMSO-$d_6$): δ 12.70 (1H, bs), 11.05 (1H, bs), 8.80, 7.83 (1H, d, J 5.4), 7.61 (1H, d, J 5.4), 7.45 (2H, m), 7.36 (2H, m), 7.00 (1H, bs), 4.42 (2H, bd, J 5.9). MS (ESI) 421, 419 [M–H].

EXAMPLE 7

2-[4-(2-Chlorophenylmethylaminocarbonylamino) thien-3-yl]-4,5-dihydroxypyrimidine-6-carboxylate (36)

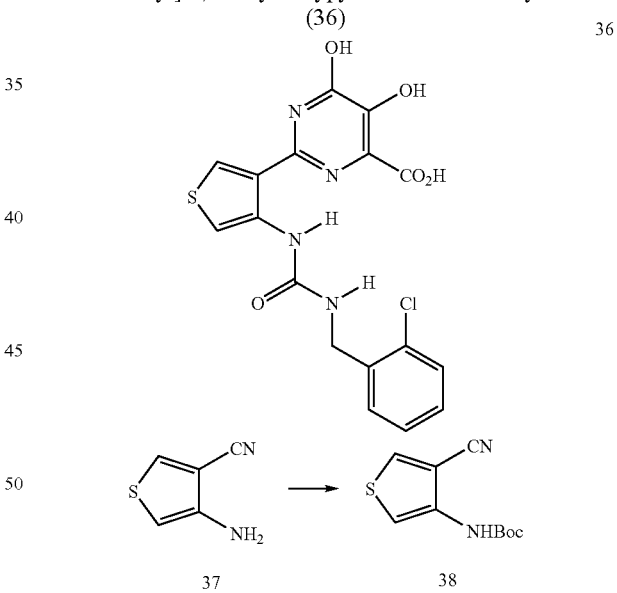

A solution of 3-amino-4-cyanothiophene 37 (10 g, 80.5 mmol) in methylene chloride (125 ml) was treated with pyridine (7.5 ml) and di-tert-butyl dicarbonate (36.9 g, 169.14 mmol) then heated under reflux for 45 min. The cooled solution was concentrated in vacuo and the residue was diluted with 1N hydrochloric acid. After extraction with ethyl acetate (3×150 ml) the dried organic layer was concentrated in vacuo to give 3-tert-butyloxycarbonylamino-4-thiophene carbonitrile 38 (15 g, 83%) as a solid. ¹H NMR (DMSO-$d_6$): δ 9.35 (1H, bs), 8.42 (1H, s), 7.41 (1H, s), 1.47 (9H, s).

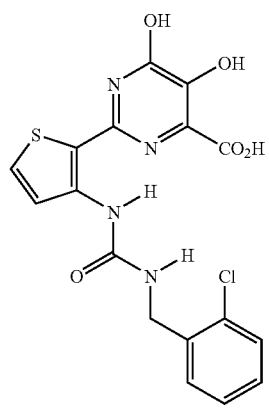

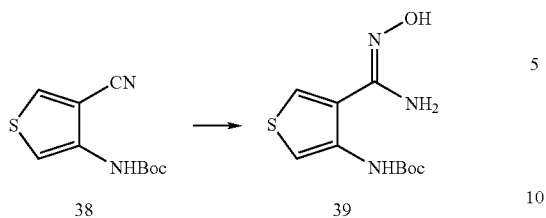

A solution of N-Boc-3-amino-4-cyanothiophene (3.04 g, 13.5 mmol) and hydroxylamine hydrochloride (1.32 g, 69.5 mmol) in MeOH (25 ml) was treated with Et$_3$N (2.32 g, 23 mmol) and heated at 50° C. for 12 h. The solution was cooled and concentrated, and the residue was taken up with H$_2$O and AcOEt. The organic layer was separated and dried, then concentrated to give 3-tert-butyloxycarbonylamino-4-thiophene amidoxime 39 (3.47 g, 100%) as a solid. $^1$H NMR (DMSO-d$_6$): δ 10.15 (1H, s), 9.85 (1H, s), 7.90 (1H, s), 7.51 (1H, s), 6.05 (2H, s), 1.47 (9H, s).

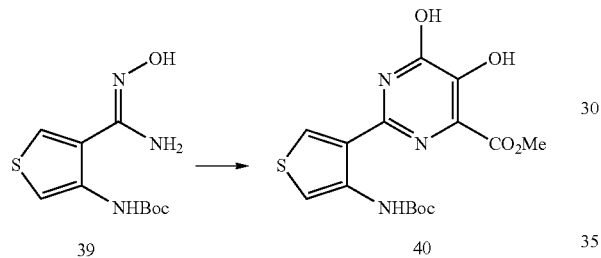

Dimethyl acetylenedicarboxylate (1.84 g, 13 mmol) was added dropwise to a stirred solution of oxime 39 (3.27 g, 12.7 mmol). The mixture was treated with triethylamine (0.25 ml) and heated under reflux for 3 h. The cooled solution was concentrated in vacuo and the residue was filtered through a short path of SiO$_2$ (3:1 petroleum ether: ethyl acetate as eluent) to give a solid which was taken up in p-xylene (100 ml). The solution was heated under reflux for 3.5 h and then cooled and filtered. The precipitate was washed with methanol (5 ml) and diethyl ether (20 ml) and dried to give methyl 2-(3-tert-butyloxycarbonylamino-4-thienyl)-4,5-dihydroxypyrimidine-6-carboxylate 40 (1.3 g, 28%) as a solid. $^1$H NMR (DMSO-d$_6$): δ 13.10 (1H, bs), 10.90 (1H, s), 10.78 (1H, bs), 8.49 (1H, s), 7.70 (1H, s), 3.85 (3H, s), 1.48 (9H, s).

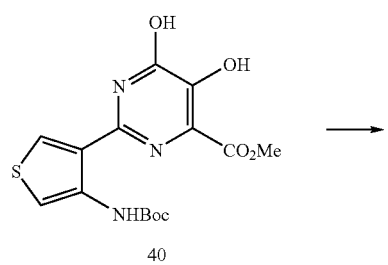

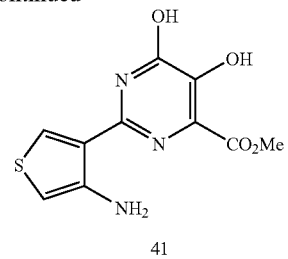

Ester 40 (828 mg, 2.25 mmol), prepared as described above, was treated with a 6:4 mixture of methylene chloride: trifluoroacetic acid (8 ml). The solution was stirred for 20 min then concentrated in vacuo and the residue dried to give methyl 2-(3-amino-4-thienyl)-4,5-dihydroxy-pyrimidine-6-carboxylate trifluoroacetate (860 mg, 99%) as a solid. $^1$H NMR (DMSO-d$_6$): δ 8.32 (1H, s), 6.75 (1H, s), 3.87 (3H, s). MS m/z (MH)$^+$ 268.0.

A solution of amine 41 (200 mg, 0.58 mmol) in pyridine (5 ml) was treated dropwise with 2-chlorobenzyl isocyanate and the mixture was stirred for 8 h. The solution was concentrated in vacuo and the residue was washed with 1N hydrochloric acid (2 ml), water (2 ml) and diethyl ether (2 ml) to give a solid (199 mg) which was taken up in 1N sodium hydroxide (2 ml). The mixture was heated at 60° C. for 5.5 h then cooled to 0° C. and acidified with 1N hydrochloric acid. The precipitate was collected and washed with water (5 ml) and diethyl ether (5 ml). Purification of a 40 mg portion by HPLC (MacheryNagel Nucleosil C$_{18}$ 25 mm×20 cm; eluent MeCN+0.1% TFA/H$_2$O+0.1% TFA; gradient from 30% MeCN to 90% MeCN in 10 min; retention time=8 min) afforded the title compound (12 mg)

as a white solid. $^1$H NMR (DMSO-d$_6$): δ 12.80 (1H, bs), 11.60 (1H, s), 8.35 (d, J 4), 7.61 (1H, d, J 4), 7.43 (2H, m), 7.32 (2H, m), 6.52 (1H, t, J 4.8), 4.41 (2H, d, J 4.8). MS m/z (M−) 419.0.

EXAMPLE 8

5,6-Dihydroxy-2-[4-(1-naphthylsulfonylaminocarbonylamino)thien-3-yl]pyrimidine-4-carboxylic acid (630)

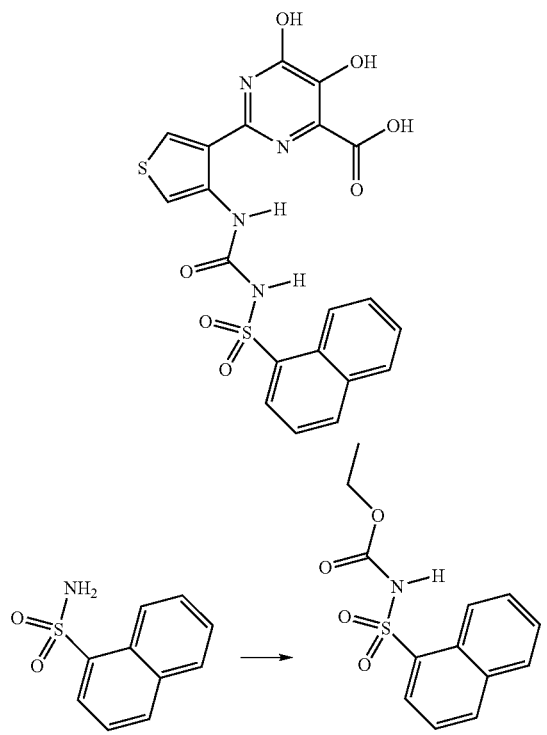

A mixture of 1-naphthalene sulfonamide (769 mg, 3.67 mmol) and potassium carbonate (563 mg, 4.07 mmol) in 2-butanone (9 ml) was heated under reflux for 30 min. Ethyl chloroformate (430 mg, 3.96 mmol) was added dropwise and the resulting solution was heated under reflux for 3 h. The mixture was cooled and diluted with H$_2$O (30 ml) and AcOEt (10 ml). The aqueous layer was collected and adjusted to pH 2 by addition of 1N HCl (aq). Extraction with AcOEt (2×20 ml) and concentration of the dried organic extracts afforded ethyl 1-naphthylsulfonylcarbamate (674 mg, 67%) as a white solid. $^1$H NMR (DMSO-d$_6$): δ 12.35 (bs, 1H), 8.57 (1H, d, J 8.6), 8.29 (2H, m), 8.11 (1H, d, J 7.7), 7.71 (3H, m), 3.90 (2H, q, J 7.1), 0.99 (3H, t, J 7.1).

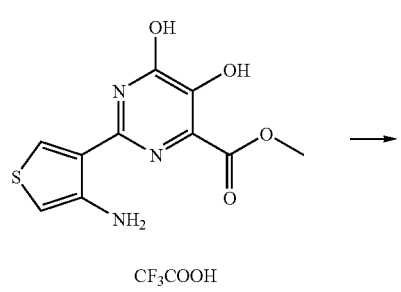

41

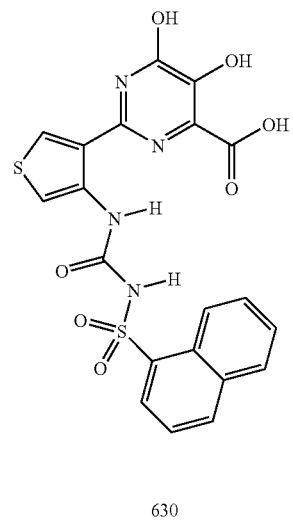

630

A solution of amine 41 (200 mg, 0.52 mmol) in toluene (4 ml) was treated with triethylamine (99 mg, 0.98 mmol) to adjust the pH to 6. Ethyl 1-naphthylsulfonylcarbamate (137 mg, 0.49 mmol) was added and the mixture was heated to reflux for 30 min. The mixture was cooled to room temperature and treated with 1N HCl (aq). The precipitate was filtered and triturated with H$_2$O and Et$_2$O then dried to afford methyl 5,6-dihydroxy-2-[4-(1-naphthylsulfonylaminocarbonylamino)thien-3-yl]pyrimidine-4-carboxylate (224 mg, 86%) as a solid. A portion of this compound (109 mg, 0.22 mmol) was dissolved in a 4:1 mixture of THF/H$_2$O (2.2 ml) and was treated with LiOH.H$_2$O (46 mg, 1.09 mmol). The mixture was heated overnight at 50° C., then the solution was cooled and the THF was removed under vacuum. The residue was acidified to pH 2 with 1N HCl (aq) and the resulting precipitate was collected by filtration, triturated with H$_2$O and Et$_2$O, and dried to afford the title compound (101 mg, 94%) as a solid. $^1$H NMR (DMSO-d$_6$): δ 12.90 (1H, bs), 11.30 (1H, bs), 8.63 (1H, d, J 8.5), 8.28 (3H, m), 8.09 (1H, d, J 8), 7.69 (3H, m), 7.45 (1H, d, J 3.3); MS (ESI) 485 [M−H].

EXAMPLE 9

5,6-Dihydroxy-2-{3-[(E)-2-phenylethenyl]thien-2-yl}pyrimidine-4-carboxylic acid (628)

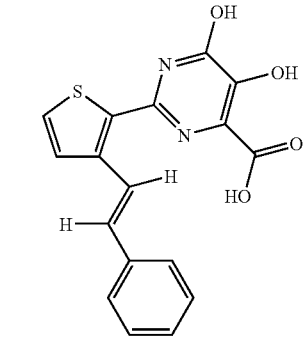

628

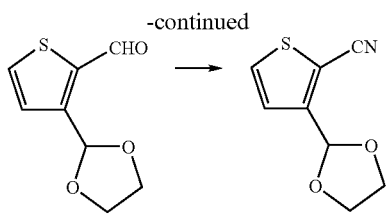

3-(1,3-Dioxolan-2-yl)thiophene-2-carbaldehyde (13.1 g, 71.11 mmol), prepared by a method described by Hibino (S. Hibino et al., *J. Org. Chem.* 1984, 49, 5006), was dissolved in ethanol (80 ml). At room temperature a solution of hydroxylamine hydrochloride (two equivalents) and sodium hydrogencarbonate (one equivalent) in water (130 ml) was added and the resultant mixture stirred at this temperature for two hours. The ethanol was removed under reduced pressure and the aqueous phase extracted with ethyl acetate (3×300 ml). The combined organic layers were washed with brine and dried over sodium sulfate. Evaporation after filtration afforded 3-(1,3-dioxolan-2-yl)thiophene-2-carbaldehyde oxime as an off-white solid (quantitative). $^1$H NMR (2 isomers, 1:1) (CDCl$_3$): δ 8.56 (1H, s), 8.45 (1H, s), 7.50 (1H, d, J 5.26), 7.25 (1H, d, J 5.2), 7.21 (1H, d, J 5.28), 7.12 (1H, d, J 5.2), 6.09 (1H, s), 5.99 (1H, s), 4.17–4.00 (2H, m).

The foregoing aldoxime (10.09 g, 50.07 mmol) was dissolved in acetonitrile (139 ml) containing copper(II) acetate hydrate (1.01 g, 5.07 mmol). Triethylamine (19.6 ml) was added dropwise and the resulting mixture was heated to reflux. After 30 min TLC (hexanes/ethyl acetate 3:1) indicated complete conversion of starting material. After cooling the reaction mixture to room temperature, the solvents were evaporated under reduced pressure and the crude product was purified by flash chromatography (eluent hexanes/ethyl acetate 3:1) to give 7.78 g (87%) of 3-(1,3-dioxolan-2-yl)thiophene-2-carbonitrile as an oily liquid. $^1$H NMR (CDCl$_3$): δ 7.55 (1H, d, J 5.20), 7.21 (1H, d, J 5.20), 6.04 (1H, s), 4.21–4.06 (4H, m); $^{13}$C NMR (CDCl$_3$): δ 149.69, 131.89, 126.79, 112.83, 108.22, 98.60, 65.52.

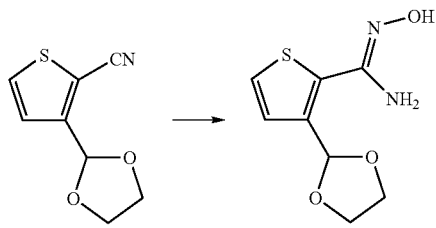

To a solution of the foregoing nitrile (5.0 g, 27.59 mmol) in ethanol (20 ml) was added a solution of hydroxylamine hydrochloride (3.7 equivalents) and sodium carbonate (1.7 equivalents) in water (50 ml). The resulting mixture was heated to 40° C. for 5 h, then cooled to room temperature. The colourless precipitate was isolated by filtration, dried under a stream of air and azeotroped with toluene (2×) to give 3-(1,3-dioxolan-2-yl)thiophene-2-amidoxime as an off-white solid (4.36 g). $^1$H NMR (DMSO-d$_6$): δ 9.83 (1H, s), 7.48 (1H, d, J 5.18), 7.15 (1H, d, J 5.18), 6.05 (1H, s), 5.77 (2H, bs), 4.05 (2H, m), 3.91 (2H, m).

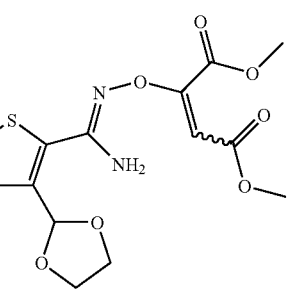

The foregoing compound (4.35 g, 20.3 mmol) was suspended in dichloromethane (200 ml). Triethylamine (0.2 ml) and dimethyl acetylenedicarboxylate (2.89 g, 20.3 mmol) were added. The mixture was refluxed for 5 h, then another portion of dimethyl acetylenedicarboxylate (289 mg) was added and the mixture was left stirring at room temperature for 3 days. Evaporation gave a red oil, which was purified by flash chromatography (hexanes/ethyl acetate 3:1, then 2:1 with 0.2% methanol). The product was obtained as a yellow oil (6.38 g, two diastereomers 1.5:1*). $^1$H NMR (CDCl$_3$): δ 7.67*, 7.64 (1H, d, J 5.17), 7.19*, 7.16 (1H, d, J 5.17), 7.08*, 6.70 (2H, bs), 6.02*, 5.99 (1H, s), 5.73, 5.69* (1H, s), 4.04 (2H, m), 3.93 (2H, m), 3.80*, 3.77 (3H, s), 3.62, 3.61* (3H, s). MS m/z (MH)$^+$ 357.

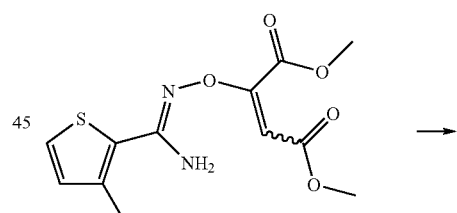

The foregoing compound (6.29 g, 17.65 mmol) was heated at reflux in xylene (120 ml) for 6 h and then cooled to room temperature. The rection was filtered to remove some black precipitate and the solution cooled to 0° C. An orange solid precipitated, which was collected by filtration.

The solution was reduced to half of its volume under reduced pressure and the precipitate that formed upon cooling to 0° C. was collected and united with the first batch. Thus, 2.0 g of cyclized material was obtained. A portion of this material (512 mg) was heated to 50° C. in formic acid (50 ml) for 1 h. The formic acid was removed under reduced pressure and the remaining solid was azeotroped with toluene (2×) to obtain crude methyl 2-(3-formylthien-2-yl)-5,6-dihydroxypyrimidine-4-carboxylate (452 mg). This material was used without further purification. $^1$H NMR (DMSO-d$_6$): δ 9.83 (1H, s), 7.48 (1H, d, J 5.18), 7.15 (1H, d, J 5.18), 6.05 (1H, s), 5.77 (2H, bs), 4.05 (2H, m), 3.91 (2H, m). MS m/z (M+H) 281.

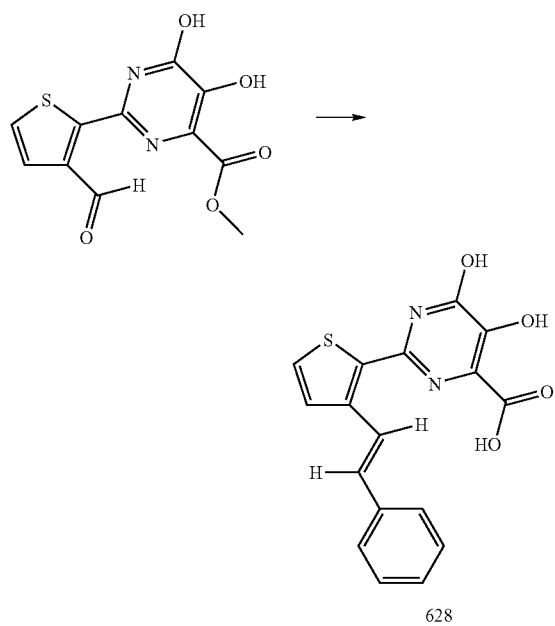

628

The crude foregoing product (80 mg, 0.29 mmol) was dissolved in methanol (1 ml) and N,N-dimethylformamide (2 ml) and treated with sodium methanolate (2 equivalents). The resulting red solution was added to a solution of benzyl triphenylphosphonium bromide (247 mg, 2 equivalents) and sodium methanolate (34 mg) in anhydrous methanol (5 ml), which was prepared 20 min before at room temperature. The resulting mixture was heated to reflux. After 4 h some of the methanol was evaporated under reduced pressure, ethyl acetate was added, and the solution was washed with hydrochloric acid (1N) and brine. After drying over sodium sulfate, filtration and evaporation under reduced pressure, an orange solid was obtained, which was treated with diethyl ether (5×7 ml). The remaining solid (60 mg) was dissolved in methanol (1 ml) and sodium hydroxide (1 ml, 0.5N) was added. After heating to 80° C. for 1 h, the reaction mixture was diluted with water, and then at room temperature hydrochloric acid (1N) was added dropwise until pH 2 was reached. The precipitate was isolated by filtration, washed with diethyl ether and then lyophilized from acetonitrile and water. 5,6-Dihydroxy-2-{3-[(E)-2-phenylethenyl]thien-2-yl}pyrimidine-4-carboxylic acid was obtained as a yellow powder (35 mg). $^1$H NMR (DMSO-d$_6$): δ 13.00 (1H, bs), 8.03 (1H, bd, J 16.9), 7.71 (1H, d, J 5.2), 7.63 (1H, d, J 5.2), 7.59 (2H, d, J 7.5), 7.36 (2H, t, J 7.5), 7.27 (1H, d, J 7.7), 7.23 (1H, d, J 16.9). MS m/z 341 (M+H)$^+$.

These and other compounds of the invention which can be prepared by analogous methods are set out in Tables I to XII below. Where "X$_1$" appears in the Table it is not part of the group "R1" but represents the remainder of the molecule apart from R1. The IC$_{50}$ values in μM of these compounds can be measured in the following way.

Test for Inhibition of Hepatitis C Virus RdRp

WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) as a template and oligo(U) as a primer. Incorporation of tritiated UTP is quantified by measuring acid-insoluble radioactivity. The present inventors have employed this assay to screen the various compounds described above as inhibitors of HCV RdRp.

Incorporation of radioactive UMP was measured as follows. The standard reaction (1001 μl) was carried out in a buffer containing 20 mM tris/HCl pH 7.5, 5 mM MgCl$_2$, 1 mM DTT, 50 mM NaCl, 1 mM EDTA, 2 OU Rnasin (Promega), 0.05% Triton X-100, 1 μCi [$^3$H]-UTP (40 Ci/mmol, NEN), 10 μM UTP and 10 μg/ml poly(A). Oligo (U)$_{12}$ (1 μg/ml, Genset) was added as a primer. The final NSSB enzyme concentration was 20 nM. After 1 h incubation at 22° C. the reaction was stopped by adding 100 μl of 20% TCA and applying samples to DE81 filters. The filters were washed thoroughly with 5% TCA containing 1M Na$_2$HPO$_4$/NaH$_2$PO$_4$, pH 7.0, rinsed with water and then ethanol, air dried, and the filter-bound radioactivity was measured in the scintillation counter. By carrying out the reaction in the presence of various concentrations of each of the compounds set out above it was possible to determine IC$_{50}$ values for each compound utilizing the formula:

% residual activity=$100/(1+[I]/IC_{50})^s$ where [I] is the inhibitor concentration and "s" is the slope of the inhibition curve.

TABLE I

| Ex. No. | R1 |
|---|---|
| 4 (Compound No. 21) | X$_1$—N—S(O)$_2$—(2,4,6-trichlorophenyl) |

TABLE I-continued
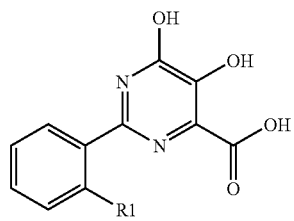
| Ex. No. | R1 |
|---|---|
| 42 | 2,3,4-trichlorophenylsulfonyl-NH-X₁ |
| 43 | (2-chloro-6-methylbenzyl)-NH-C(O)-N(X₁)- |
| 2 (Compound No. 9) | (2-chlorobenzyl)-NH-C(O)-N(X₁)- |
| 44 | (2-bromobenzyl)-NH-C(O)-N(X₁)- |
| 45 | 2,4-dichloro-5-methylphenylsulfonyl-NH-X₁ |
TABLE I-continued
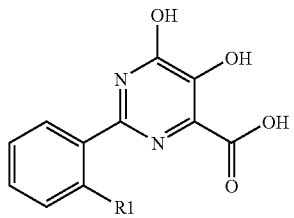
| Ex. No. | R1 |
|---|---|
| 46 | (2-trifluoromethylbenzyl)-NH-C(O)-N(X₁)- |
| 47 | (2-chlorophenylsulfonyl)-N-C(O)-NH-X₁ |
| 48 | 5-chloronaphthalen-2-ylsulfonyl-NH-X₁ |
| 49 | (2-fluorobenzyl)-NH-C(O)-N(X₁)- |
| 50 | (diphenylmethyl)-NH-C(O)-N(X₁)- |

TABLE I-continued

[Structure: 2-(2-R1-phenyl)-5,6-dihydroxy-pyrimidine-4-carboxylic acid]

| Ex. No. | R1 |
|---------|-----|
| 51 | X1-NH-C(O)-NH-CH2-(2,4-dichlorophenyl) |
| 52 | X1-NH-C(O)-NH-CH2-(2,3-dichlorophenyl) |
| 53 | X1-NH-C(O)-NH-CH2-(2,5-dichlorophenyl) |
| 54 | X1-NH-C(O)-NH-CH2-(3,4-dichlorophenyl) |
| 55 | X1-NH-SO2-(3,4-dichlorophenyl) |
| 56 | X1-NH-SO2-(3-methyl-5-chloro-benzothiophen-2-yl) |
| 57 | X1-NH-SO2-(4-bromo-2,5-dichloro-thiophen-3-yl) |
| 58 | X1-NH-C(O)-NH-CH2-(2-chloro-6-fluorophenyl) |
| 59 | X1-NH-SO2-(2,5-dimethyl-4-chlorophenyl) |
| 60 | X1-NH-C(O)-NH-CH2-phenyl |

TABLE I-continued

![Structure: 2-aryl-5,6-dihydroxy-pyrimidine-4-carboxylic acid with R1 on ortho position of phenyl]

| Ex. No. | R1 |
|---|---|
| 61 | X₁-N-C(=O)-N-CH₂-(2,4-dichloro-6-methylphenyl) |
| 62 | X₁-N-S(=O)₂-(thiophene-2-yl linked to 2-methylthiazol-4-yl) |
| 63 | X₁-N-C(=O)-O-CH₂-phenyl |
| 64 | X₁-N-S(=O)₂-(2-iodophenyl) |
| 65 | X₁-N-C(=O)-N-CH₂-(2-methoxyphenyl) |
| 66 | X₁-N-C(=O)-N-CH₂-(3-nitrophenyl) |
| 67 | X₁-N-C(=O)-N-CH₂-(4-fluorophenyl) |
| 68 | X₁-N-S(=O)₂-(2-nitrophenyl) |
| 69 | X₁-N-S(=O)₂-CH=CH-phenyl (trans) |
| 70 | X₁-N-S(=O)₂-N-CH₂-(2-chlorophenyl) |
| 71 | X₁-N-C(=O)-N-CH₂-(3-methylphenyl) |

TABLE I-continued
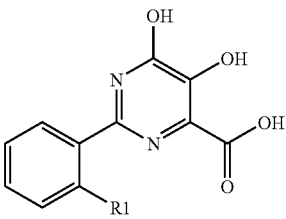
| Ex. No. | R1 |
|---|---|
| 72 | 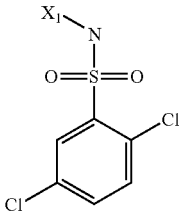 |
| 73 | 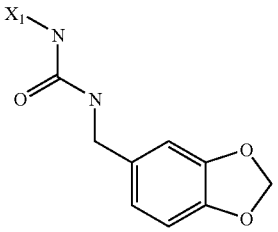 |
| 74 | 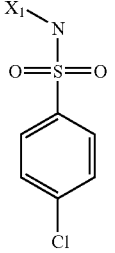 |
| 75 | 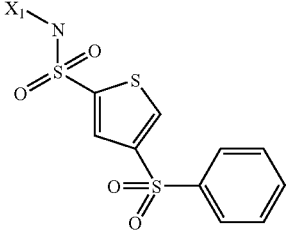 |
| 76 | 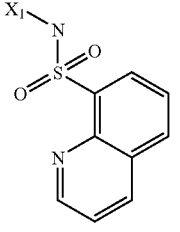 |
TABLE I-continued
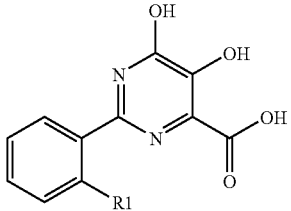
| Ex. No. | R1 |
|---|---|
| 77 | 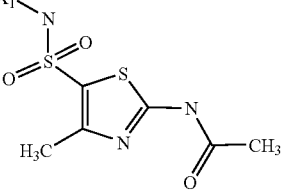 |
| 78 | 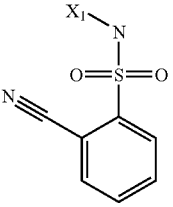 |
| 79 | 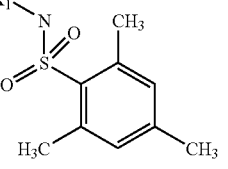 |
| 80 | 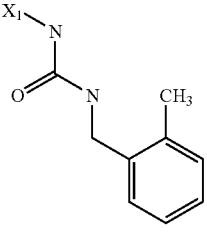 |
| 81 | |

TABLE I-continued

| Ex. No. | R1 |
|---|---|
| 82 | 3-carboxy-4-methoxy-benzenesulfonylamino (X₁-NH-SO₂-C₆H₃(COOH)(OCH₃)) |
| 83 | 3-bromo-benzenesulfonylamino |
| 84 | 2-chloro-4-trifluoromethyl-benzenesulfonylamino |
| 85 | 3-(2-phenylethyl)ureido |
| 86 | 3-nitro-benzenesulfonylamino |
| 87 | 3-(1-(naphthalen-1-yl)ethyl)ureido |
| 88 | 4-nitro-benzenesulfonylamino |
| 89 | 3-chloro-2-methyl-benzenesulfonylamino |
| 90 | 3-chloro-4-fluoro-benzenesulfonylamino |
| 91 | biphenyl-3-sulfonylamino |

TABLE I-continued

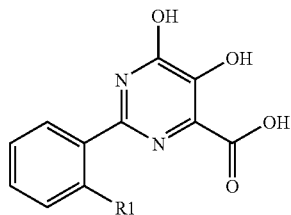

| Ex. No. | R1 |
|---|---|
| 92 | 2-(trifluoromethyl)phenylsulfonamide |
| 93 | naphthalene-1-sulfonamide |
| 94 | phenylurea |
| 95 | nitro |
| 96 | 3-phenylpropylurea |
| 97 | 2,5-bis(2,2,2-trifluoroethoxy)phenylsulfonamide |

TABLE I-continued

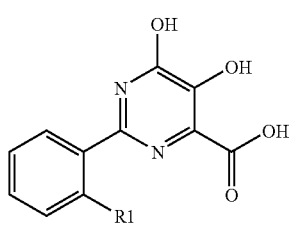

| Ex. No. | R1 |
|---|---|
| 98 | 4-((3-chloro-5-(trifluoromethyl)pyridin-2-yl)oxy)phenylsulfonamide |
| 99 | (biphenyl-2-ylmethyl)urea |
| 100 | (4-methoxybenzyl)urea |
| 101 | 4-bromo-2,6-difluorophenylsulfonamide |
| 102 | (3-(trifluoromethyl)phenyl)urea |

TABLE I-continued

[Structure: pyrimidine with OH, OH, COOH groups, 2-phenyl with R1 substituent]

| Ex. No. | R1 |
|---|---|
| 103 | X₁-N(H)-SO₂-(2,3,4-trifluorophenyl) |
| 104 | X₁-N(H)-SO₂-(4-hydroxyphenyl) |
| 105 | X₁-N(H)-SO₂-(benzo[1,2,5]oxadiazol-4-yl) |
| 106 | X₁-N(H)-C(O)-(benzothiophen-2-yl) |
| 107 | X₁-N(H)-C(O)-(3-cyanophenyl) |
| 108 | X₁-N(H)-SO₂-(4-methylphenyl) |

TABLE I-continued

[Same core structure]

| Ex. No. | R1 |
|---|---|
| 109 | X₁-N(H)-SO₂-(3-trifluoromethylphenyl) |
| 110 | X₁-N(H)-SO₂-(4-trifluoromethylphenyl) |
| 111 | X₁-N(H)-C(O)-N(H)-(indan-1-yl) |
| 112 | X₁-CH₂-O-phenyl |
| 113 | X₁-N(H)-C(O)-N(H)-(2-phenylcyclopropyl) |

TABLE I-continued

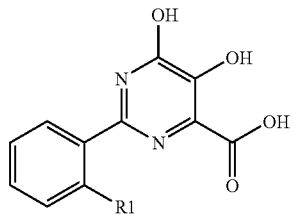

| Ex. No. | R1 |
|---|---|
| 114 | X₁-N(H)-SO₂-C₆H₄-C(CH₃)₃ (4-tert-butylphenylsulfonamide) |
| 115 | X₁-N(H)-SO₂-C₆H₄-OCH₃ (4-methoxyphenylsulfonamide) |
| 116 | X₁-N(H)-SO₂-C₆H₄-CH₂CH₃ (4-ethylphenylsulfonamide) |
| 117 | X₁-N(H)-C(O)-N(H)-cyclohexyl |
| 118 | X₁-Br |
| 119 | X₁-N(H)-SO₂-C₆H₄-F (2-fluorophenylsulfonamide) |
| 120 | X₁-OH |

TABLE I-continued

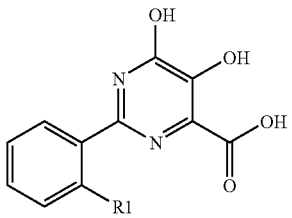

| Ex. No. | R1 |
|---|---|
| 121 | X₁-Cl |
| 122 | X₁-N(H)-SO₂-C₆H₃(CF₃)₂ (3,5-bis(trifluoromethyl)phenylsulfonamide) |
| 123 | X₁-N(H)-SO₂-C₆H₄-CH(CH₃)₂ (4-isopropylphenylsulfonamide) |
| 124 | X₁-N(H)-C(O)-C₆H₅ |
| 125 | X₁-N(H)-SO₂-C₆H₃(Cl)(NH₂) |
| 126 | X₁-NH₂ |
| 127 | X₁-N(H)-C(O)-N(H)-(1,2,3,4-tetrahydronaphthalen-1-yl) |

TABLE I-continued

![structure: 2-(2-R1-phenyl)-5,6-dihydroxypyrimidine-4-carboxylic acid]

| Ex. No. | R1 |
|---|---|
| 128 | X₁-N(H)-SO₂-[thiophene]-CH₂-N(H)-C(O)-phenyl |
| 129 | X₁—H |
| 130 | X₁-N(H)-SO₂-[3,5-dichlorophenyl]-O-[2-chloro-4-nitrophenyl] |
| 131 | X₁-N(H)-SO₂-[2-pyridyl] |
| 132 | X₁-N(H)-C(O)-[3-nitrophenyl] |
| 133 | X₁-N(H)-C(O)-CH₂CH₂-phenyl |
| 134 | X₁-N(H)-SO₂-[thiophene]-[1-methyl-3-(trifluoromethyl)pyrazol-5-yl] |
| 135 | X₁-N(H)-phenyl |
| 136 | X₁-N(H)-C(O)-[4-(trifluoromethoxy)phenyl] |
| 594 | X₁-N(H)-C(O)-N(H)-CH₂-[2-nitrophenyl] |
| 595 | X₁-N(H)-C(O)-N(H)-CH₂-[2-aminophenyl] |

TABLE I-continued
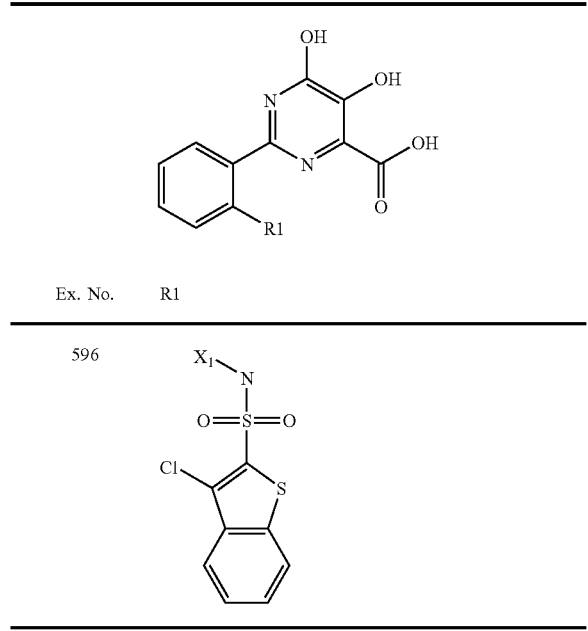
| Ex. No. | R1 |
|---|---|
| 596 | 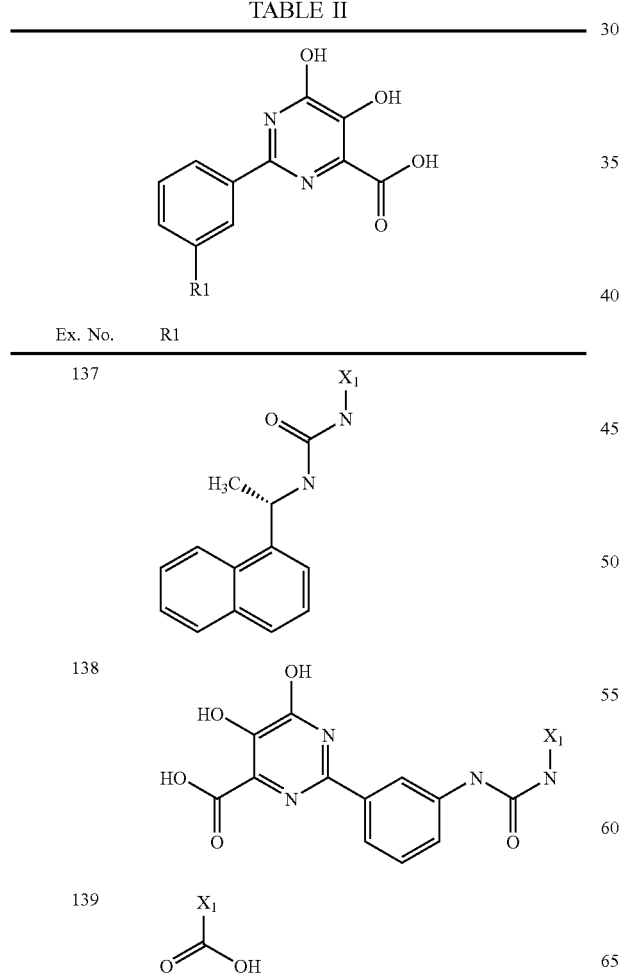 |
TABLE II
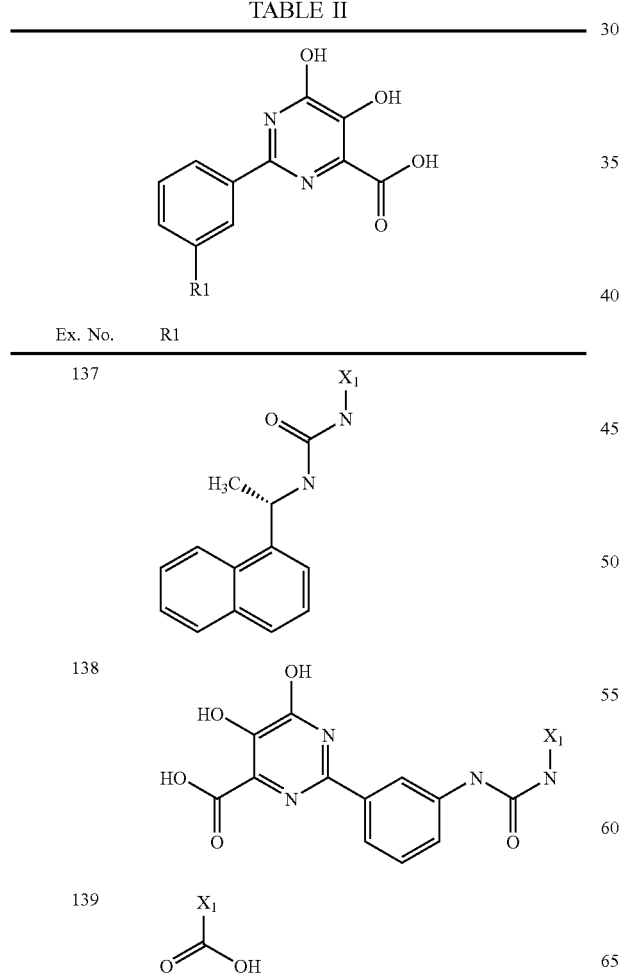
| Ex. No. | R1 |
|---|---|
| 137 | |
| 138 | |
| 139 | |
TABLE II-continued
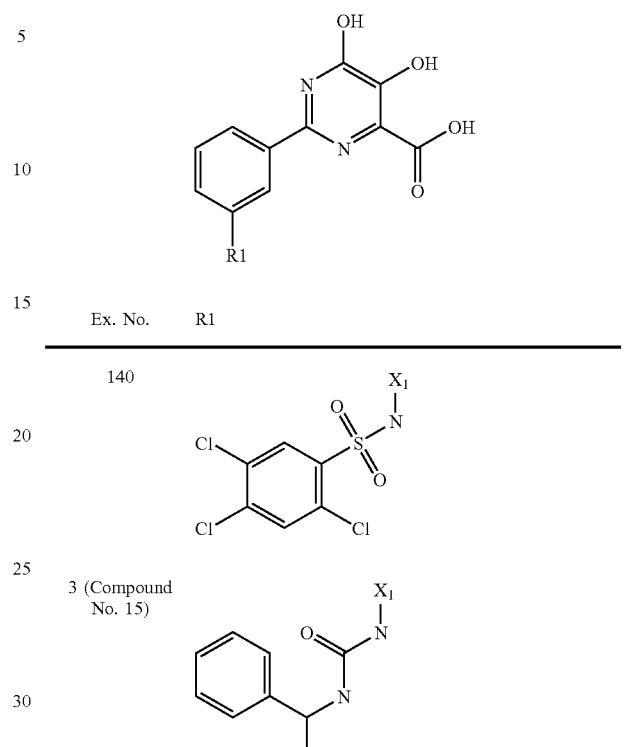
| Ex. No. | R1 |
|---|---|
| 140 | |
| 3 (Compound No. 15) | |
| 141 | |
| 142 | |
| 143 | 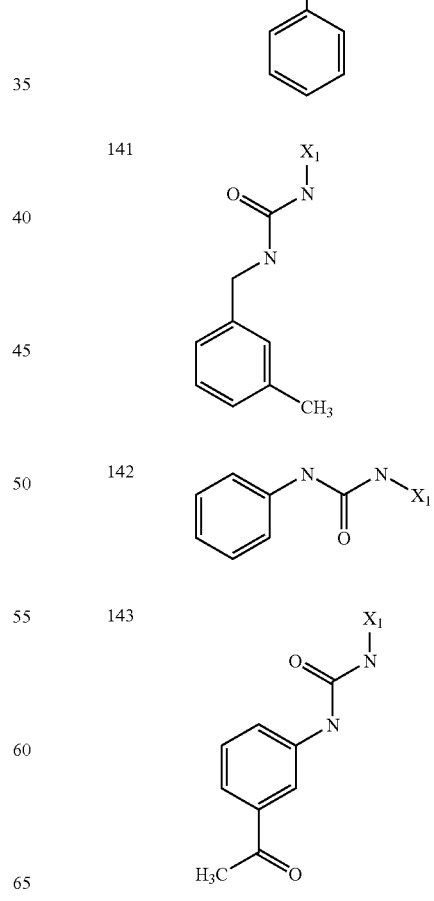 |

TABLE II-continued
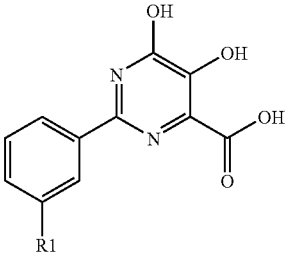
| Ex. No. | R1 |
|---|---|
| 144 | 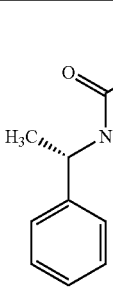 |
| 145 | 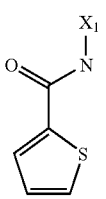 |
| 146 | 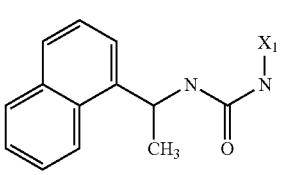 |
| 147 | 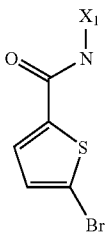 |
| 148 | 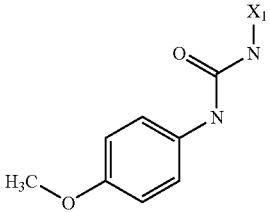 |
TABLE II-continued
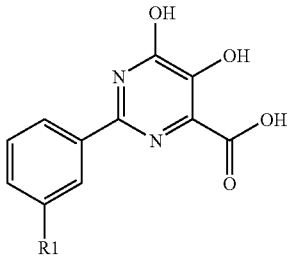
| Ex. No. | R1 |
|---|---|
| 149 | 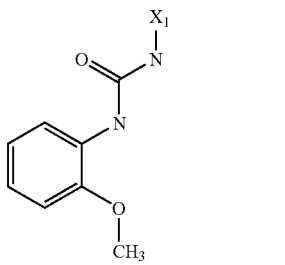 |
| 150 | |
| 151 | |
| 152 | |
| 153 | |

TABLE II-continued
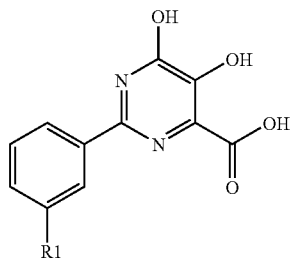
| Ex. No. | R1 |
|---|---|
| 154 |  |
| 155 | 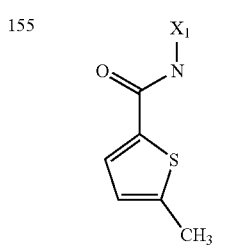 |
| 156 | |
| 157 | 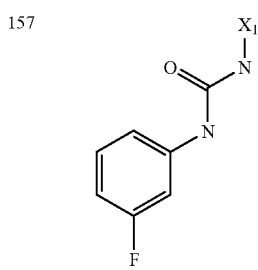 |
TABLE II-continued
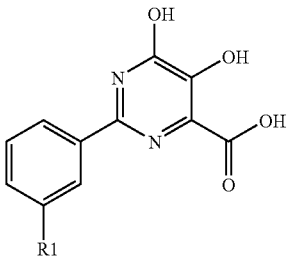
| Ex. No. | R1 |
|---|---|
| 158 | |
| 159 | |
| 160 | 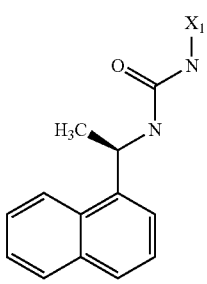 |
| 161 | 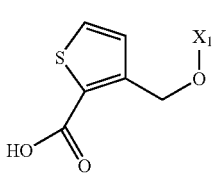 |

TABLE II-continued
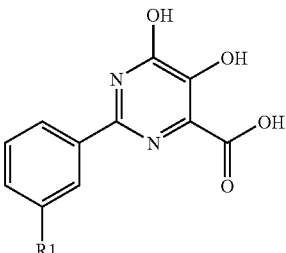
| Ex. No. | R1 |
|---|---|
| 162 | 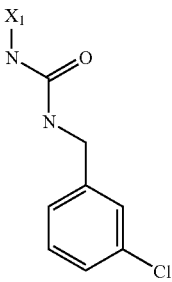 |
| 163 | 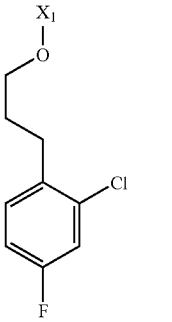 |
| 164 | 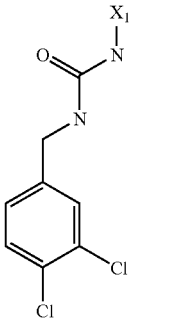 |
| 165 | 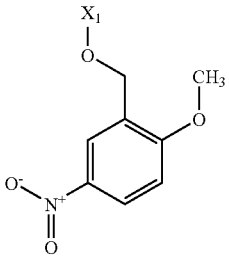 |
TABLE II-continued
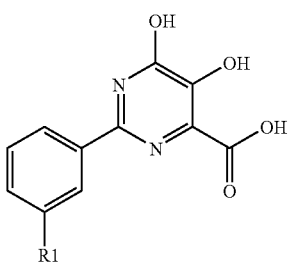
| Ex. No. | R1 |
|---|---|
| 166 | 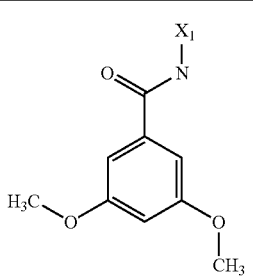 |
| 167 | 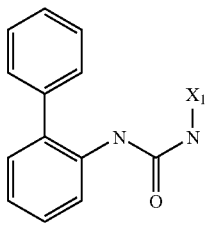 |
| 168 | 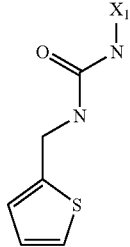 |
| 169 | 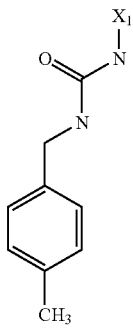 |

TABLE II-continued
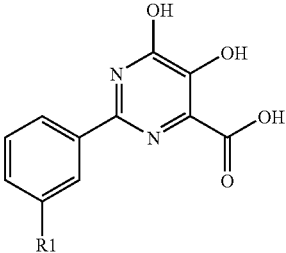
| Ex. No. | R1 |
|---|---|
| 170 | 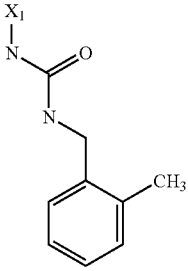 |
| 171 | 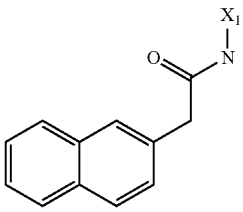 |
| 172 | 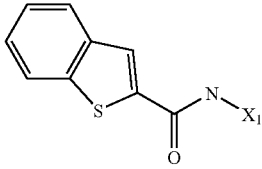 |
| 173 | 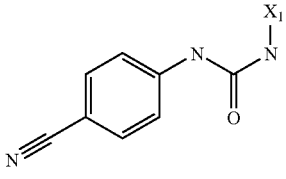 |
| 174 | 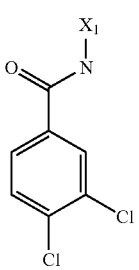 |Нажатие
TABLE II-continued
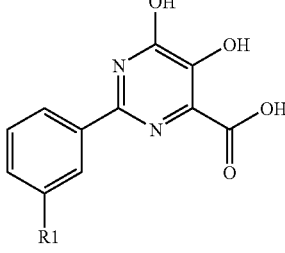
| Ex. No. | R1 |
|---|---|
| 175 | 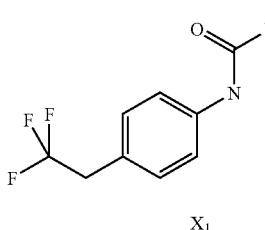 |
| 176 | 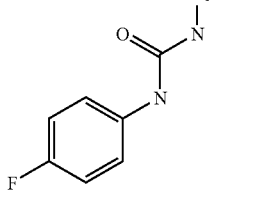 |
| 177 | 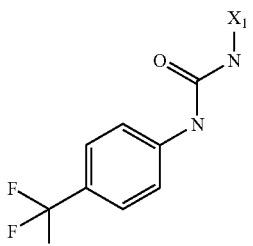 |
| 178 | 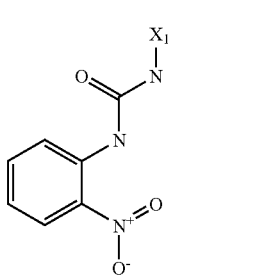 |
| 179 | 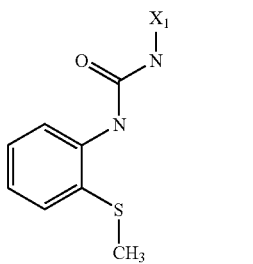 |

TABLE II-continued
| Ex. No. | R1 |
|---|---|
| 180 | 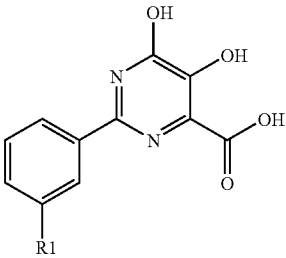 |
| 181 | 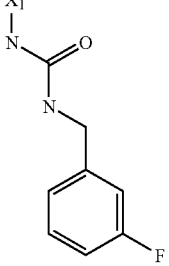 |
| 182 | 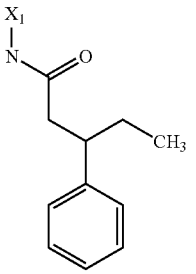 |
| 183 | 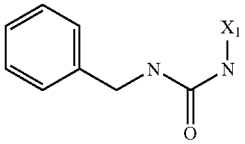 |
| 184 | 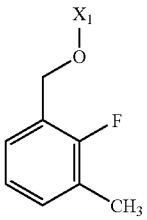 |
| 185 |  |
| 186 | 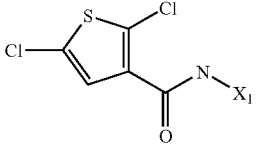 |
| 187 | 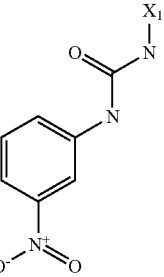 |
| 188 | 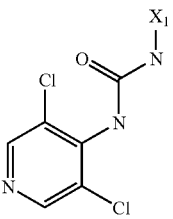 |
| 189 | 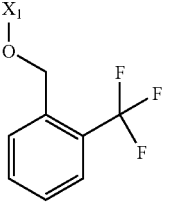 |
| 190 | 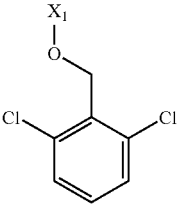 |

TABLE II-continued

![Structure with R1 on phenyl ring attached to pyrimidine with OH, OH, and COOH groups]

| Ex. No. | R1 |
|---------|-----|
| 191 | 3-phenyl-butanamide with X1 (H3C stereochemistry) |
| 192 | 2-(trifluoromethoxy)benzyl urea with X1 |
| 193 | 4-fluoro-3-nitrophenyl urea with X1 |
| 194 | naphthalen-1-yl urea with X1 |
| 195 | thiophen-2-yl acetamide with X1 |
| 196 | m-tolyl urea with X1 |
| 197 | 1,2-diphenylethyl urea with X1 |
| 198 | 1-benzylpiperidin-4-yl urea with X1 |
| 199 | benzyl amide with X1 |
| 200 | 2,3-dihydro-1H-inden-1-yl urea with X1 |

TABLE II-continued
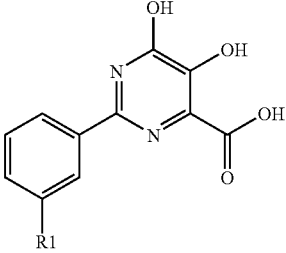
| Ex. No. | R1 |
|---|---|
| 201 | 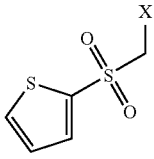 |
| 202 | 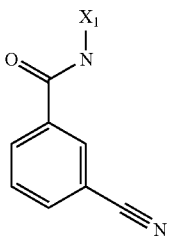 |
| 203 |  |
| 204 | 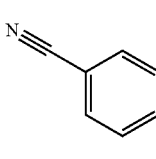 |
| 205 | 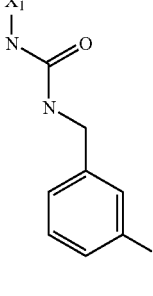 |
| 206 | 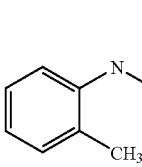 |
TABLE II-continued
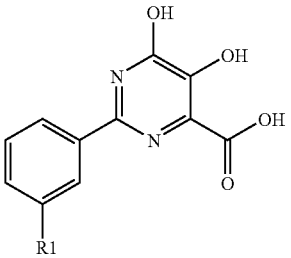
| Ex. No. | R1 |
|---|---|
| 207 | 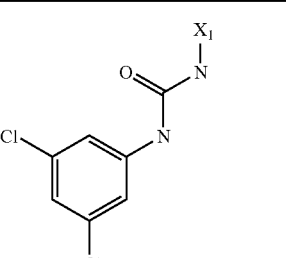 |
| 208 | 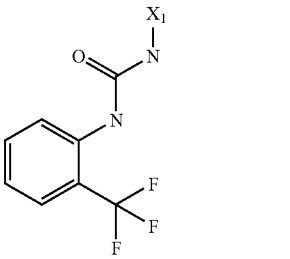 |
| 209 | 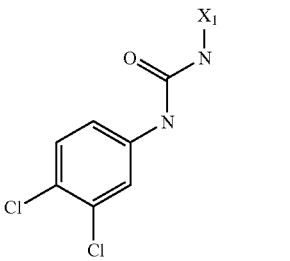 |
| 210 | 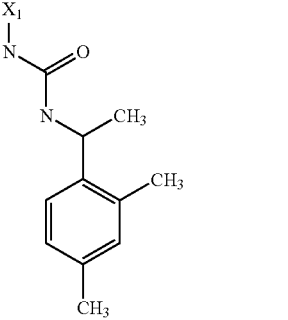 |

TABLE II-continued
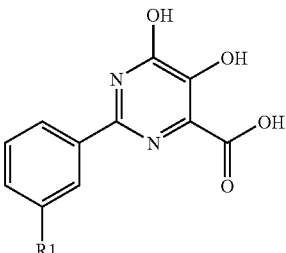
| Ex. No. | R1 |
|---|---|
| 211 | 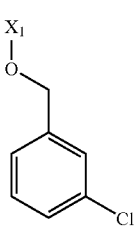 |
| 212 | 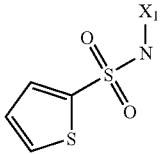 |
| 213 | 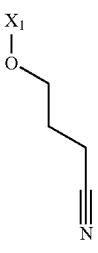 |
| 214 | 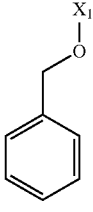 |
| 215 | 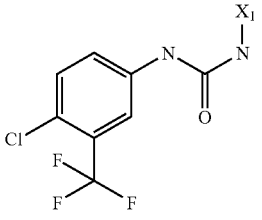 |
TABLE II-continued
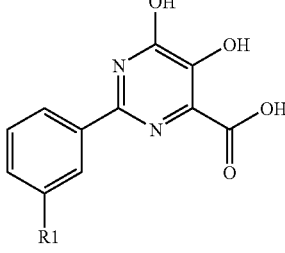
| Ex. No. | R1 |
|---|---|
| 216 | 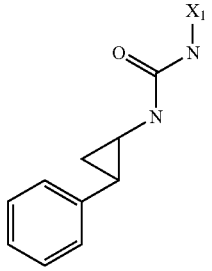 |
| 217 | 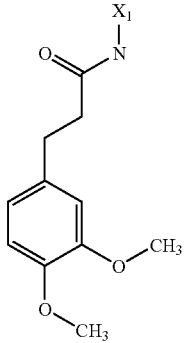 |
| 218 | 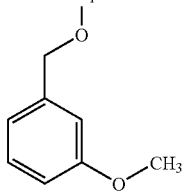 |
| 219 | 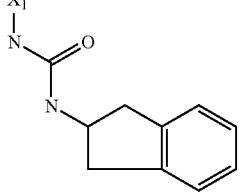 |
| 220 | 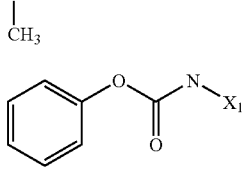 |
| 221 | 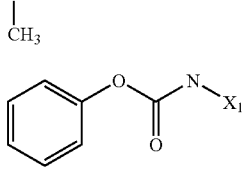 |

TABLE II-continued
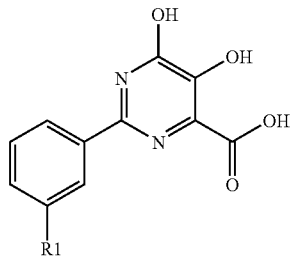
| Ex. No. | R1 |
|---|---|
| 222 |  |
| 223 | H₂N—X₁ |
| 224 | H₃C—O—X₁ |
| 225 | 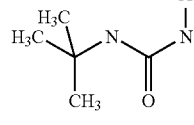 |
| 226 | 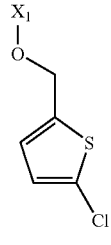 |
| 227 | 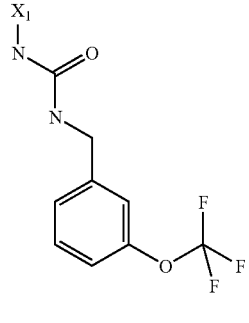 |
TABLE II-continued
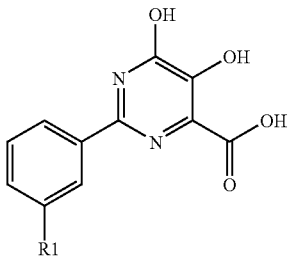
| Ex. No. | R1 |
|---|---|
| 228 | 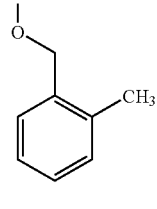 |
| 229 | 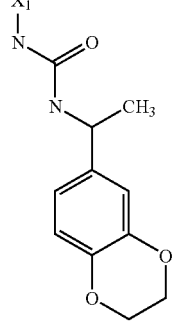 |
| 230 | |
| 231 | |
| 232 | |

TABLE II-continued

[Structure: 2-(3-R1-phenyl)-5,6-dihydroxy-pyrimidine-4-carboxylic acid]

| Ex. No. | R1 |
|---|---|
| 233 | X₁–CH₂–S–(4-methoxyphenyl) |
| 234 | HO–CH₂–C≡C–X₁ |
| 235 | X₁–CH₂–S–(pyridin-4-yl) |
| 236 | X₁–Cl |
| 237 | X₁–CH₂–S(O)₂–(pyridin-2-yl) |
| 238 | cyclohexyl–NH–C(O)–N(H)–X₁ |
| 239 | X₁–O–CH₂–(4-methoxyphenyl) |
| 240 | X₁–N(H)–C(O)–N(H)–CH(CH₂Ph)(3,4-dimethoxyphenyl) |
| 241 | H₃C–CH(CH₃)–N(H)–C(O)–N(H)–X₁ |
| 242 | X₁–N(H)–C(O)–N(H)–(2,3-dichlorophenyl) |
| 243 | phenyl–S(O)₂–N(H)–X₁ |

TABLE II-continued
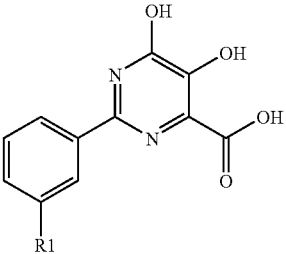
| Ex. No. | R1 |
|---|---|
| 244 | 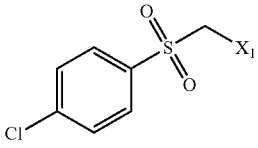 |
| 245 | 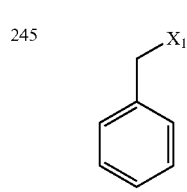 |
| 246 | 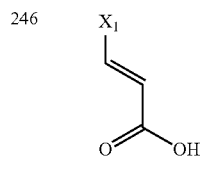 |
| 247 | 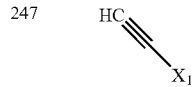 |
TABLE III
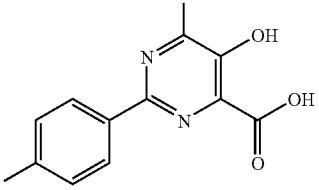
| Ex. No. | R1 |
|---|---|
| 248 | 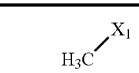 |
| 249 |  |
| 1 (Compound No. 7) | 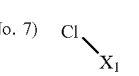 |
TABLE III-continued
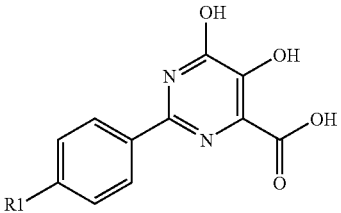
| Ex. No. | R1 |
|---|---|
| 250 | |
| 251 | |
| 252 | |
| 253 | |
TABLE IV
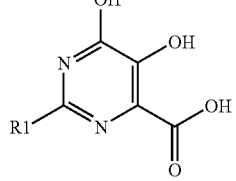
| Ex. No. | R1 |
|---|---|
| 254 | 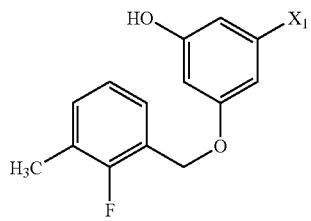 |

TABLE IV-continued
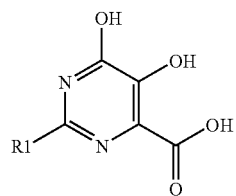
Ex. No.  R1
255 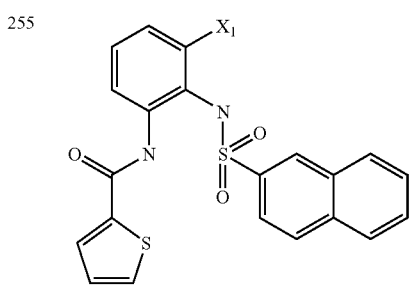
256 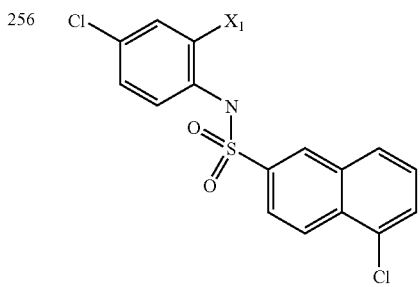
257 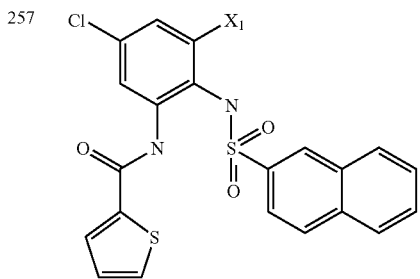
258 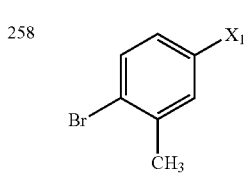
259 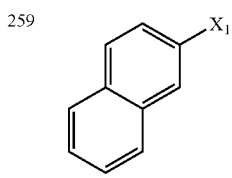
TABLE IV-continued
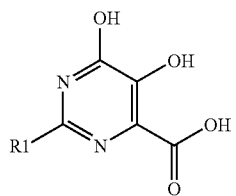
Ex. No.  R1
260 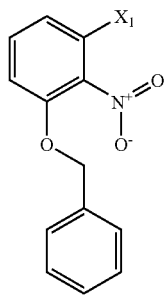
261 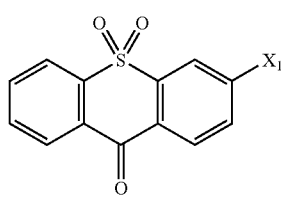
262 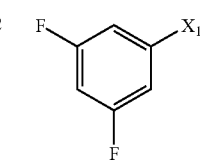
597 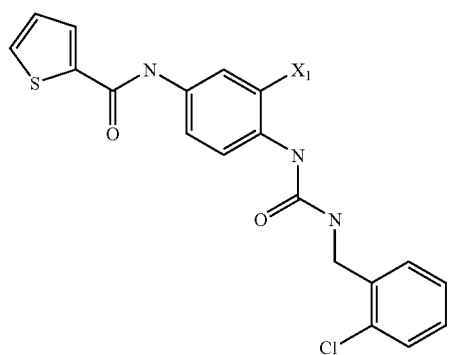

TABLE V

| Ex. No. | Structure |
|---|---|
| 263 | 2-chlorophenylsulfonyl urea derivative |
| 264 | 1-naphthylacetyl derivative |
| 6 (Compound No. 27) | 2-chlorobenzyl urea derivative |
| 265 | (5-chloro-2-nitrobenzyl)oxycarbonyl derivative |
| 266 | (R)-1-phenylethyl urea derivative |

TABLE V-continued

| Ex. No. | Structure |
|---|---|
| 267 | 2-chloro-6-methylbenzyl urea derivative |
| 268 | indol-3-ylacetyl derivative |
| 269 | benzothiophen-3-ylacetyl derivative |
| 270 | 2-chlorobenzyloxycarbonyl derivative |
| 271 | (5-methyl-2-nitrobenzyl)oxycarbonyl derivative |

TABLE V-continued
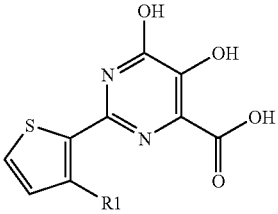
| Ex. No. | |
|---|---|
| 272 | 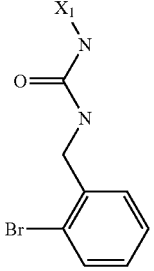 |
| 273 | 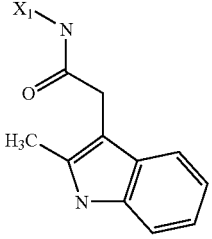 |
| 274 | 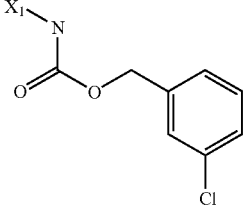 |
| 275 | 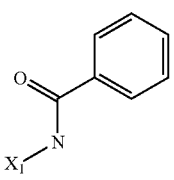 |
| 276 | 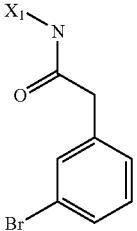 |
TABLE V-continued
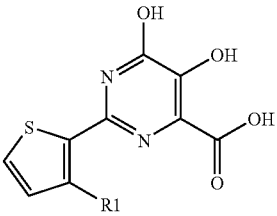
| Ex. No. | |
|---|---|
| 277 | 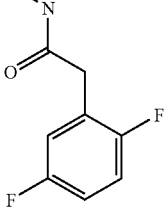 |
| 278 | 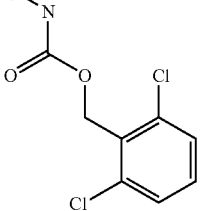 |
| 279 | 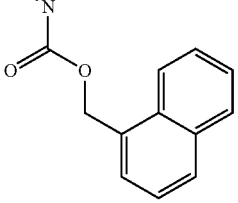 |
| 280 | 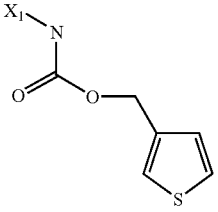 |
| 281 | 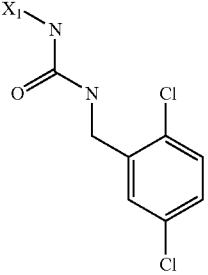 |

TABLE V-continued

| Ex. No. | R1 |
|---|---|
| 282 | benzyl C(O)NH-X₁ |
| 283 | X₁-NH-C(O)-NH-CH₂-(benzothiophen-3-yl) |
| 284 | X₁-NH-C(O)-CH₂-(2-bromophenyl) |
| 285 | benzyl-O-C(O)-NH-X₁ |
| 286 | X₁-NH-C(O)-O-CH₂CH₂-phenyl |
| 287 | X₁-NH-C(O)-CH₂-(4-bromophenyl) |
| 288 | X₁-NH-C(O)-CH₂-(2,4-dichlorophenyl) |
| 289 | X₁-NH-C(O)-O-CH₂-(2,5-dichlorophenyl) |
| 290 | X₁-NH-C(O)-CH₂-(naphthalen-2-yl) |
| 291 | X₁-NH-C(O)-CH₂-(pyridinium-2-yl) |

TABLE V-continued
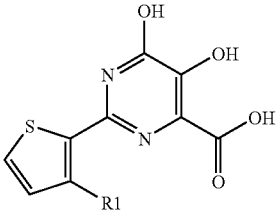
| Ex. No. | |
|---|---|
| 292 | 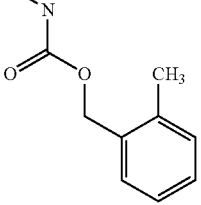 |
| 293 | 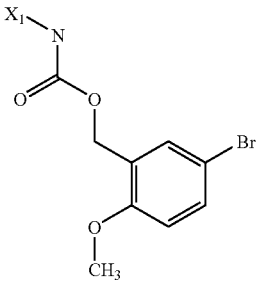 |
| 294 | 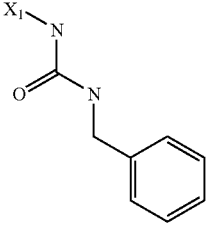 |
| 295 | 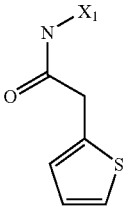 |
| 296 | 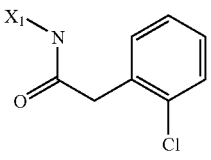 |
| 297 | 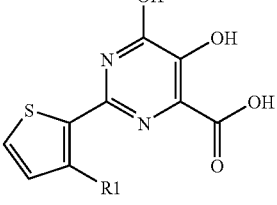 |
| 298 | 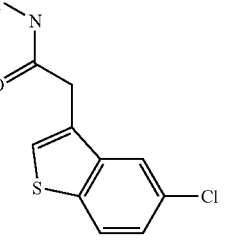 |
| 299 | 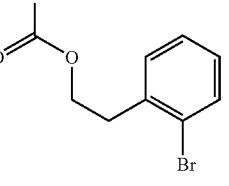 |
| 300 | 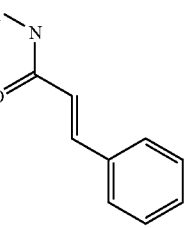 |
| 301 | 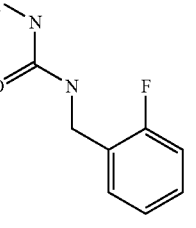 |
| 302 | 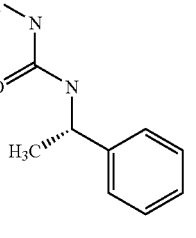 |

TABLE V-continued
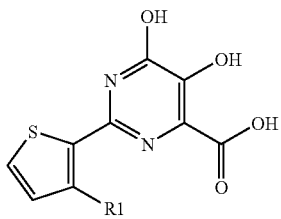
| Ex. No. | |
|---|---|
| 303 | 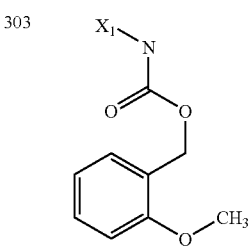 |
| 304 | 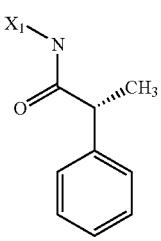 |
| 305 | 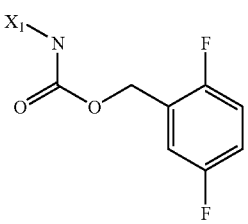 |
| 306 | 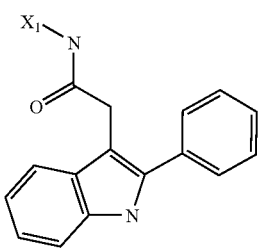 |
| 307 | 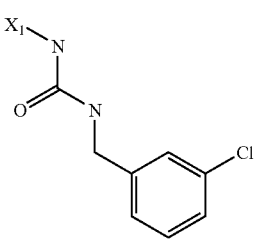 |
TABLE V-continued
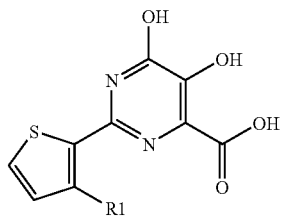
| Ex. No. | |
|---|---|
| 308 | 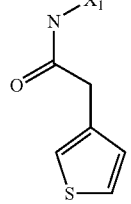 |
| 309 | 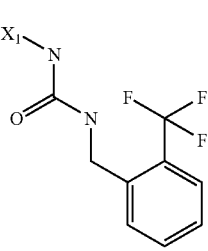 |
| 310 | 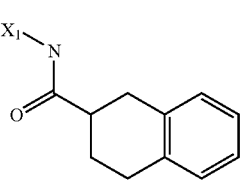 |
| 311 | 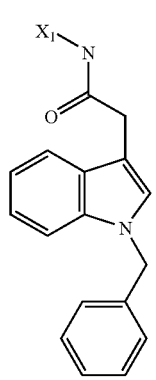 |
| 312 | 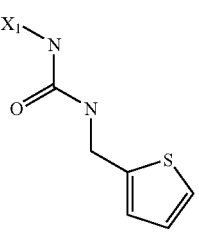 |

TABLE V-continued
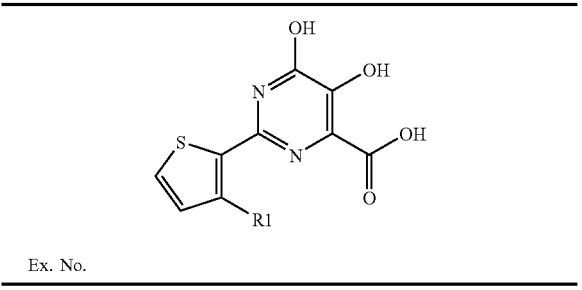
Ex. No.
| 313 | 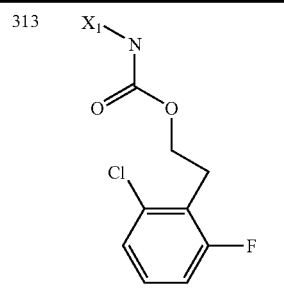 |
| --- | --- |
| 314 | 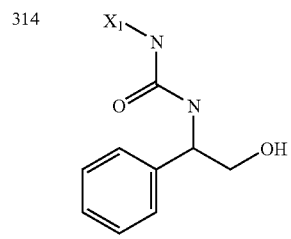 |
| 315 | 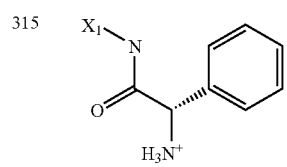 |
| 316 | 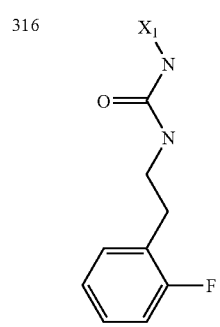 |
| 317 | 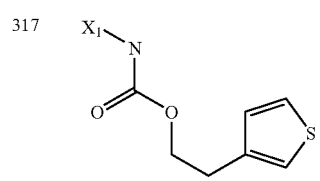 |
| 318 | 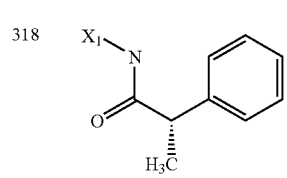 |
TABLE V-continued
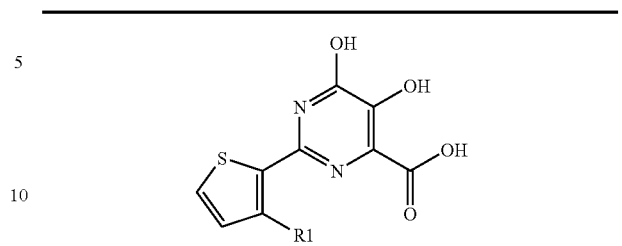
Ex. No.
| 319 | 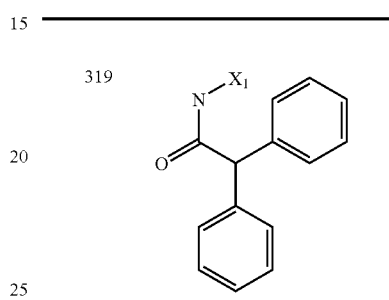 |
| --- | --- |
| 320 | 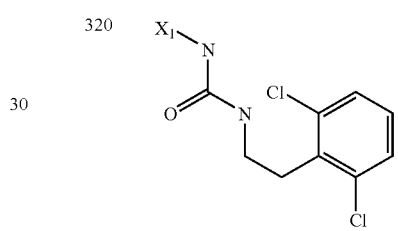 |
| 321 | 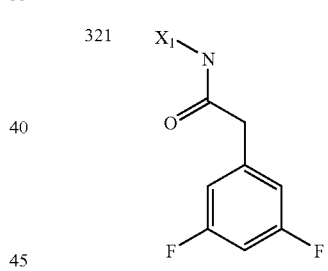 |
| 322 | 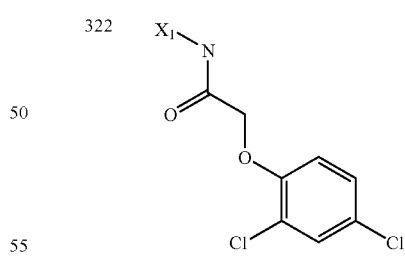 |
| 323 | 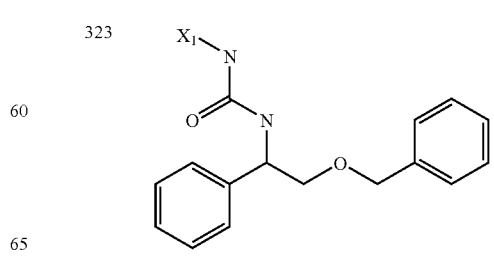 |

TABLE V-continued

[Structure: pyrimidine with OH, OH, COOH groups, linked to thiophene with R1 substituent]

| Ex. No. | R1 |
|---|---|
| 324 | X₁–NH–C(=O)–CH(NH₃⁺)–phenyl (S configuration) |
| 325 | X₁–NH–C(=O)–O–CH₂–(4-methylphenyl) |
| 326 | X₁–NH–C(=O)–O–CH₂–(9H-fluoren-9-yl) |
| 327 | X₁–NH–C(=O)–O–CH(CH₃)–phenyl |
| 328 | X₁–NH–C(=O)–NH–CH₂CH₂–(2-chlorophenyl) |
| 329 | X₁–NH–C(=O)–O–CH₂–(3-methylphenyl) |
| 330 | X₁–NH–C(=O)–O–CH₂–(2-ethoxyphenyl) |
| 331 | X₁–NH–C(=O)–NH–phenyl |
| 332 | X₁–NH–C(=O)–O–CH₂–(3-methoxyphenyl) |
| 333 | X₁–NH–C(=O)–CH₂CH₂–phenyl |

TABLE V-continued
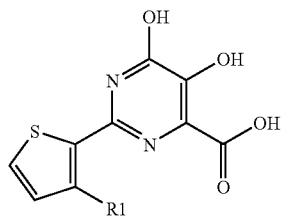
| Ex. No. | |
|---|---|
| 334 | 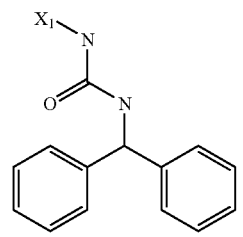 |
| 335 | 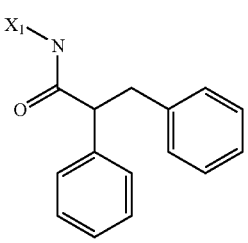 |
| 336 | 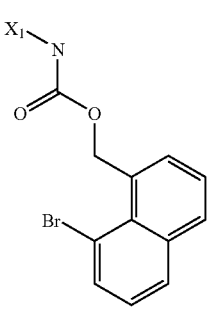 |
| 337 | 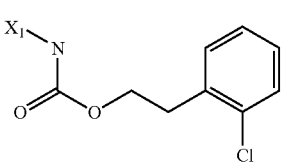 |
| 338 | 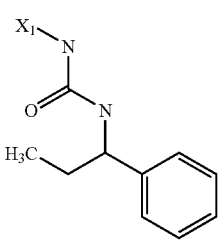 |
TABLE V-continued
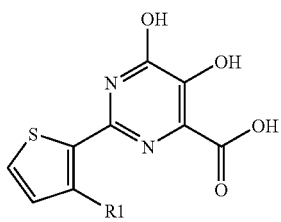
| Ex. No. | |
|---|---|
| 339 | 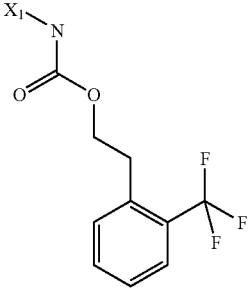 |
| 340 | 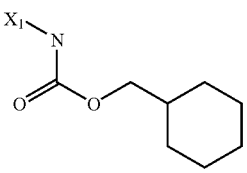 |
| 341 | 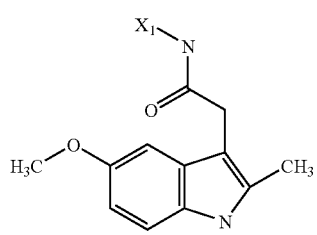 |
| 342 | 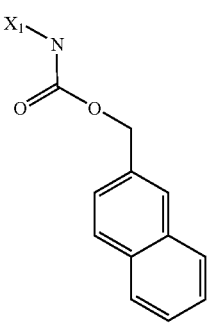 |
| 343 | 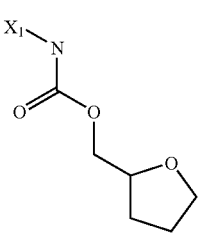 |

TABLE V-continued
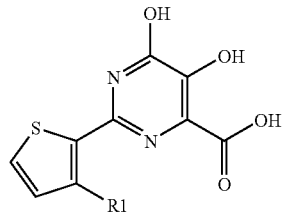
| Ex. No. | |
|---|---|
| 344 |  |
| 345 |  |
| 346 |  |
| 347 |  |
| 348 |  |
TABLE V-continued
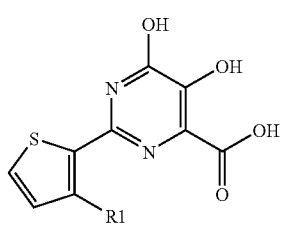
| Ex. No. | |
|---|---|
| 349 |  |
| 350 |  |
| 351 |  |
| 352 |  |
| 353 |  |

TABLE V-continued
| Ex. No. | |
|---|---|
| 354 | 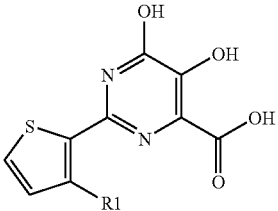 |
| 355 | 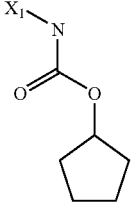 |
| 356 | 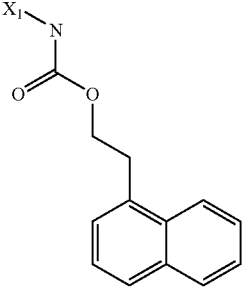 |
| 357 | 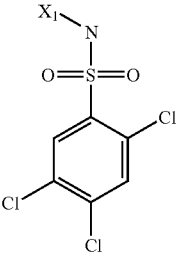 |
| 358 | 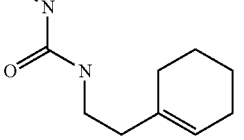 |
| 359 | 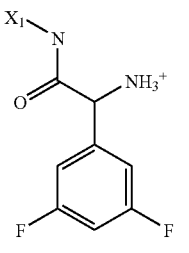 |
| 360 | 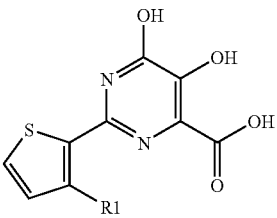 |
| 361 | 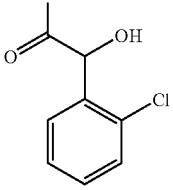 |
| 362 | 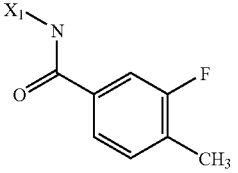 |
| 363 | 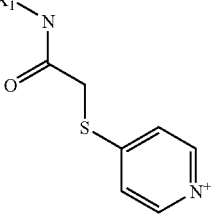 |

TABLE V-continued
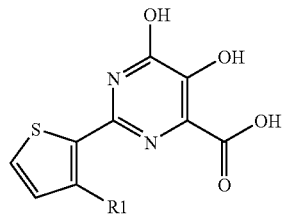
| Ex. No. | |
|---|---|
| 364 | 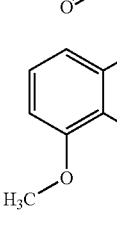 |
| 5 (Compound No. 24) | X₁—H |
| 365 | 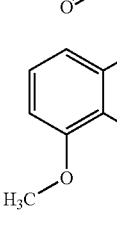 |
| 366 | 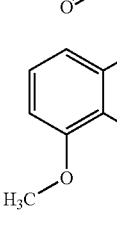 |
| 367 | 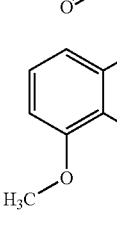 |
| 368 | 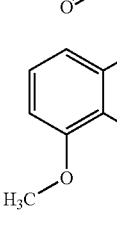 |
TABLE V-continued
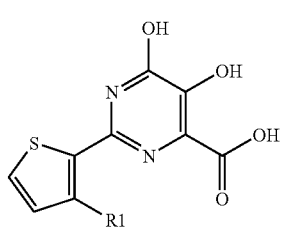
| Ex. No. | |
|---|---|
| 369 | 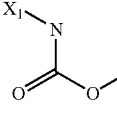 |
| 370 | 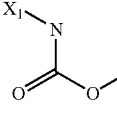 |
| 371 | 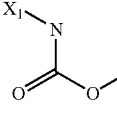 |
| 372 | 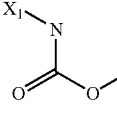 |

TABLE V-continued
| Ex. No. | |
|---|---|
| 373 | 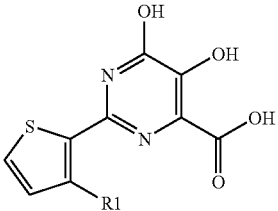 |
| 374 | 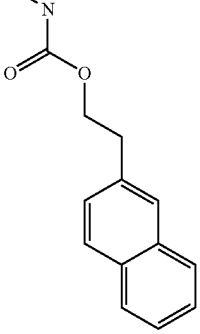 |
| 375 | 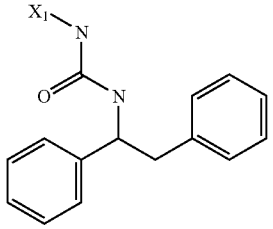 |
| 376 | 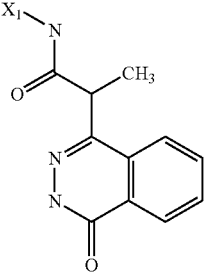 |
| 377 | 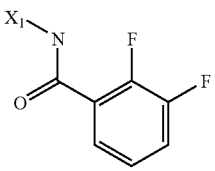 |
| 378 | 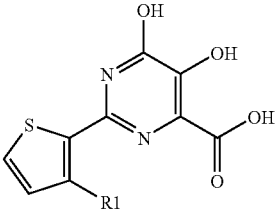 |
| 379 | 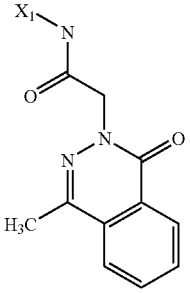 |
| 380 | 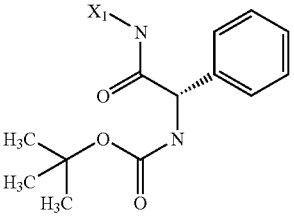 |
| 381 | 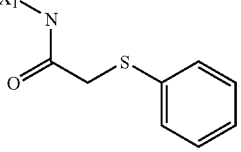 |

TABLE V-continued
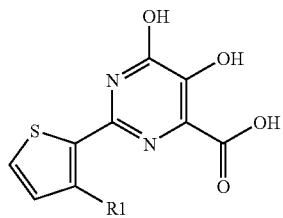
| Ex. No. | |
|---|---|
| 382 | 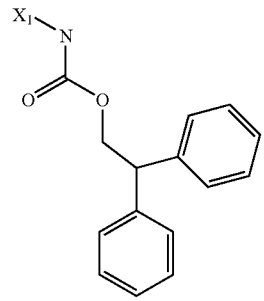 |
| 383 | |
| 384 | 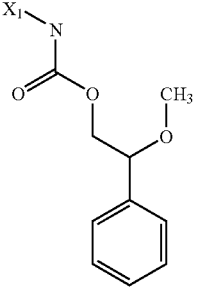 |
| 385 | 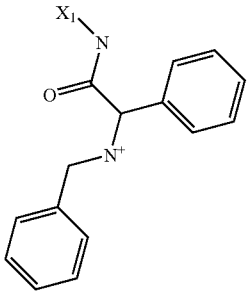 |
|  | 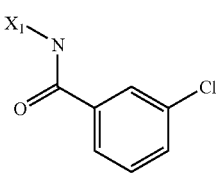 |
TABLE V-continued
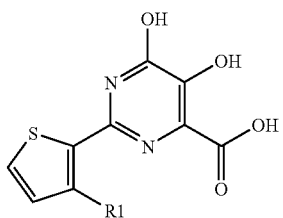
| Ex. No. | |
|---|---|
| 386 | 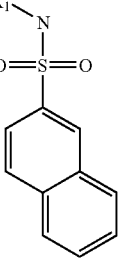 |
| 387 | 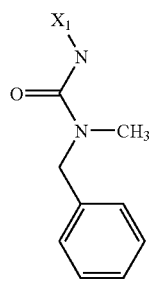 |
| 388 | 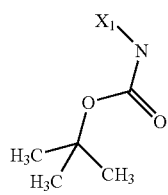 |
| 389 | 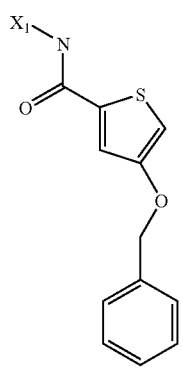 |

TABLE V-continued
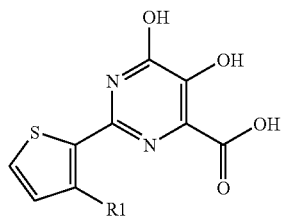
| Ex. No. | |
|---|---|
| 390 | 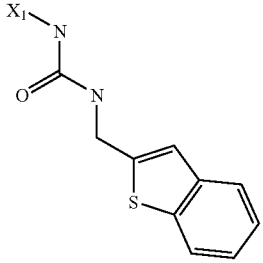 |
| 391 | 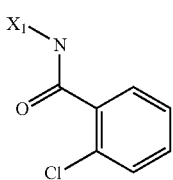 |
| 392 | X1—Br |
| 393 | 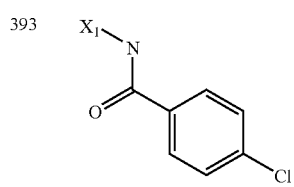 |
| 394 | 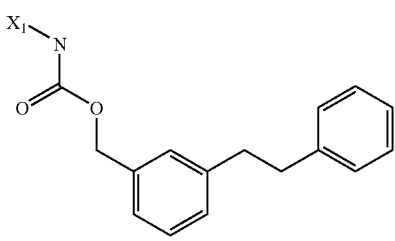 |
| 395 | 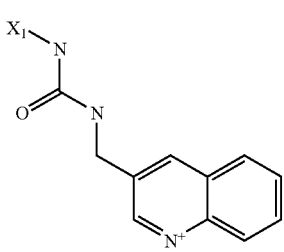 |
TABLE V-continued
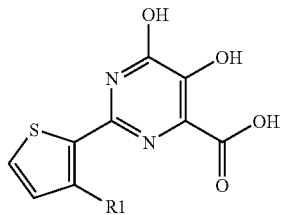
| Ex. No. | |
|---|---|
| 396 | 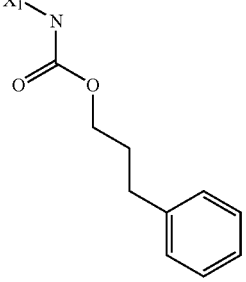 |
| 397 | 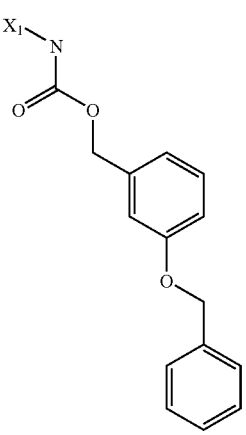 |
| 398 | 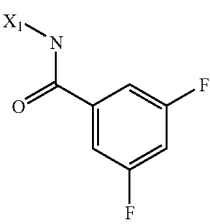 |
| 399 | 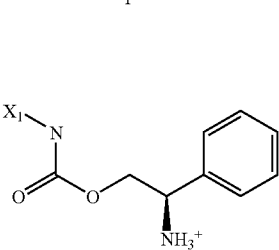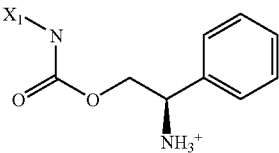 |

TABLE V-continued
| Ex. No. | R1 |
|---|---|
| 400 | 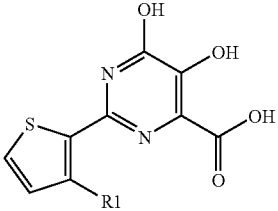 |
| 401 | 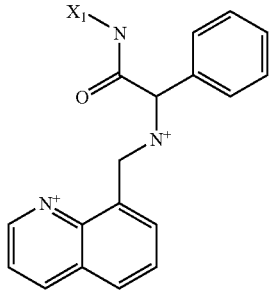 |
| 402 | 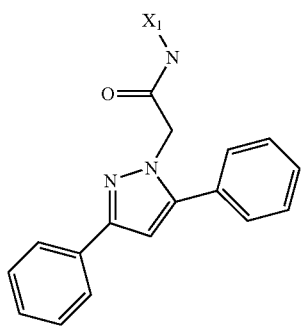 |
| 403 | 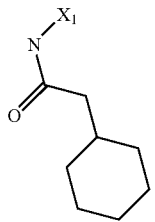 |
| 404 | 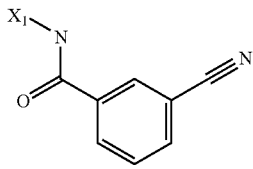 |
| 405 | 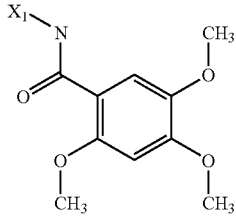 |
| 406 | 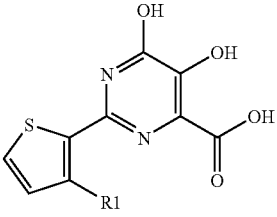 |
| 407 | 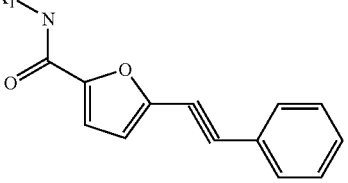 |
| 408 | 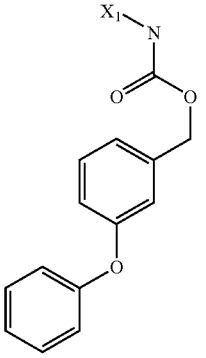 |
| 409 | 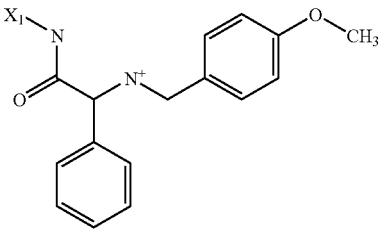 |

TABLE V-continued

[Structure: pyrimidine with OH, OH, COOH substituents, connected to thiophene bearing R1]

| Ex. No. | R1 |
|---|---|
| 410 | X₁–NH₃⁺ |
| 411 | X₁–NH–C(O)–O–CH₂–CH(Ph)–NH–C(O)–O–C(CH₃)₃ |
| 412 | X₁–NH–C(O)–(tetrahydroisoquinolinium) |
| 413 | X₁–NH–C(O)–CH(Ph)–N⁺H–CH₂–CH(CH₃)₂ |
| 414 | X₁–NH–C(O)–CH₂–CH₂–cyclopentyl |
| 415 | X₁–NH–C(O)–(2,2,3,3-tetramethylcyclopropyl) |
| 416 | X₁–NH–C(O)–O–CH₂–CH(Ph)–NH–C(O)–O–C(CH₃)₃ |
| 417 | X₁–NH–C(O)–CH₂–NH–Ph |
| 418 | X₁–NH–C(O)–(2,2-dimethyl-3-(2-methylpropenyl)cyclopropyl) |
| 419 | X₁–NH–C(O)–C(Ph)(Ph)–NH₃⁺ |
| 420 | X₁–NH–C(O)–CH₂–N(4-phenyl-2-oxopyrrolidinyl) |

TABLE V-continued
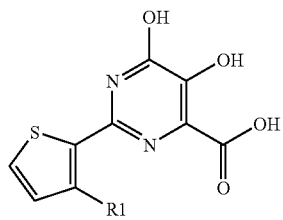
| Ex. No. | |
|---|---|
| 421 | 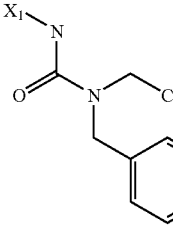 |
| 422 | 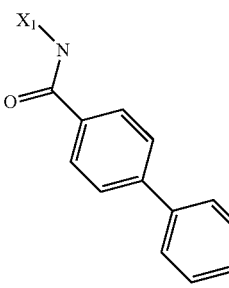 |
| 423 | 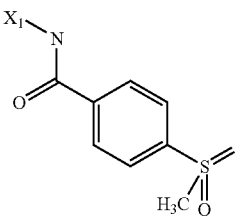 |
| 424 | 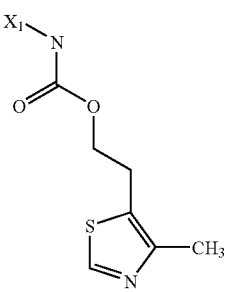 |
| 425 | 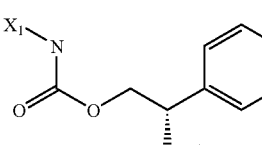 |
TABLE V-continued
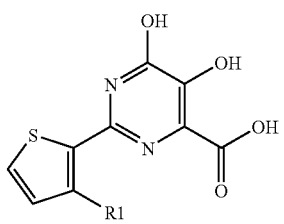
| Ex. No. | |
|---|---|
| 426 | 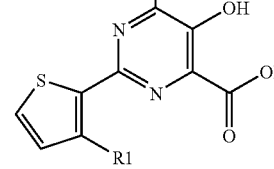 |
| 427 | 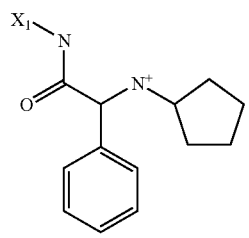 |
| 428 | 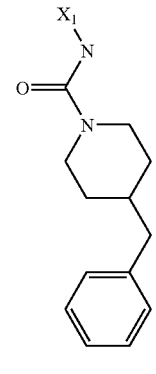 |
| 429 | 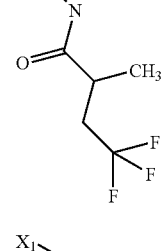 |
| 430 | 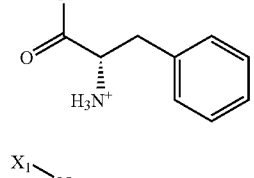 |
| 431 | 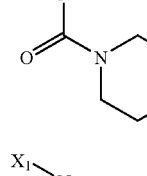 |

TABLE V-continued
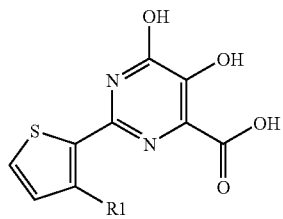
| Ex. No. | |
|---|---|
| 432 | 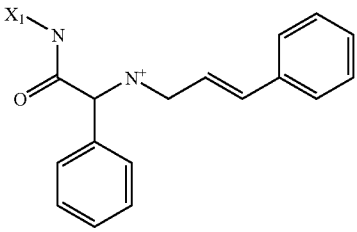 |
| 433 | 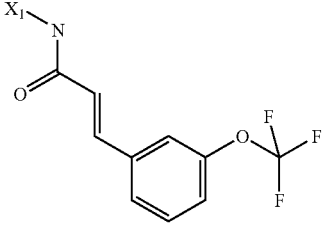 |
| 434 | 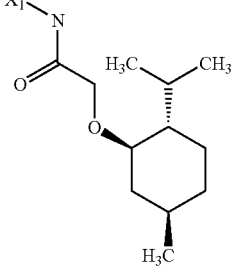 |
| 435 | 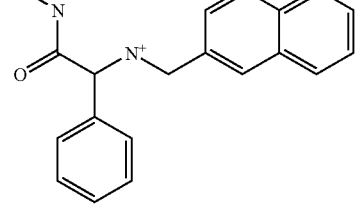 |
| 436 | 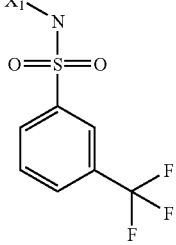 |
TABLE V-continued
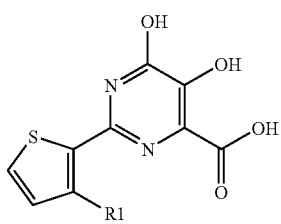
| Ex. No. | |
|---|---|
| 437 | 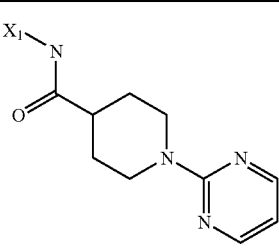 |
| 438 | 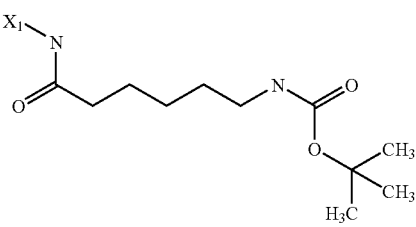 |
| 439 | 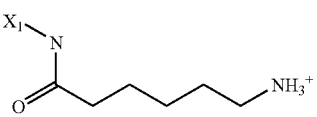 |
| 440 | 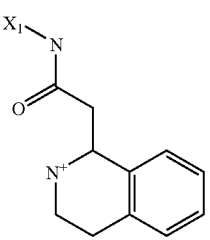 |
| 441 | 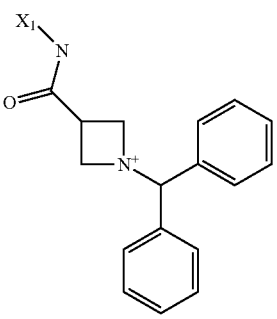 |
| 442 | 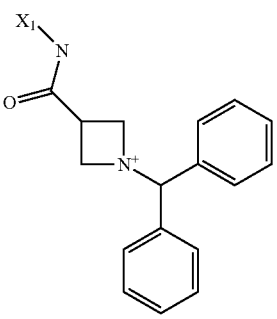 |

TABLE V-continued
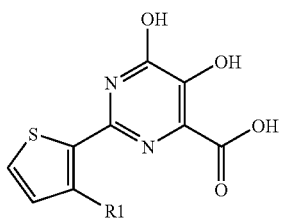
| Ex. No. | |
|---|---|
| 449 | 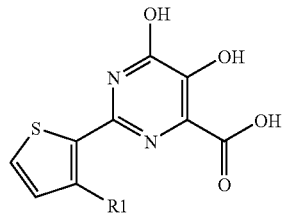 |
| 450 | 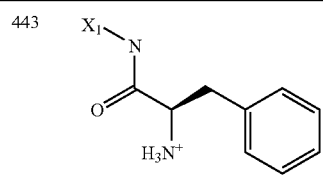 |
| 451 | 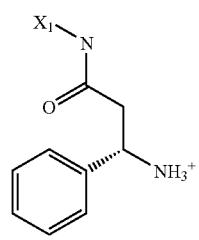 |
| 452 | 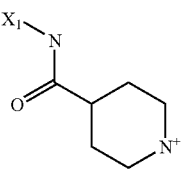 |
| 453 | 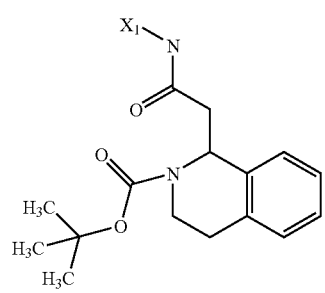 |

TABLE V-continued
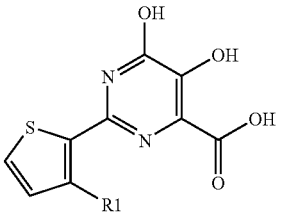

TABLE V-continued
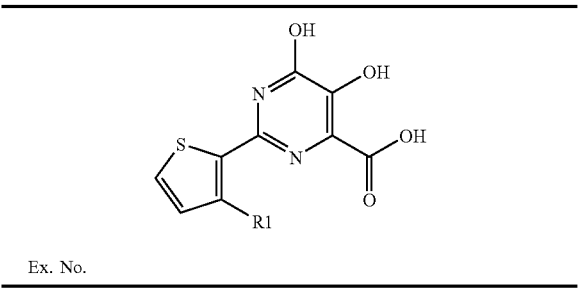
| Ex. No. | |
|---|---|
| 607 | 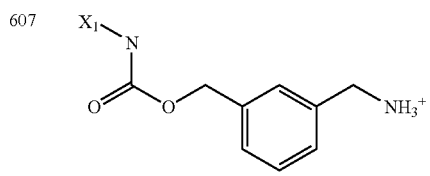 |
| 608 | 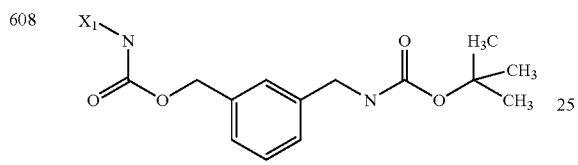 |
| 609 | 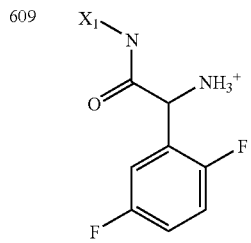 |
| 610 | 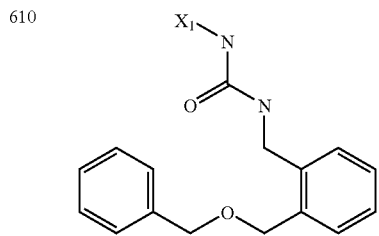 |
| 611 | 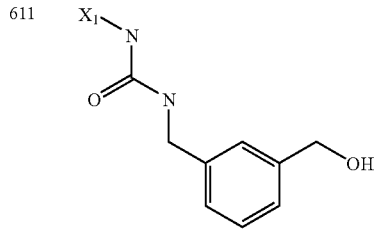 |
| 612 | 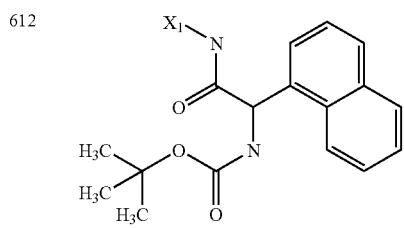 |
TABLE V-continued
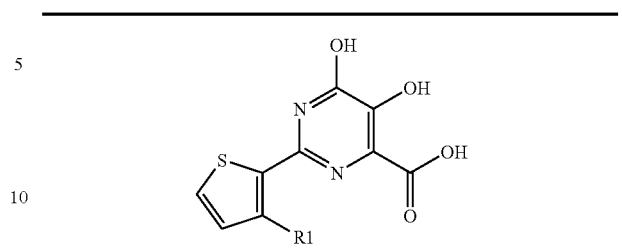
| Ex. No. | |
|---|---|
| 613 | 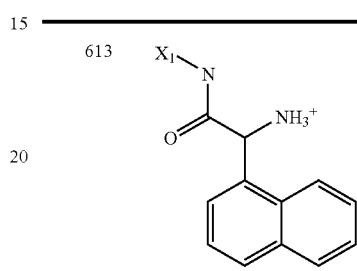 |
| 614 | 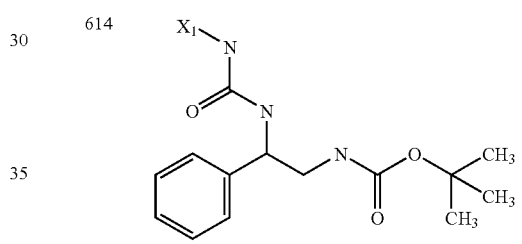 |
| 615 | 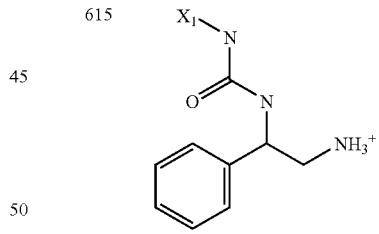 |
| 616 | 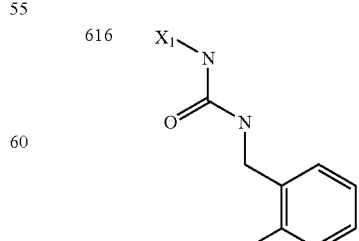 |

TABLE V-continued
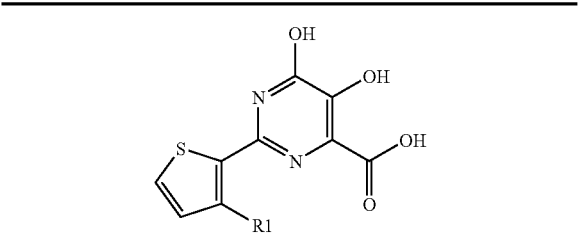
| Ex. No. | |
|---|---|
| 617 | 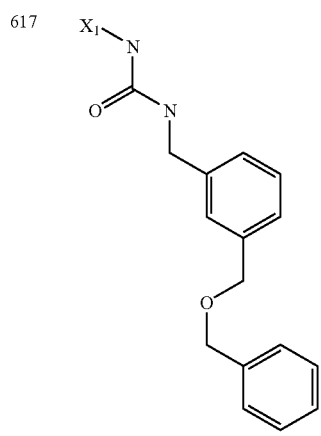 |
| 618 | 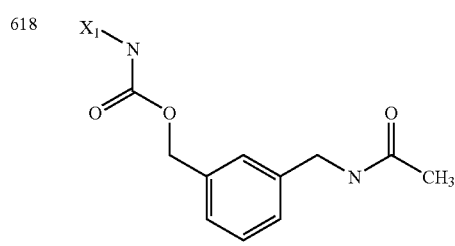 |
| 619 | 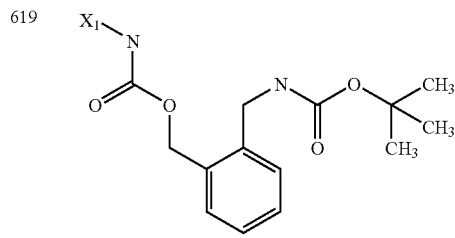 |
| 620 | 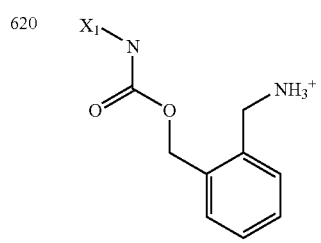 |
TABLE V-continued
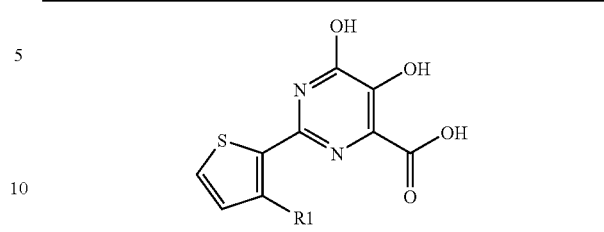
| Ex. No. | |
|---|---|
| 621 | 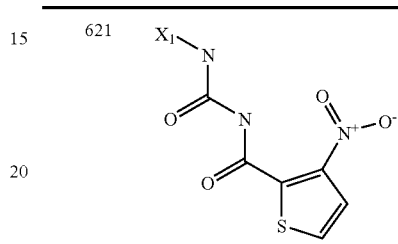 |
| 622 | 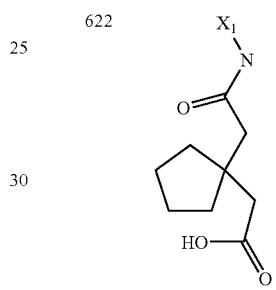 |
| 623 | 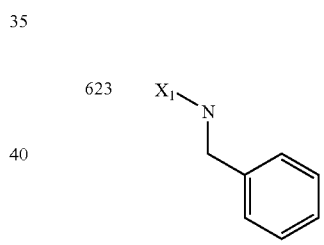 |
| 624 | 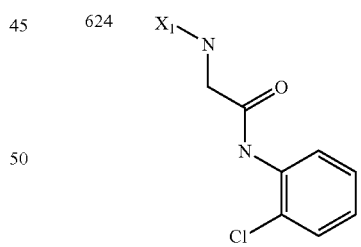 |
| 625 | 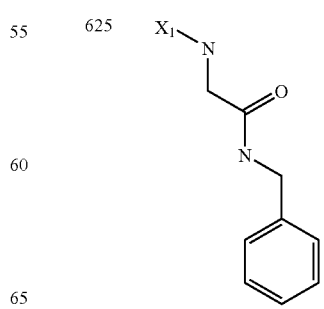 |

TABLE V-continued
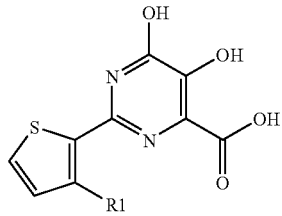
| Ex. No. | |
|---|---|
| 626 | 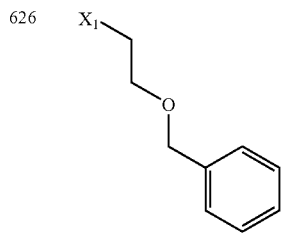 |
| 627 | 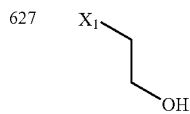 |
| 9 (Compound No. 628) | 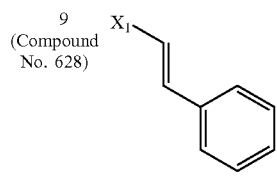 |
TABLE VI
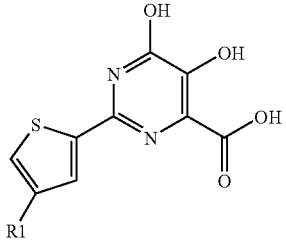
| Ex. No. | R1 |
|---|---|
| 454 |  |
| 455 | 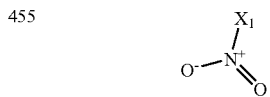 |
| 456 | 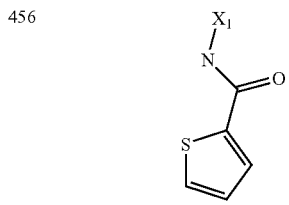 |
TABLE VI-continued
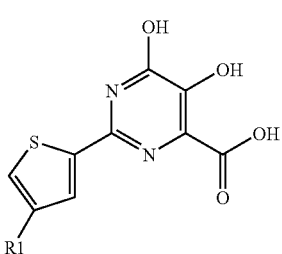
| Ex. No. | R1 |
|---|---|
| 457 | 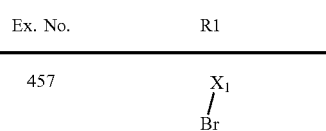 |
| 458 | 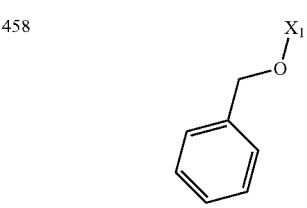 |
TABLE VIIa
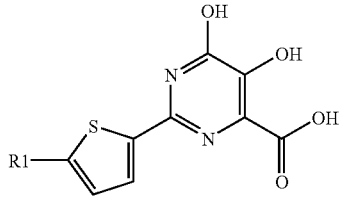
| Ex. No. | R1 |
|---|---|
| 459 | 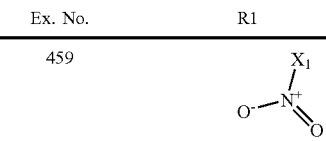 |
| 460 | 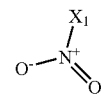 |
| 461 | 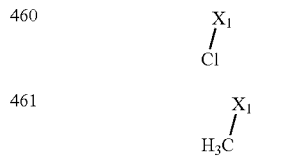 |
TABLE VIIb
| 462 | 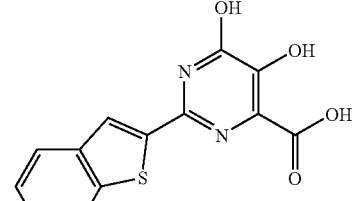 |
|---|---|

TABLE VIII

| Ex. No. | R1 |
|---|---|
| 463 | 2-chlorophenylsulfonyl urea |
| 464 | 2-methylphenylsulfonyl urea |
| 465 | phenylsulfonyl urea |
| 466 | 4-methylphenylsulfonyl urea |
| 467 | 4-fluorophenylsulfonyl urea |

TABLE VIII-continued

| Ex. No. | R1 |
|---|---|
| 7 (Compound No. 36) | 2-chlorobenzyl urea |
| 469 | benzyloxycarbonyl |
| 470 | 2-fluorobenzyl urea |
| 471 | 2-chlorobenzyloxycarbonyl |
| 472 | benzothiophen-3-ylmethyl urea |

TABLE VIII-continued
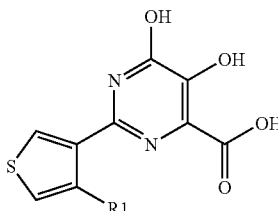
| Ex. No. | R1 |
|---|---|
| 473 | 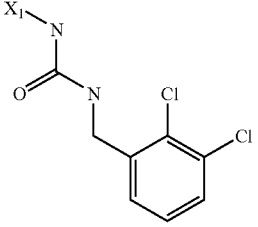 |
| 474 | 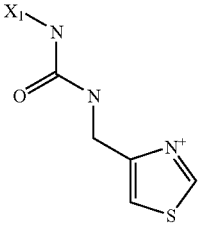 |
| 475 | 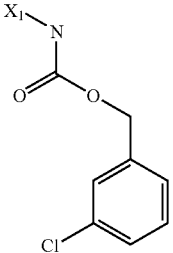 |
| 476 | 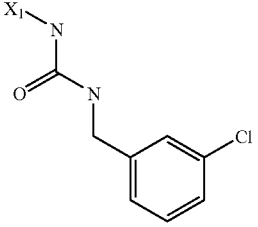 |
| 477 | 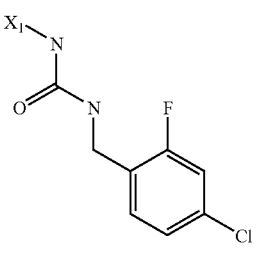 |
TABLE VIII-continued
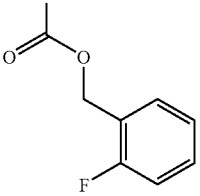
| Ex. No. | R1 |
|---|---|
| 478 | 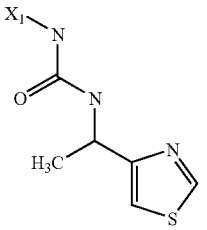 |
| 479 | 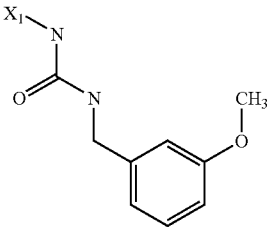 |
| 480 | 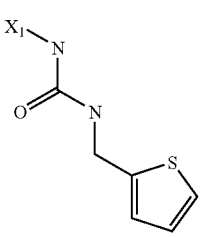 |
| 481 | 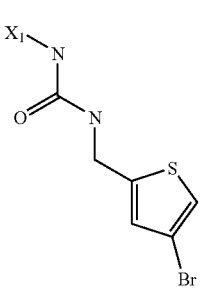 |
| 482 | 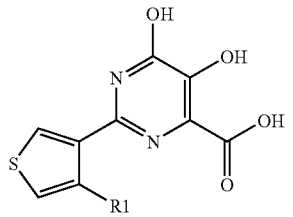 |

TABLE VIII-continued
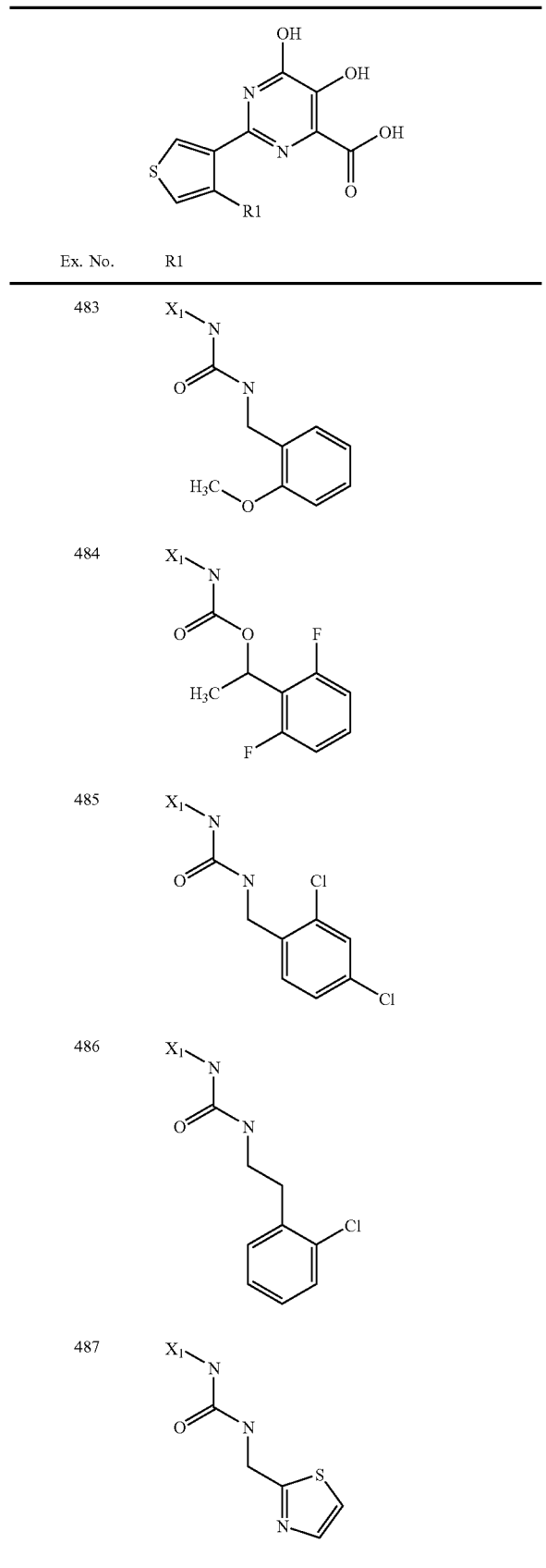
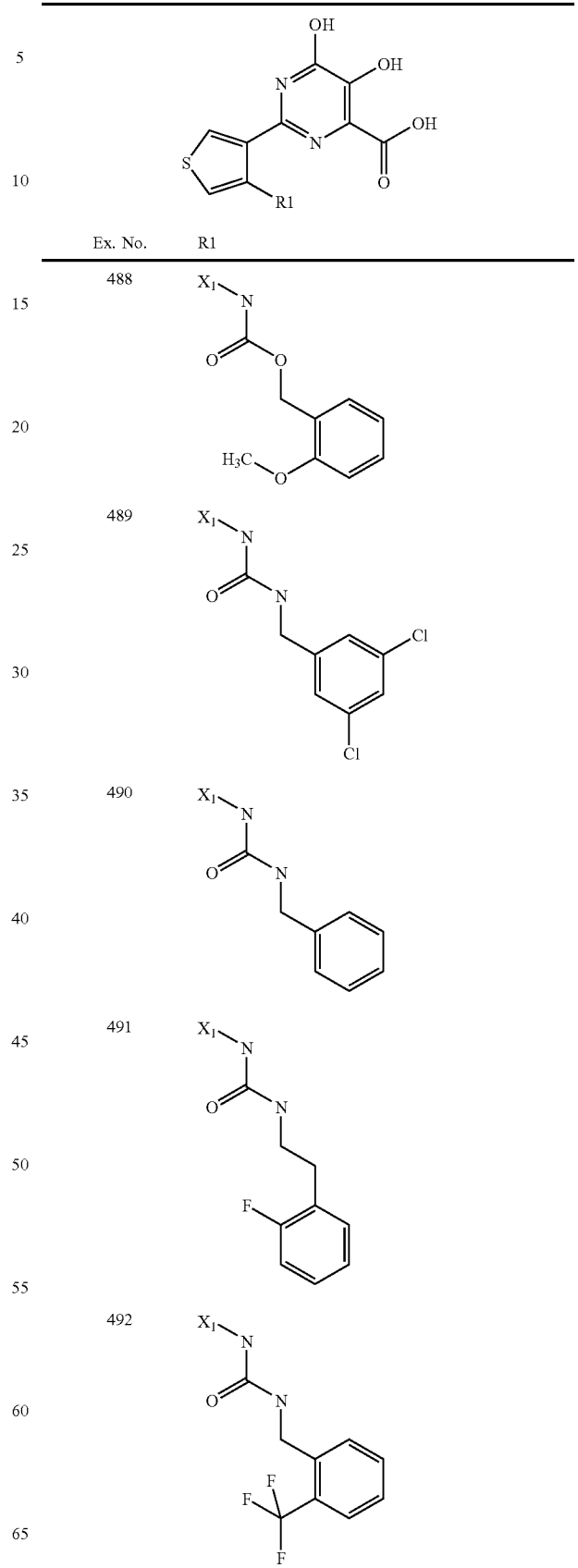

TABLE VIII-continued

[Structure: 2-thiophenyl-pyrimidine with OH, OH, and COOH substituents; R1 on thiophene]

| Ex. No. | R1 |
|---|---|
| 493 | X₁-NH-C(O)-N(H)-phenyl |
| 494 | X₁-NH-C(O)-N(H)-(2-fluorophenyl) |
| 495 | X₁-NH-C(O)-CH₂-(benzothiophen-3-yl) |
| 496 | X₁-NH-C(O)-N(H)-(3-methylphenyl) |
| 497 | X₁-NH-C(O)-N(H)-CH₂-(isoxazol-3-yl) |
| 498 | X₁-NH-C(O)-N(H)-CH(CH₃)-(furan-3-yl) |
| 499 | X₁-NH-C(O)-N(H)-CH₂-(furan-3-yl) |
| 500 | X₁-NH-C(O)-N(H)-CH(phenyl)-CH₂OH |
| 501 | X₁-NH-C(O)-N(H)-CH(phenyl)-CH₂-phenyl |
| 502 | X₁-NH-C(O)-N(H)-(3-methoxyphenyl) |

TABLE VIII-continued
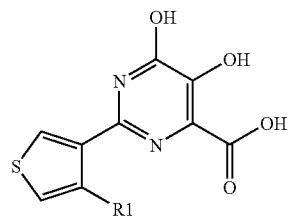
| Ex. No. | R1 |
|---|---|
| 503 |  |
| 504 |  |
| 505 |  |
| 506 |  |
| 507 |  |
TABLE VIII-continued
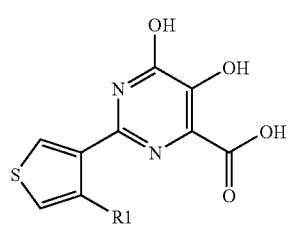
| Ex. No. | R1 |
|---|---|
| 508 |  |
| 509 |  |
| 510 |  |
| 511 |  |

TABLE VIII-continued
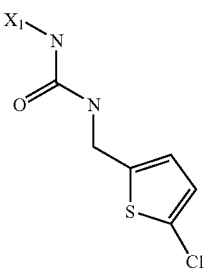
| Ex. No. | R1 |
|---|---|
| 512 | 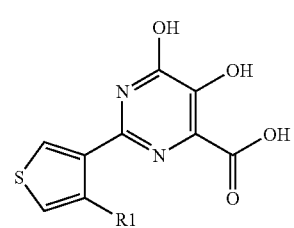 |
| 513 | 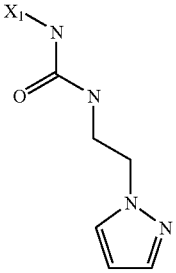 |
| 514 | 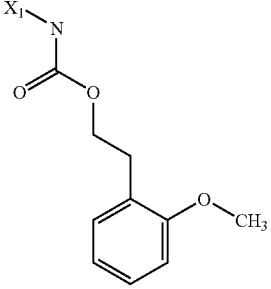 |
| 515 | 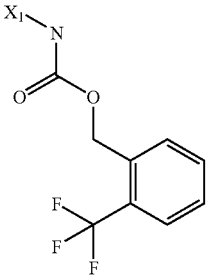 |
TABLE VIII-continued
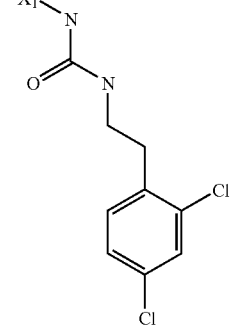
| Ex. No. | R1 |
|---|---|
| 516 | 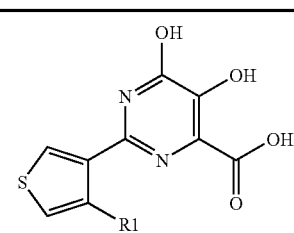 |
| 517 | 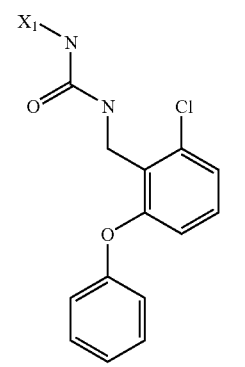 |
| 518 | 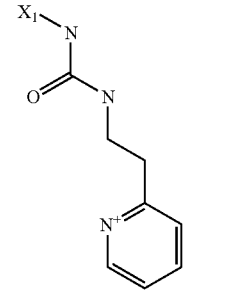 |
| 519 | 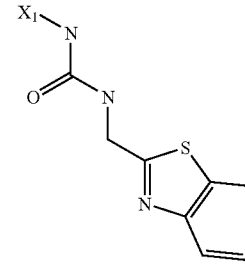 |

TABLE VIII-continued
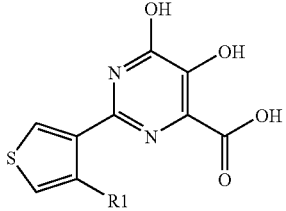
| Ex. No. | R1 |
|---|---|
| 520 | 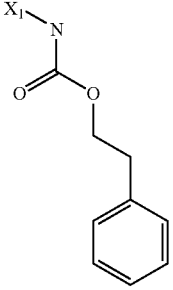 |
| 521 | 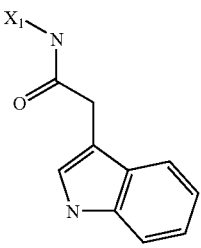 |
| 522 | 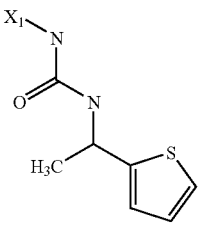 |
| 523 | 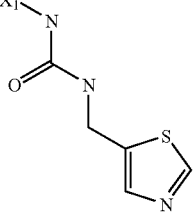 |
| 524 | 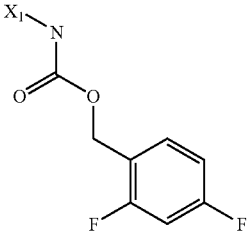 |
TABLE VIII-continued
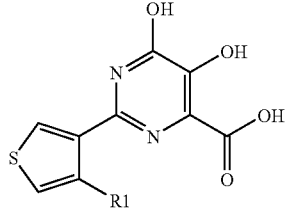
| Ex. No. | R1 |
|---|---|
| 525 | 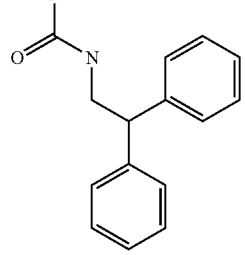 |
| 526 | 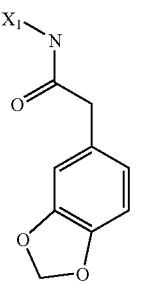 |
| 527 | 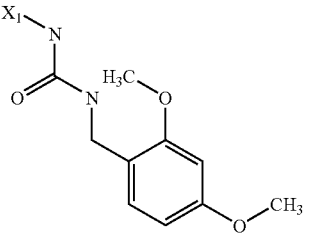 |
| 528 | 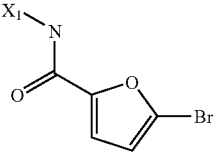 |
| 529 | 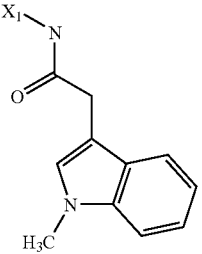 |

TABLE VIII-continued
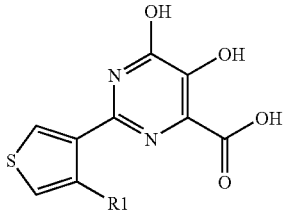
| Ex. No. | R1 |
|---|---|
| 530 | 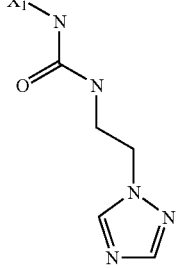 |
| 531 | 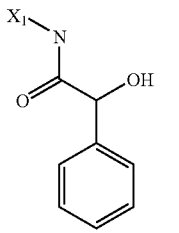 |
| 532 | 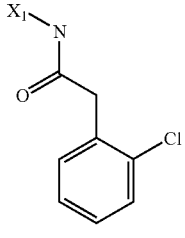 |
| 533 | 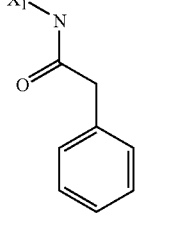 |
| 534 | 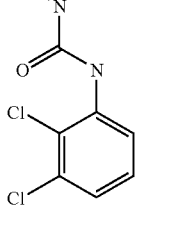 |
TABLE VIII-continued
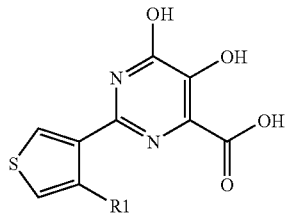
| Ex. No. | R1 |
|---|---|
| 535 | 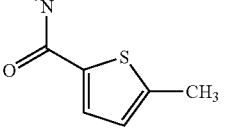 |
| 536 | 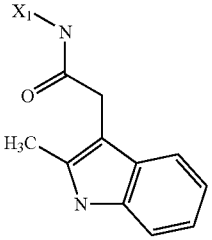 |
| 537 | 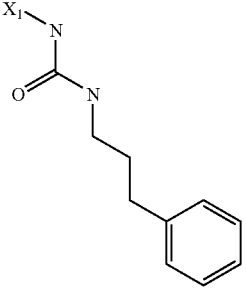 |
| 538 | 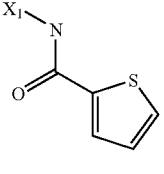 |
| 539 | 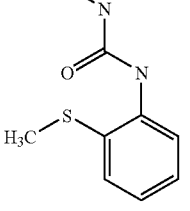 |

TABLE VIII-continued
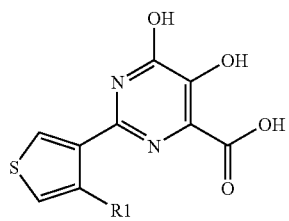
| Ex. No. | R1 |
|---|---|
| 540 | |
| 541 | X₁—H |
| 542 | |
| 543 | |
| 544 |  |
TABLE VIII-continued
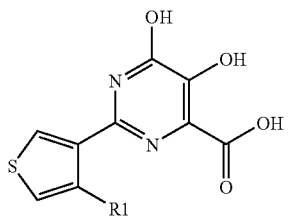
| Ex. No. | R1 |
|---|---|
| 545 | |
| 546 | |
| 547 | |
| 548 | |

TABLE VIII-continued

[Structure: pyrimidine with OH, OH, COOH substituents connected to thiophene bearing R1]

| Ex. No. | R1 |
|---------|-----|
| 549 | X₁–NH₃⁺ |
| 550 | X₁–NH–C(O)–NH–CH₂CH₂–N⁺(piperazine)–N⁺–cyclohexyl |
| 551 | X₁–NH–C(O)–CH(NH₃⁺)–phenyl |
| 552 | X₁–NH–C(O)–O–C(CH₃)₂–CH₃ (Boc) |
| 553 | X₁–NH–C(O)–CH₂–(2-phenylindol-3-yl) |
| 554 | X₁–NH–C(O)–CH₂–O–(4-OCF₃-phenyl) |
| 555 | X₁–NH–C(O)–(2-chlorophenyl) |
| 556 | X₁–NH–C(O)–CH₂–N⁺(piperazine)–N⁺–phenyl |
| 629 | X₁–NH–C(O)–N[H]–S(O)₂–(4-chlorophenyl) |

TABLE VIII-continued

| Ex. No. | R1 |
|---|---|
| 8 (Compound No. 630) | naphthalen-1-yl sulfonyl urea |
| 631 | 2-methyl-3-chlorophenyl sulfonyl urea |
| 632 | 4-methoxyphenyl sulfonyl urea |
| 633 | 3-bromophenyl sulfonyl urea |
| 634 | biphenyl-4-yl sulfonyl urea |
| 635 | naphthalen-2-yl sulfonyl urea |
| 636 | 2,3-dichlorophenyl sulfonyl urea |
| 637 | 3-nitrophenyl sulfonyl urea |
| 638 | 2-bromophenyl sulfonyl urea |

TABLE VIII-continued
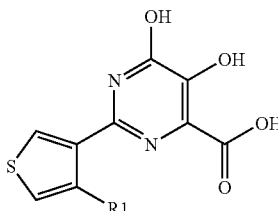
| Ex. No. | R1 |
|---|---|
| 639 | 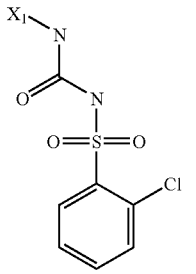 |
| 640 | 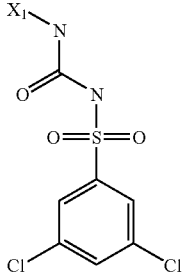 |
| 641 | 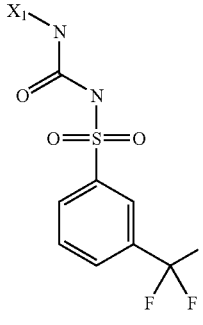 |
| 642 | 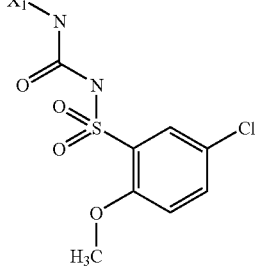 |
TABLE VIII-continued
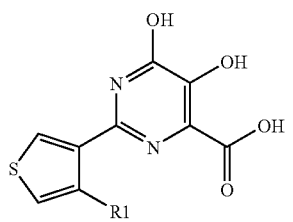
| Ex. No. | R1 |
|---|---|
| 643 | 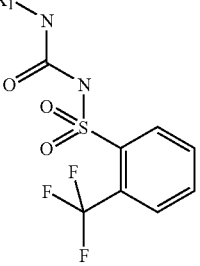 |
| 644 | 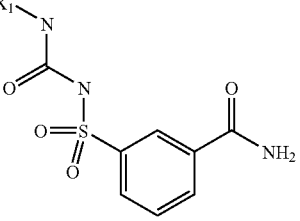 |
| 645 | 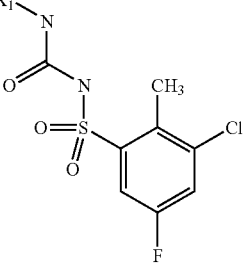 |
| 646 | 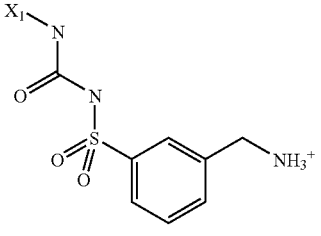 |

TABLE VIII-continued

[Structure: pyrimidine with OH, OH, COOH groups and thiophene with R1]

| Ex. No. | R1 |
|---|---|
| 647 | X₁-NH-C(O)-N(H)-SO₂-[3-substituted phenyl]-NH-C(O)-CH(CH₃)-NH₃⁺ |
| 648 | X₁-NH-C(O)-N(H)-SO₂-[3-substituted phenyl]-NH-C(O)-CH₂-phenyl |
| 649 | X₁-NH-C(O)-N(H)-SO₂-[3-substituted phenyl]-NH-C(O)-CH₂-(2-methylphenyl) |
| 650 | X₁-NH-C(O)-N(H)-SO₂-[2-chloro-6-substituted phenyl]-CH₂-N⁺(CH₂CH₃)₂ |

TABLE IX

[Structure: pyrimidine with OH, OH, COOH groups and thiophene (2-position) with R1]

| Ex. No. | R1 |
|---|---|
| 557 | X₁-NH-C(O)-O-CH₂-phenyl |
| 558 | X₁-NH-C(O)-O-C(CH₃)₃ |
| 651 | X₁-CH₂-O- |
| 652 | X₁-C(O)-O- |

TABLE X

[Structure: pyrimidine with OH, OH, COOH groups and 5-membered heterocycle A1 with R1, R2]

| Ex. No. | A1 | R1 | R2 |
|---|---|---|---|
| 559 | S | X₁-NH-C(O)-phenyl | X₂-H |

TABLE X-continued

| Ex. No. | A1 | R1 | R2 |
|---|---|---|---|
| 560 | O | X₁-N(C=O)-C₆H₄-C(CH₃)₃ | X₂-H |
| 561 | O | X₁-N(C=O)-C₆H₅ | X₂-H |
| 562 | S | X₁-H | H₃C-X₂ |

TABLE XI

| Ex. No. | R1 |
|---|---|
| 563 | thiazol-2-yl (X₁) |
| 564 | furan-2-yl (X₁) |
| 565 | pyrazin-2-yl (X₁) |
| 566 | isoquinolin-3-yl (X₁) |

TABLE XI-continued

| Ex. No. | R1 |
|---|---|
| 567 | indol-3-yl (X₁) |
| 568 | 5-methylisoxazol-3-yl (X₁) |
| 569 | 1-hydroxypropyl (CH₃CH₂CH(OH)-X₁) |
| 570 | 5,7-dimethylpyrazolo[1,5-a]pyrimidin-3-yl (X₁) |
| 571 | 3-aminopyrazin-2-yl with NH₃⁺ (X₁) |
| 572 | benzyloxy(thiophen-2-yl)methyl (X₁) |

TABLE XIIa
| Ex. No. |
|---|
| 573 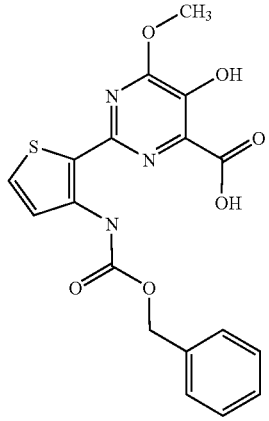 |
| 574 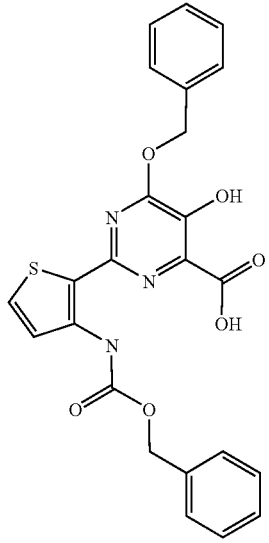 |
TABLE XIIb
| 575 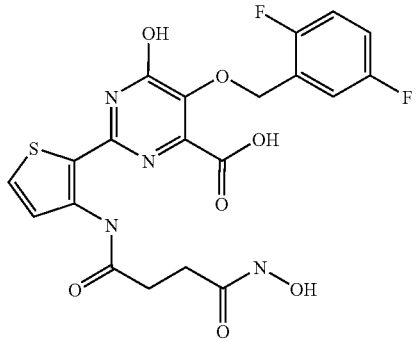 |
|---|
| 576 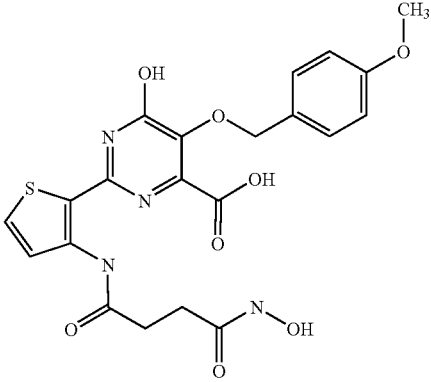 |
TABLE XIIc
| Ex. No. |
|---|
| 577 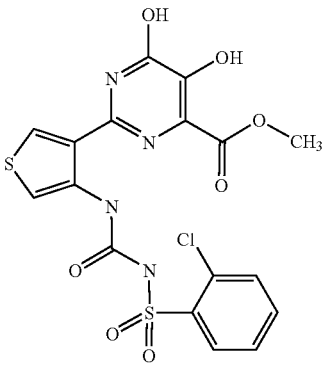 |

TABLE XIIc-continued
| Ex. No. | |
|---|---|
| 578 | 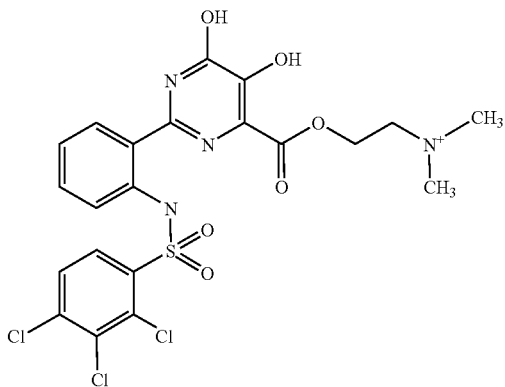 |
| 579 | 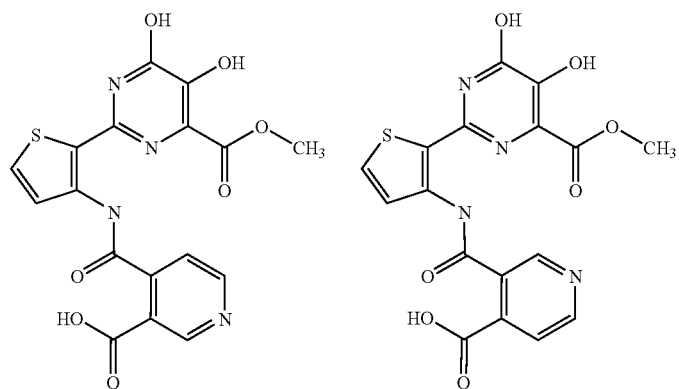 |
| 580 | 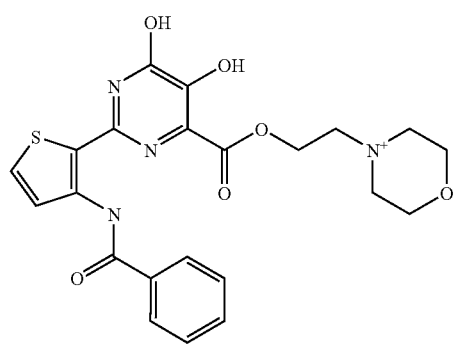 |
| 581 | 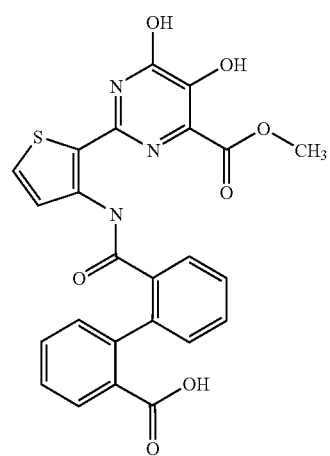 |

TABLE XIIc-continued
| Ex. No. | |
|---|---|
| 582 | 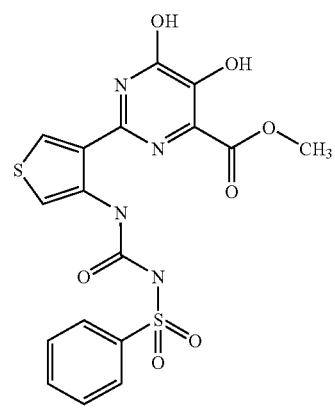 |
| 583 | 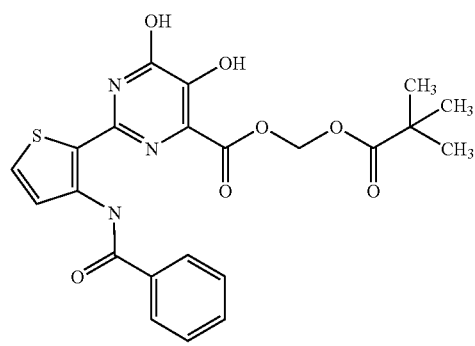 |
| 584 | 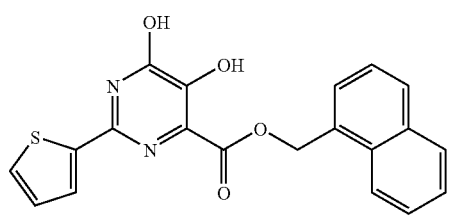 |
| 585 | 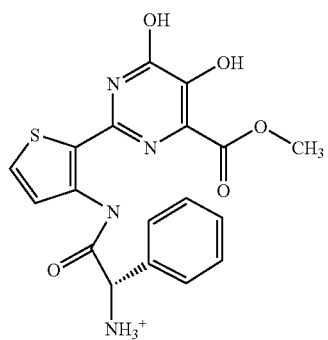 |

TABLE XIIc-continued
| Ex. No. |
| --- |
| 586 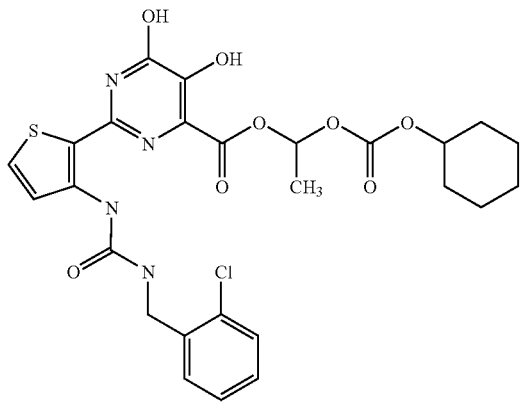 |
| 587 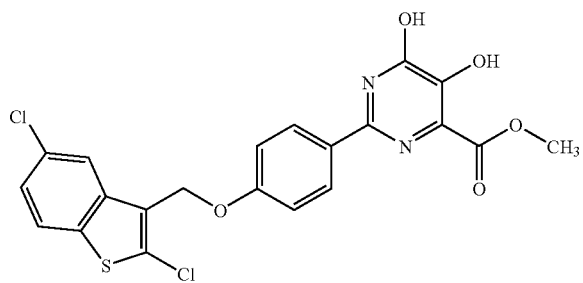 |
| 588 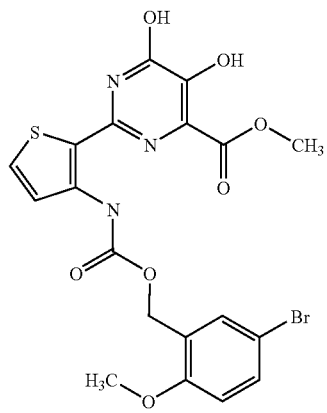 |
| 589 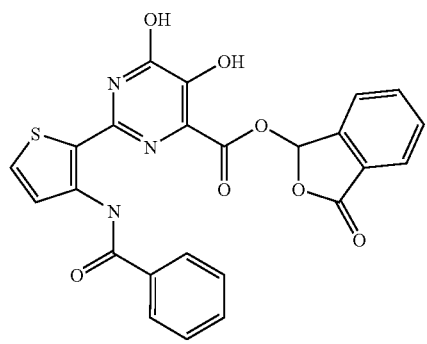 |

TABLE XIIc-continued
| Ex. No. | |
|---|---|
| 590 | 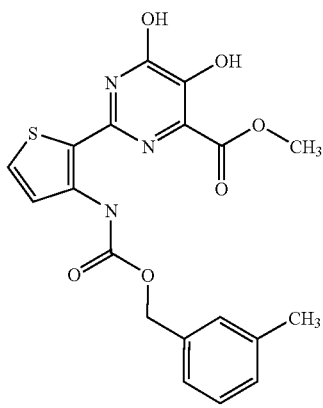 |
| 591 | 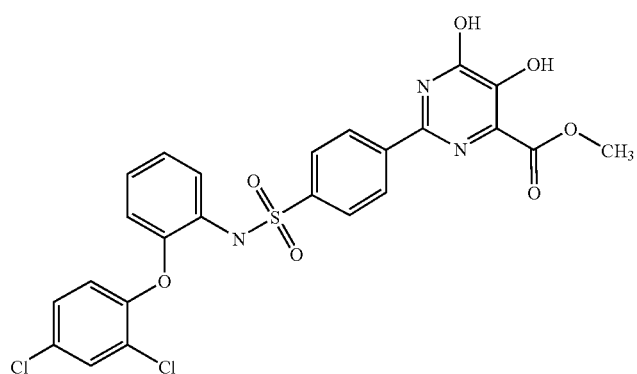 |
| 592 | 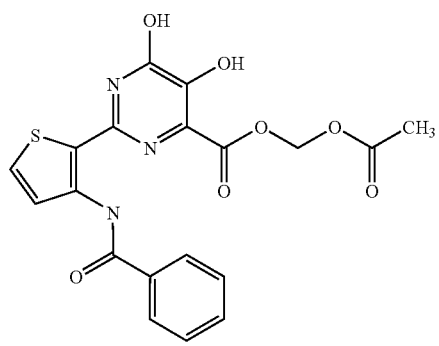 |
| 593 | 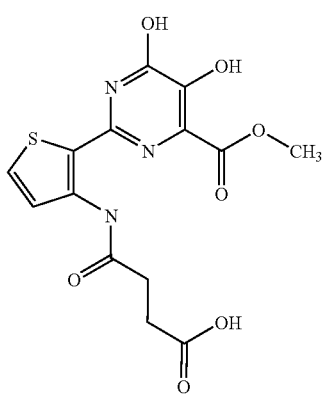 |

The invention claimed is:

1. A compound of formula (I), or a tautomer thereof, or a pharmaceutically acceptable salt or ester thereof:

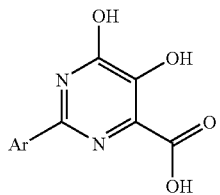

(I)

in which Ar is an optionally substituted aryl group other than optionally substituted phenyl.

2. A compound as claimed in claim 1 wherein Ar represents thienyl, oxazolyl, thiazolyl, furyl, isoquinolinyl, indolyl, isoxazolyl, pyrazolopyrimidinyl or pyrazinyl, any of which groups is optionally substituted.

3. A compound represented by formula (III), or a tautomer thereof, or a pharmaceutically acceptable salt or ester thereof:

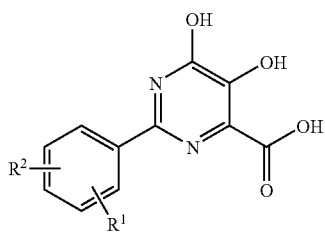

(III)

wherein $R^1$ is hydrogen or —X—$R^3$ and $R^2$ is —X—$R^3$, in which

X is selected from —NH—SO$_2$—, —NH—SO$_2$—NH—, —CH$_2$—SO$_2$-, —SO$_2$—NH—, —NH—CO—NH—, —NH—CS—NH—, —NH—CO—O—, —NH—CO—, —CO—NH—, —NH—CO—NH—SO$_2$-, —NH—CO—NH—CO—, —O—, —S—, —NH—, —CH$_2$-, —CH$_2$O— and —CH$_2$S—; and $R^3$ represents aryl, aralkyl, cycloalkyl, lower alkyl, heterocycloalkyl, lower alkenyl, cycloalkenyl or heterocycloalkenyl, any of which groups is optionally substituted.

4. A compound as claimed in claim 2 wherein Ar represents optionally substituted thienyl.

5. A compound as claimed in claim 4 represented by formula (XI), or a tautomer thereof, or a pharmaceutically acceptable salt or ester thereof:

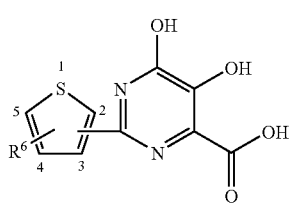

(XI)

wherein $R^6$ represents hydrogen or —X—$R^3$, in which

X is selected from —NH—SO$_2$—, —NH—SO$_2$—NH—, —CH$_2$—SO$_2$-, —SO$_2$—NH—, —NH—CO—NH—, —NH—CS—NH—, —NH—CO—O—, —NH—CO—, —CO—NH—, —NH—CO—NH—SO$_2$-, —NH—CO—NH—CO—, —O—, —S—, —NH—, —CH$_2$-, —CH$_2$O— and —CH$_2$S—; and $R^3$ represents aryl, aralkyl, cycloalkyl, lower alkyl, heterocycloalkyl, lower alkenyl, cycloalkenyl or heterocycloalkenyl, any of which groups is optionally substituted.

6. A compound of formula (I), or a tautomer thereof, or a pharmaceutically acceptable salt thereof:

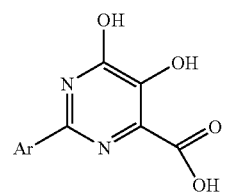

(I)

in which Ar is an optionally substituted aryl group other than optionally substituted phenyl, and which is derivatized at one or more of the 4-hydroxy, 5-hydroxy or 6-carboxy groups; wherein derivatization of the 4-hydroxy or 5-hydroxy group is etherification with alkyl, optionally substituted aryl, or optionally substituted aralkyl; and derivatization of the 6-carboxy group is esterification with an optionally substituted lower alkyl alcohol.

7. A pharmaceutical composition comprising a compound of formula (I) as defined in claim 1, or a tautomer thereof, or a pharmaceutically acceptable salt or ester thereof, in association with a pharmaceutically acceptable carrier.

8. A process for the preparation of a compound of formula (I) as defined in claim 1, which comprises hydrolysis of the corresponding methyl or other ester of formula 2.

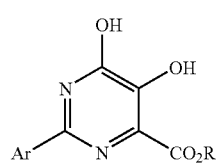

2 where R is a methyl or other lower alkyl group.

9. A compound of formula (III), or a tautomer thereof, or a pharmaceutically acceptable salt thereof:

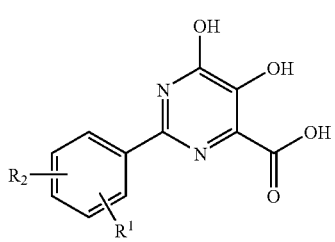

(III)

wherein $R^1$ is hydrogen or —X—$R^3$ and $R^2$ is —X—$R^3$, in which

X is selected from —NH—SO$_2$—, —NH—SO$_2$—NH—, —CH$_2$—SO$_2$-, —SO$_2$—NH—, —NH—CO—NH—, —NH—CS—NH—, —NH—CO—O—, —NH—CO—, —CO—NH—, —NH—CO—NH—SO$_2$-, —NH—CO—NH—CO—, —O—, —S—, —NH—, —CH$_2$-, —CH$_2$O— and —CH$_2$S—, and $R^3$ represents aryl, aralkyl, cycloalkyl, lower alkyl, heterocycloalkyl, lower alkenyl, cycloalkenyl or heterocycloalkenyl, any of which groups is optionally substituted; wherein the compound is derivatized at one or more of the 4-hydroxy, 5-hydroxy or 6-carboxy groups, wherein derivatization of the 4-hydroxy or 5-hydroxy group is etherification with alkyl, optionally substituted aryl, or optionally substituted aralkyl; and derivatization of the 6-carboxy group is esterification with an optionally substituted lower alkyl alcohol.

10. A pharmaceutical composition comprising a derivatized compound of formula (I) as defined in claim 6, or a tautomer thereof, or a pharmaceutically acceptable salt thereof, in association with a pharmaceutically acceptable carrier.

11. A pharmaceutical composition comprising a compound of formula (III) as defined in claim 3, or a tautomer thereof, or a pharmaceutically acceptable salt or ester thereof in association with a pharmaceutically acceptable carrier.

12. A pharmaceutical composition comprising a derivatized compound of formula (III) as defined in claim 9, or a tautomer thereof, or a pharmaceutically acceptable salt thereof, in association with a pharmaceutically acceptable carrier.

13. A method of inhibiting hepatitis C virus polymerase which comprises administering to a subject in need of such inhibition an effective amount of:

(A) a compound of formula (I), a tautomer thereof, or a pharmaceutically acceptable salt or ester thereof:

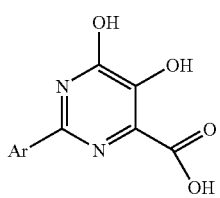

(I)

in which Ar is an optionally substituted aryl group; or (B) a compound of formula (I) which is derivatized at one or more of the 4-hydroxy, 5-hydroxy or 6-carboxy groups, a tautomer thereof, or a pharmaceutically acceptable salt thereof; wherein derivatization of the 4-hydroxy or 5-hydroxy group is etherification with alkyl, optionally substituted aryl, or optionally substituted aralkyl; and derivatization of the 6-carboxy group is esterification with an optionally substituted lower alkyl alcohol.

14. A method of treating or preventing an illness due to hepatitis C virus, which comprises administering to a subject suffering from the condition a therapeutically or prophylactically effective amount of:

(A) a compound of formula (I), a tautomer thereof, or a pharmaceutically acceptable salt or ester thereof:

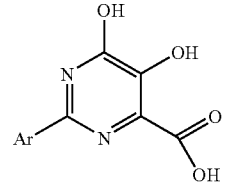

(I)

in which Ar is an optionally substituted aryl group; or (B) a compound of formula (I) which is derivatized at one or more of the 4-hydroxy, 5-hydroxy or 6-carboxy groups, a tautomer thereof, or a pharmaceutically acceptable salt thereof; wherein derivatization of the 4-hydroxy or 5-hydroxy group is etherification with alkyl, optionally substituted aryl, or optionally substituted aralkyl; and derivatization of the 6-carboxy group is esterification with an optionally substituted lower alkyl alcohol.

15. A compound, or a tautomer thereof, or a pharmaceutically acceptable salt or ester thereof, selected from the group consisting of:

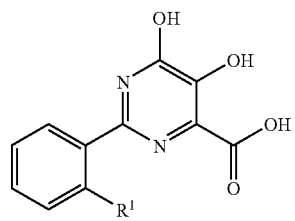

(A)

wherein $R^1$ is selected from the group consisting of:

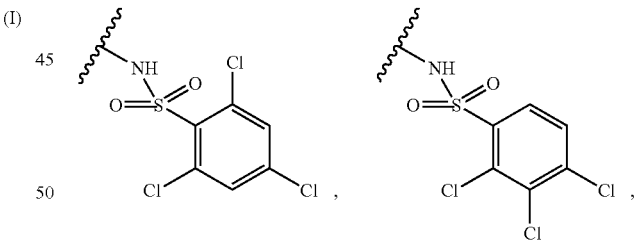

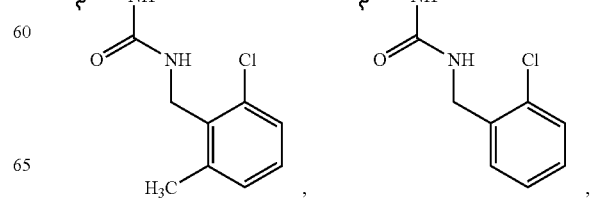

-continued
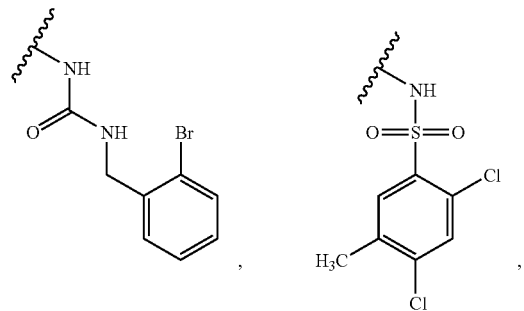
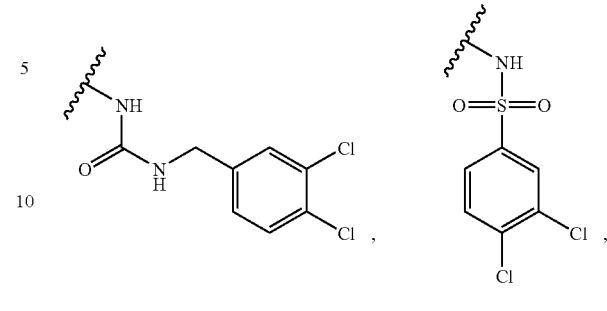
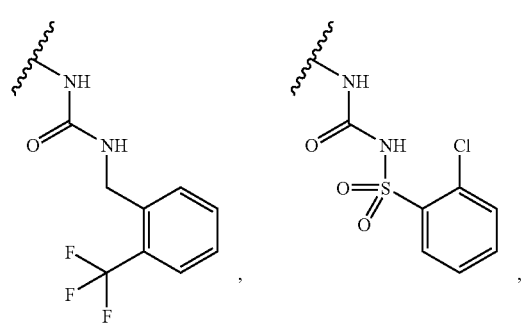
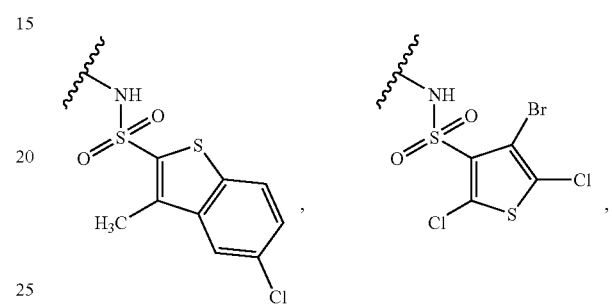
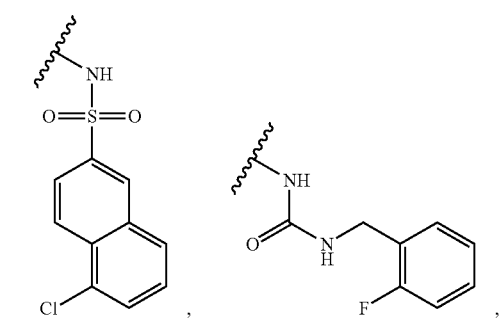
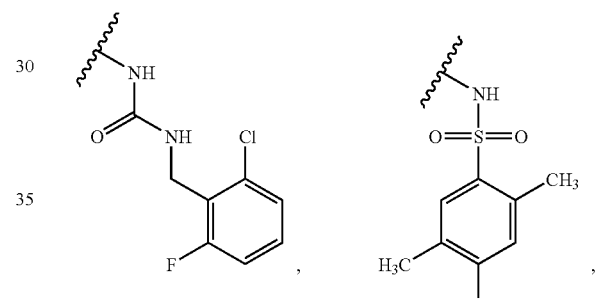
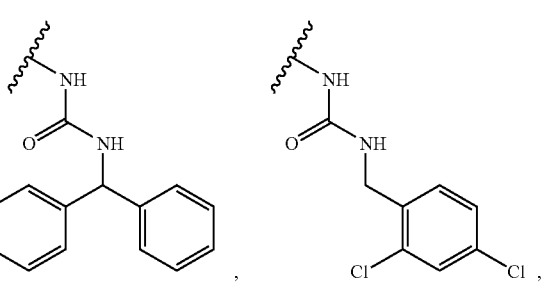
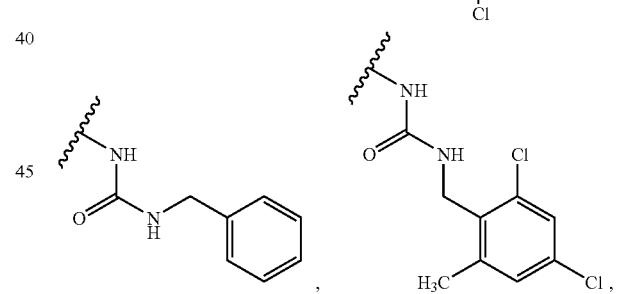
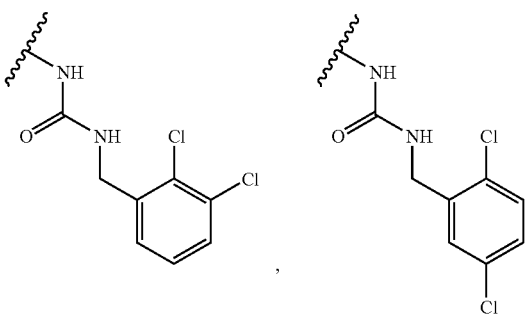
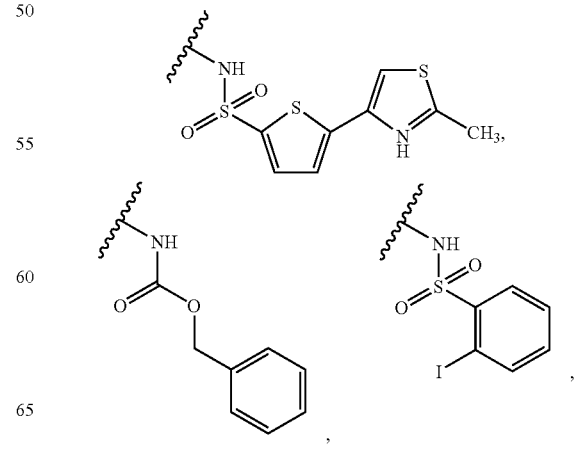

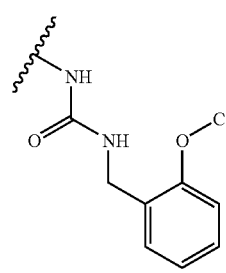 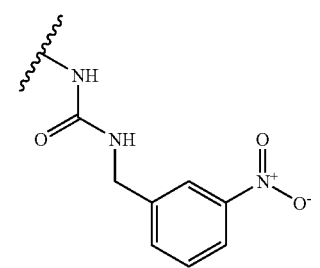 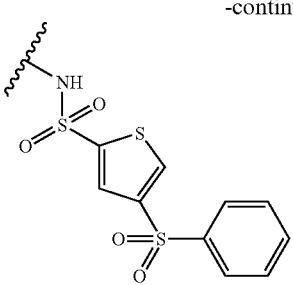 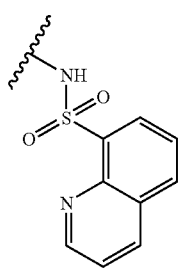
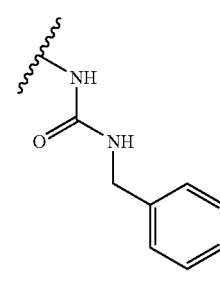 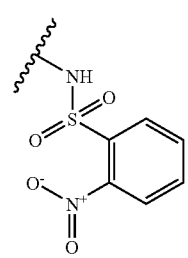 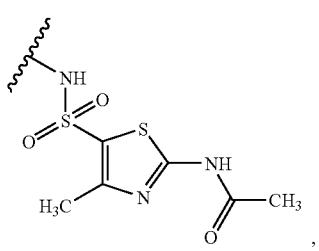
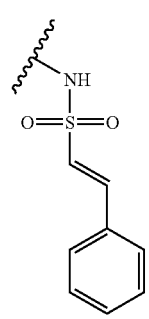 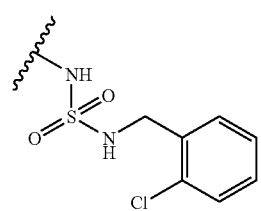 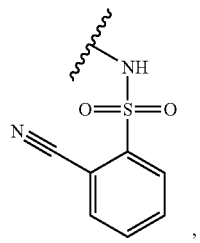 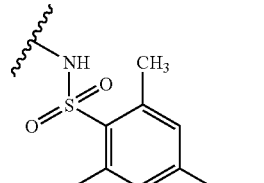
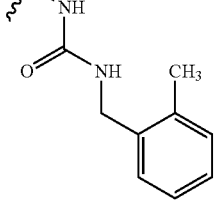 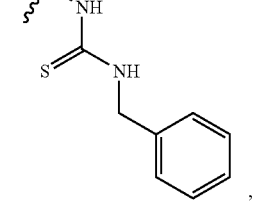
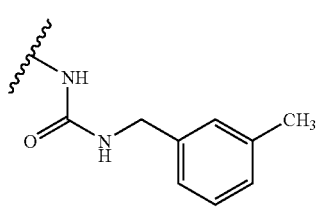 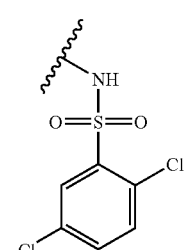 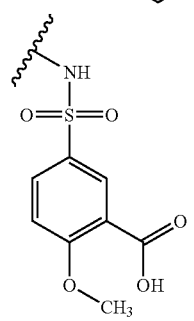 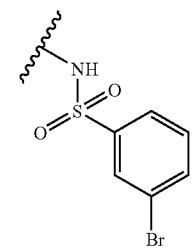
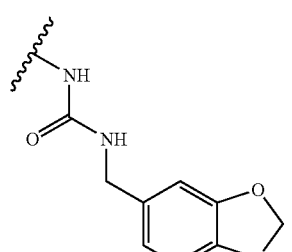 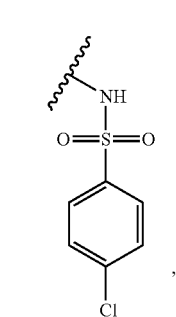 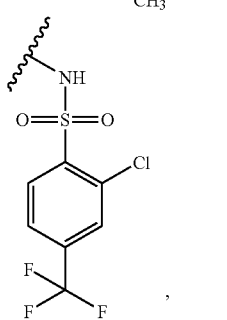 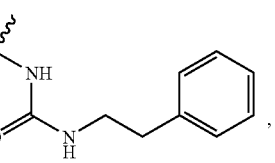

-continued
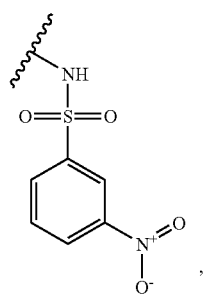 , 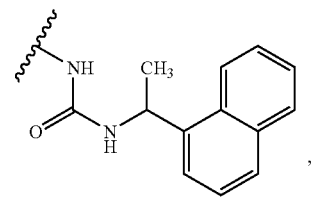 ,
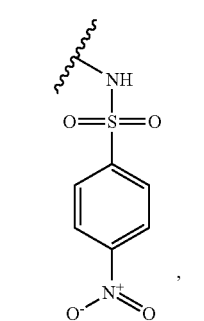 , 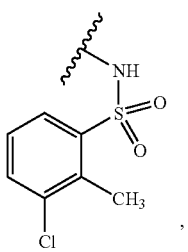 ,
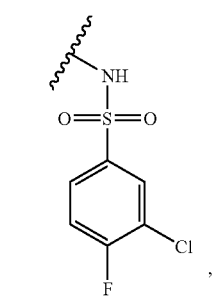 , 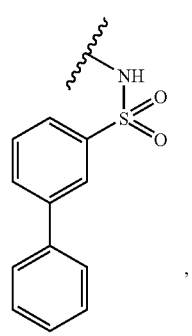 ,
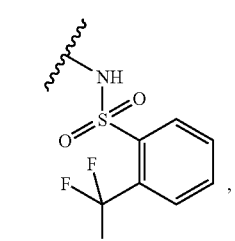 , 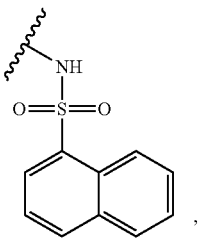 ,
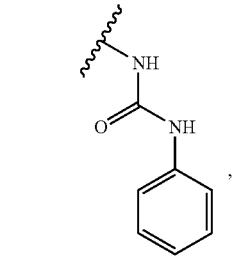 , 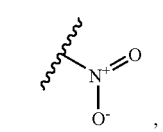 ,
-continued
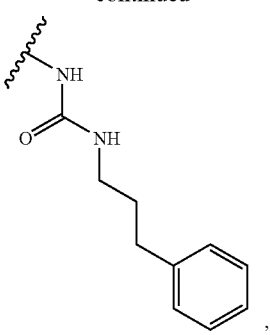 ,
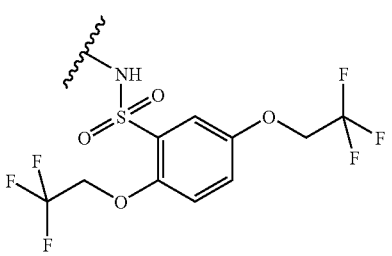 ,
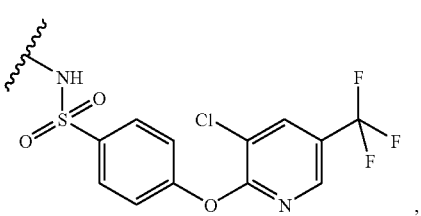 ,
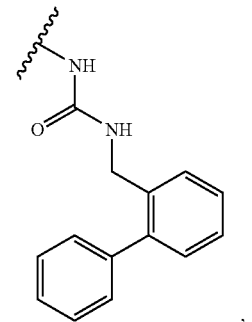 ,
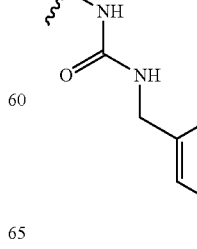 , 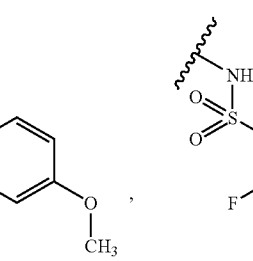 , -continued
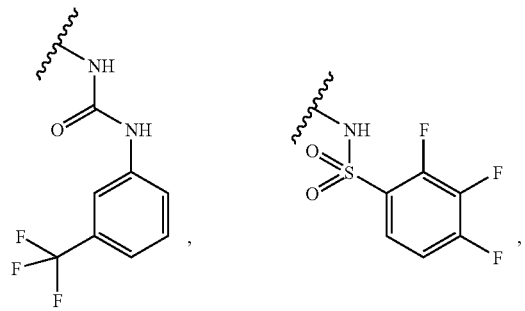
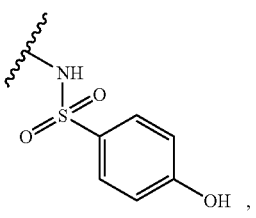
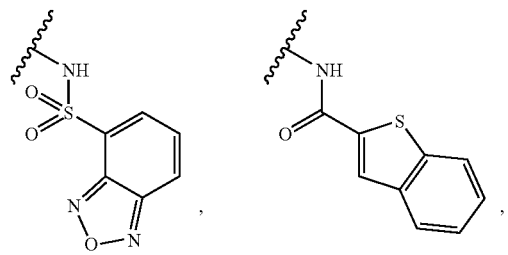
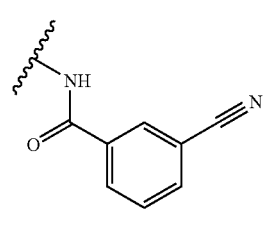, 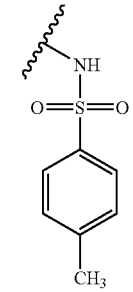
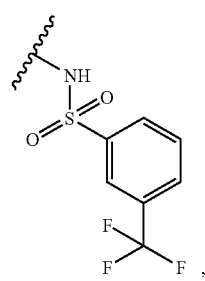
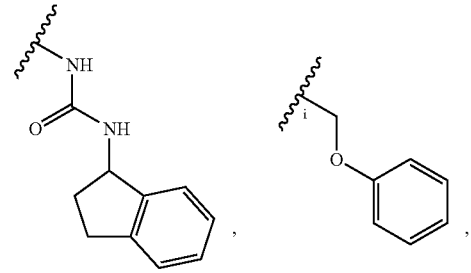
-continued
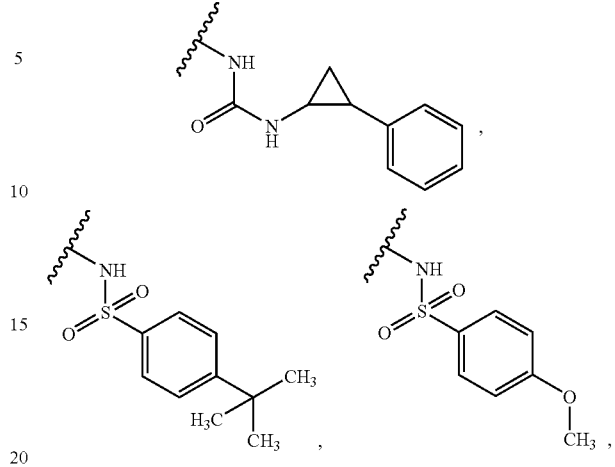
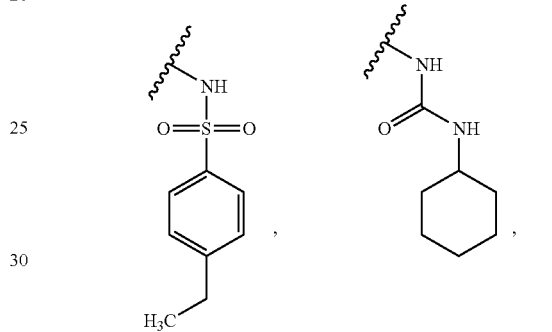
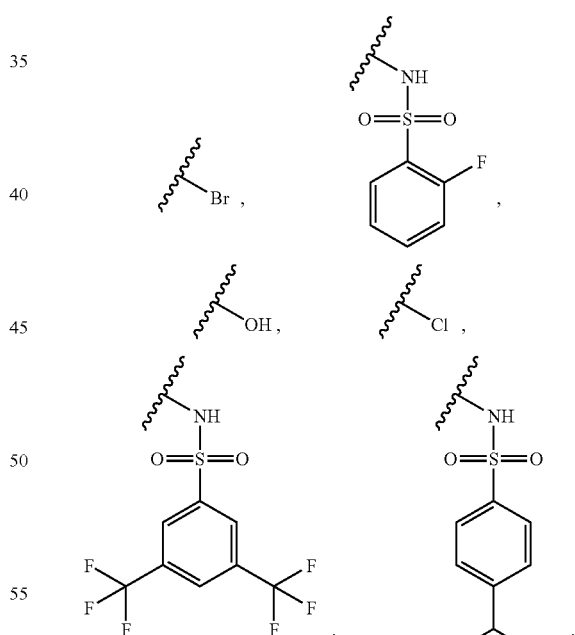
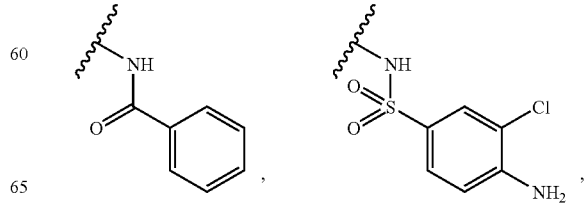

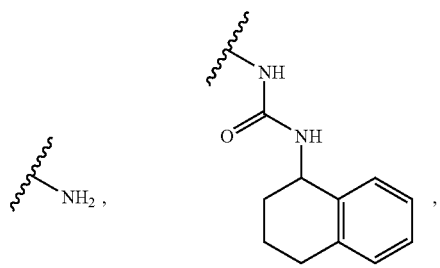
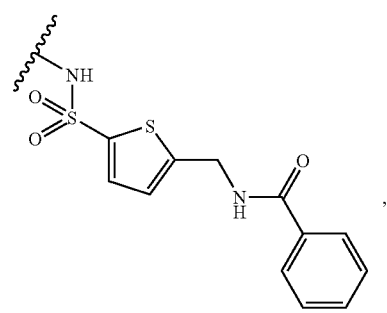
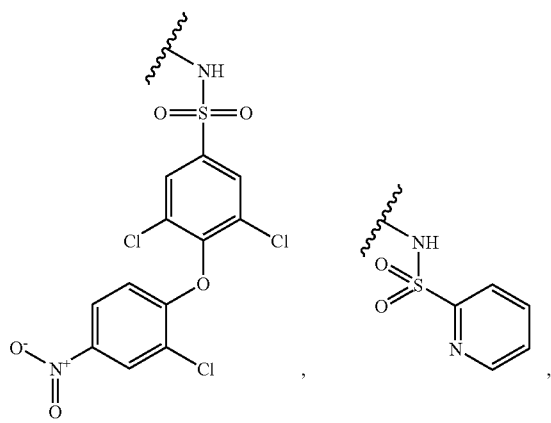
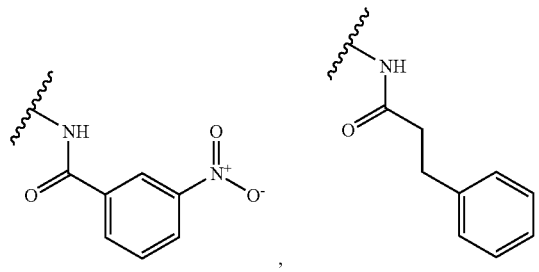
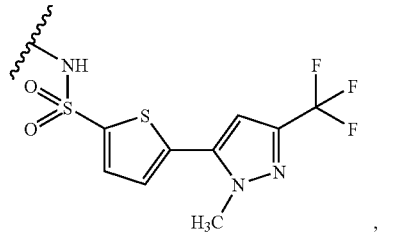
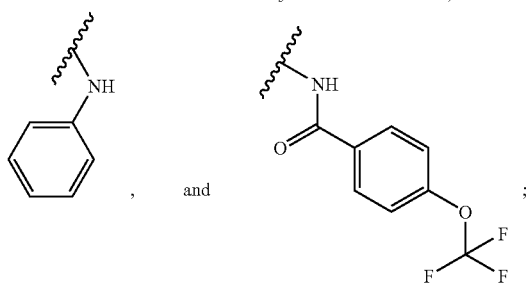
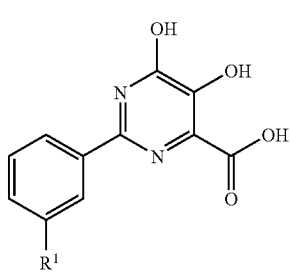
wherein R¹ is selected from the group consisting of:
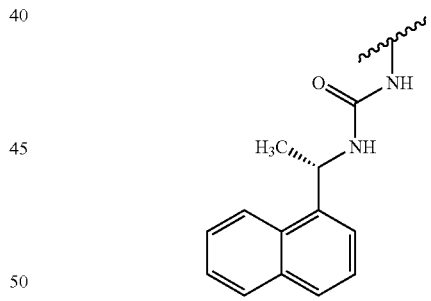
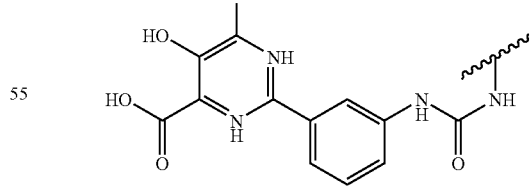
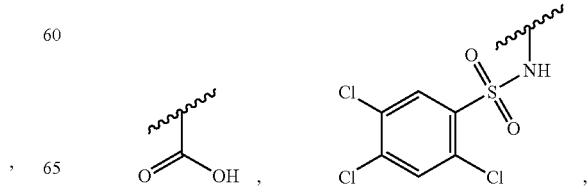

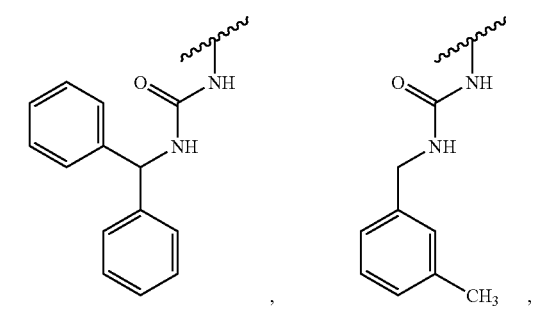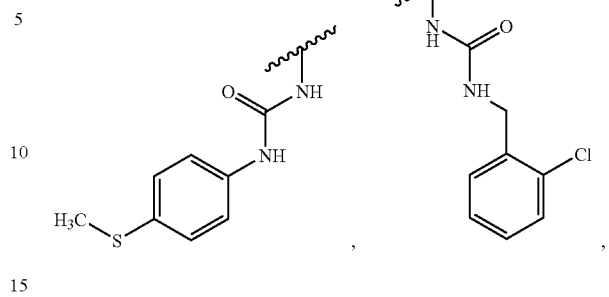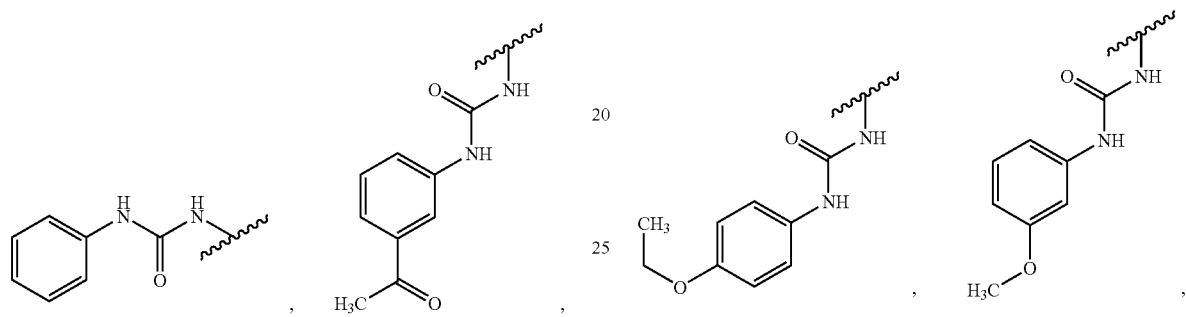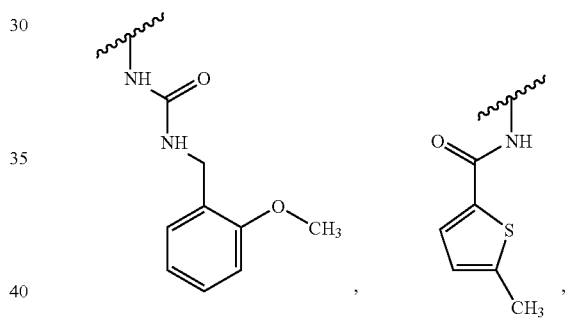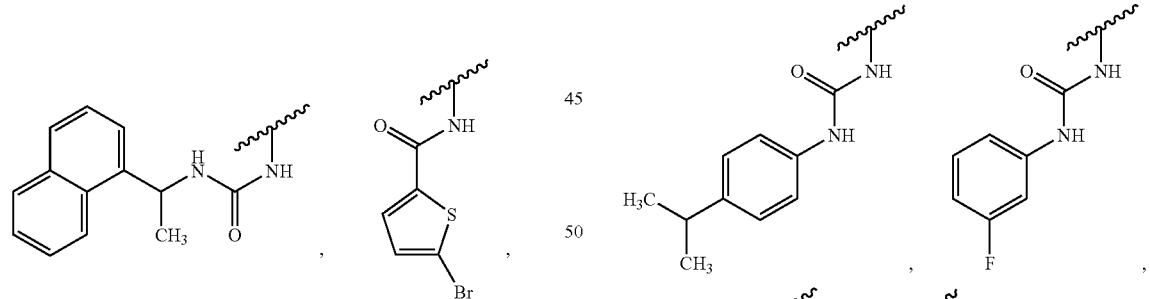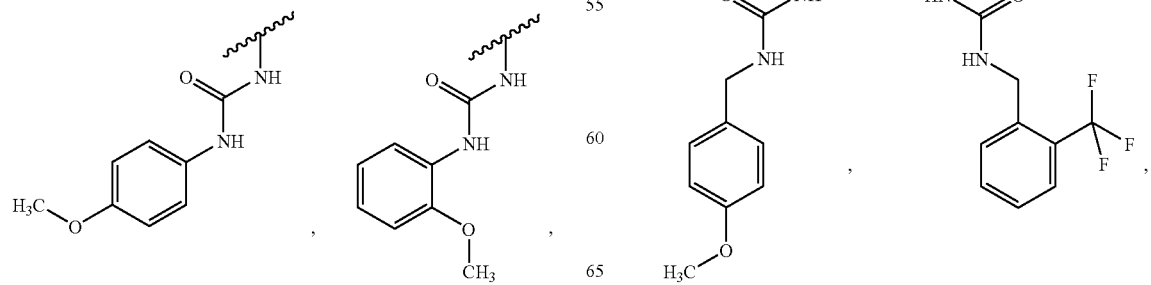

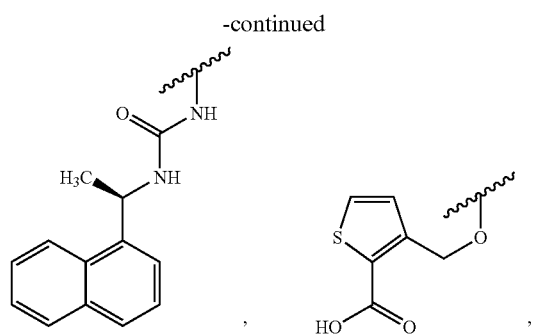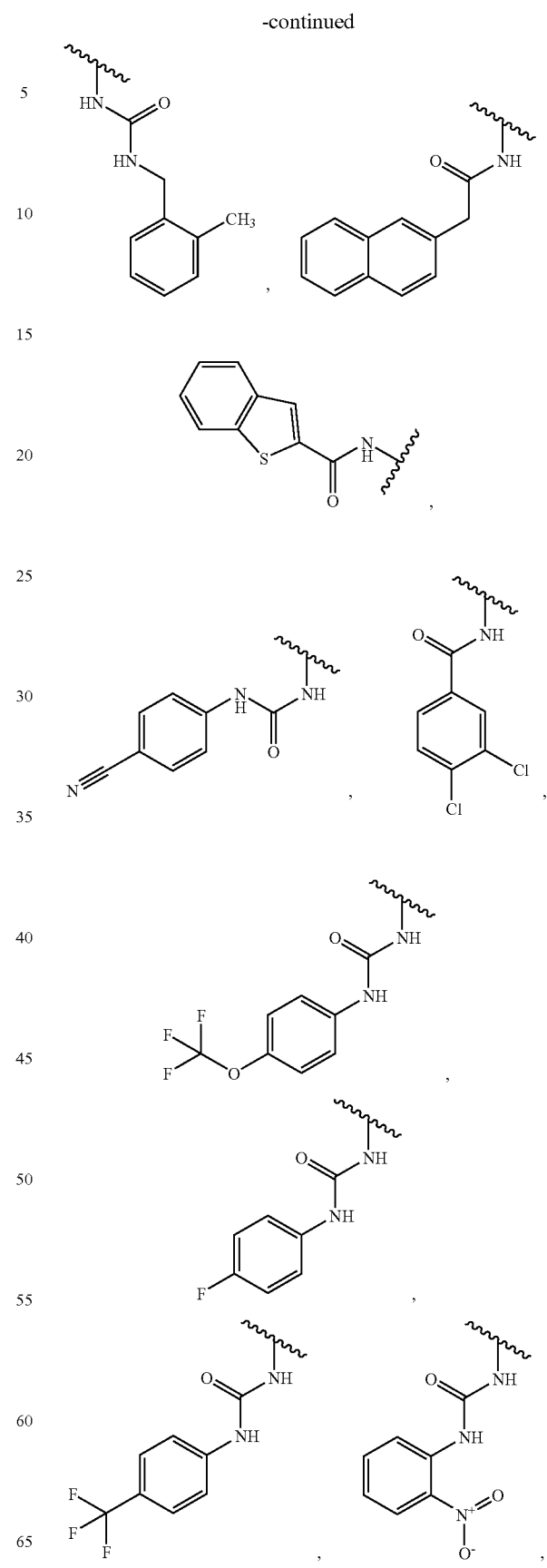

-continued
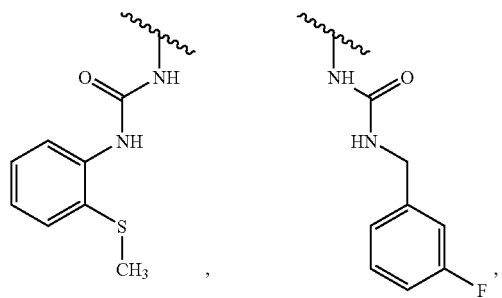
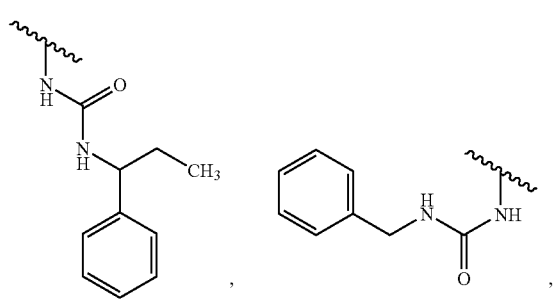
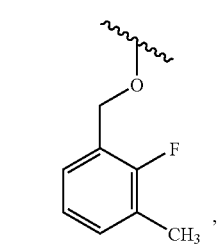
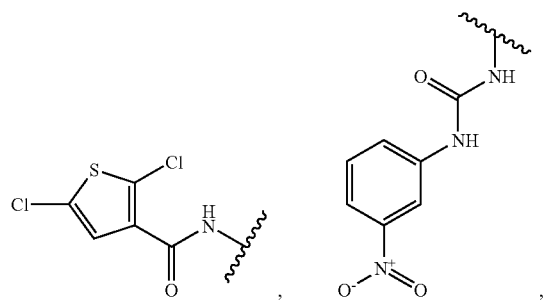
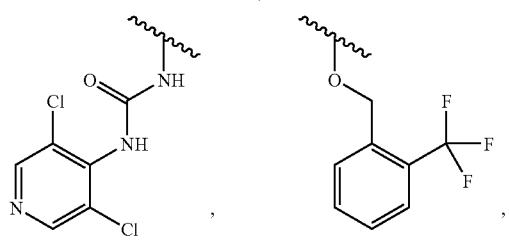
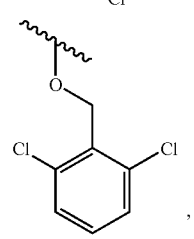
-continued
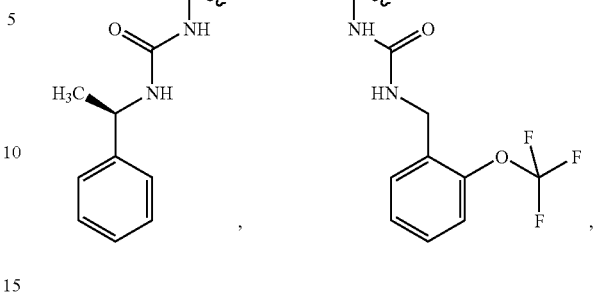
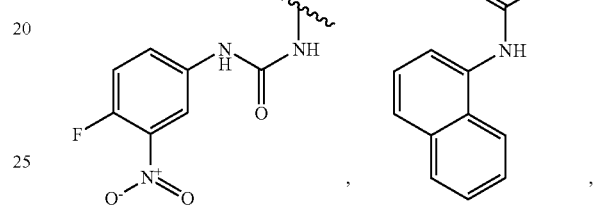
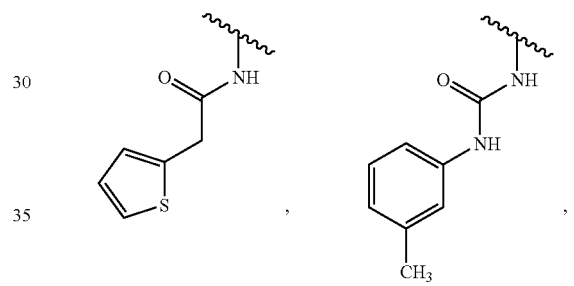
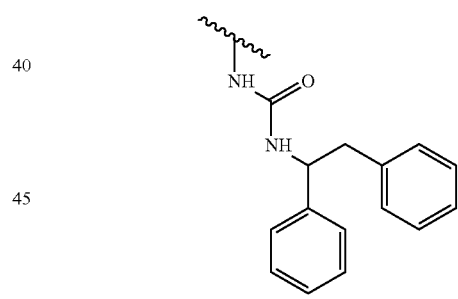
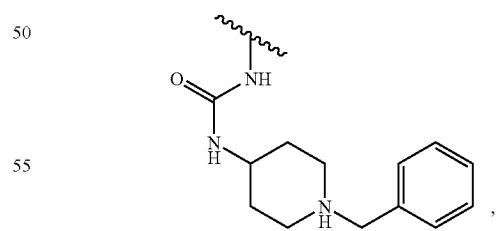
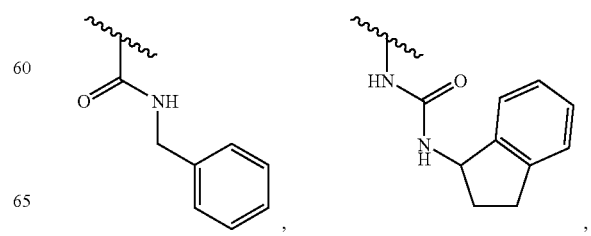

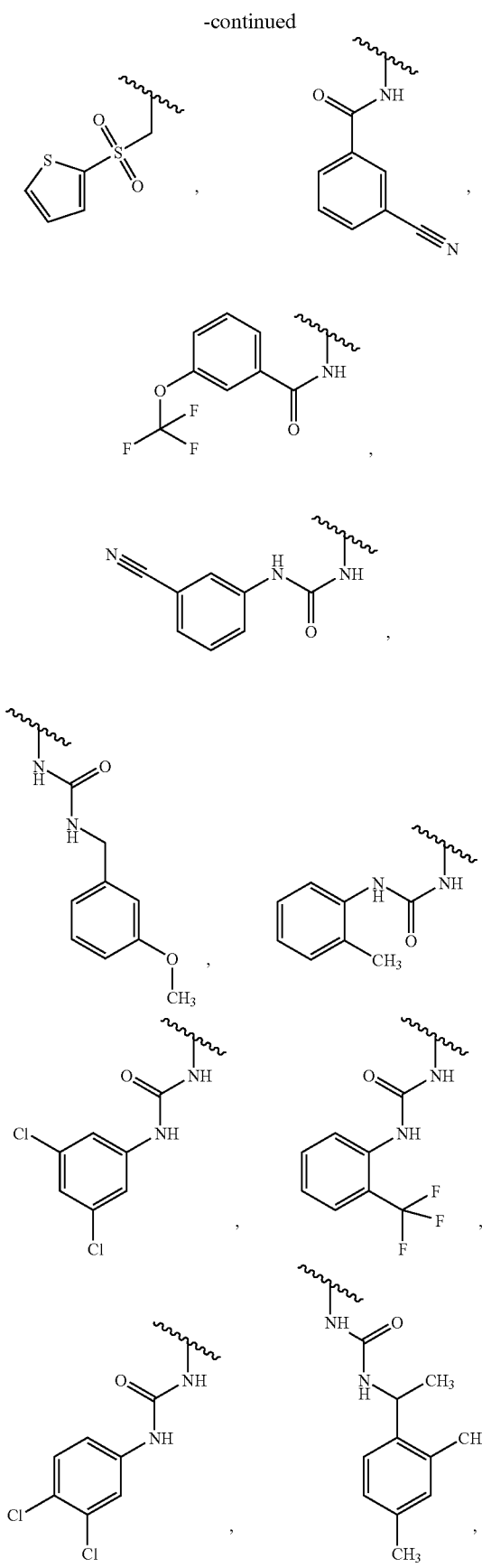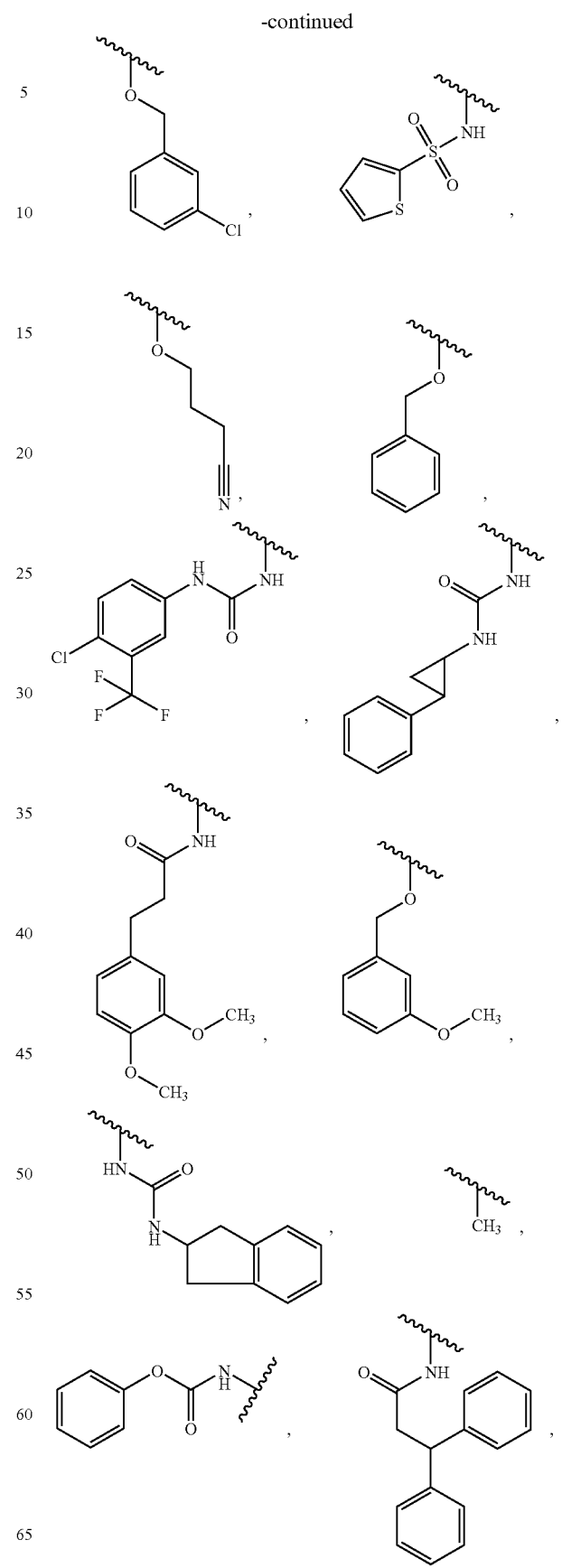

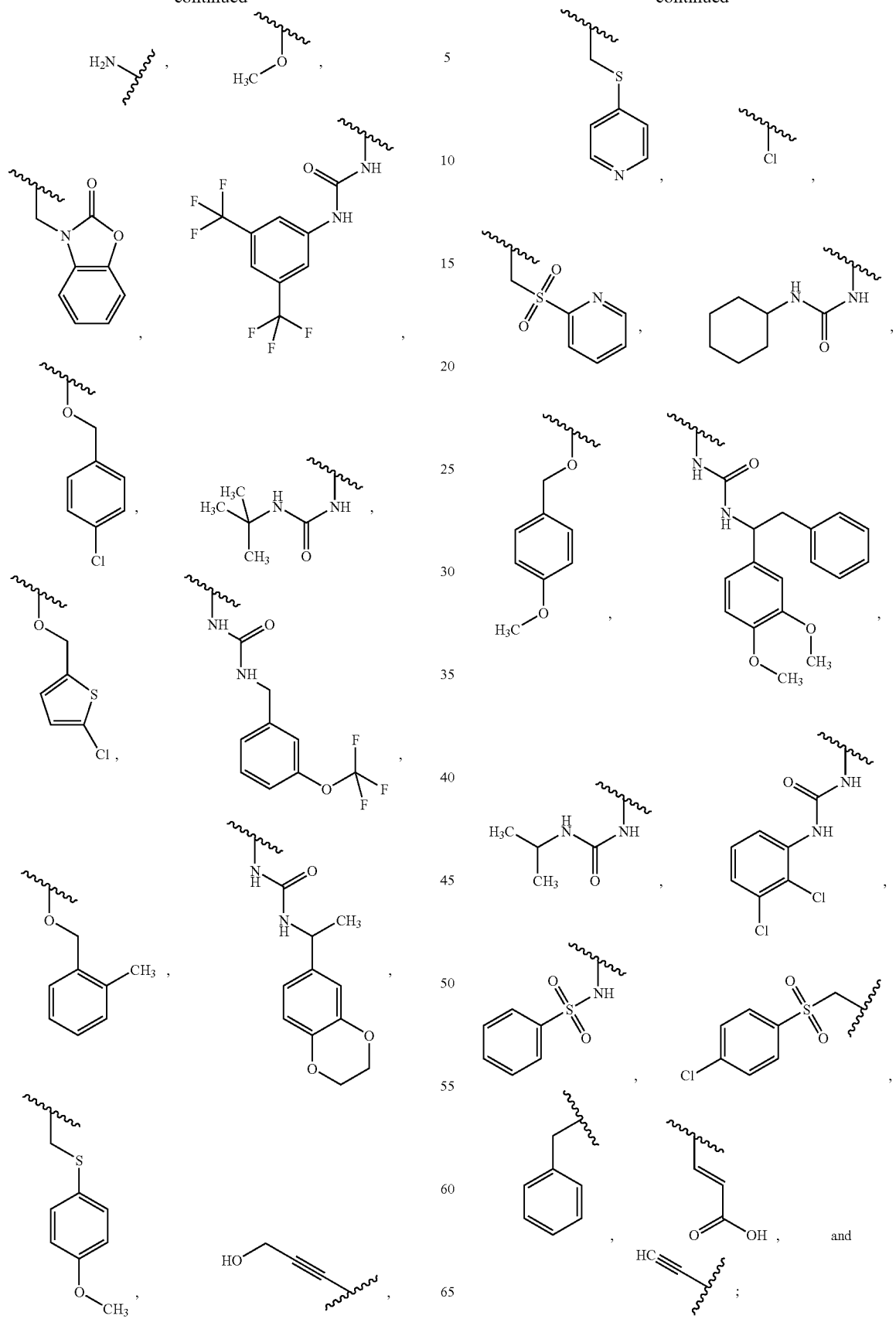

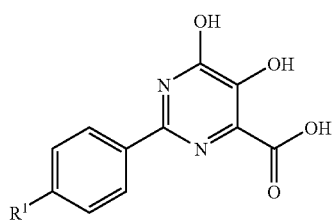
wherein R₁ is selected from the group consisting of:
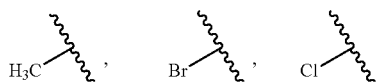
provided the compound is not an ester,
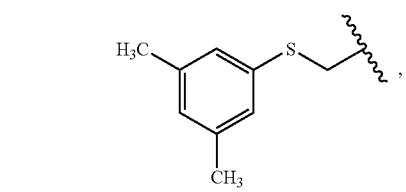
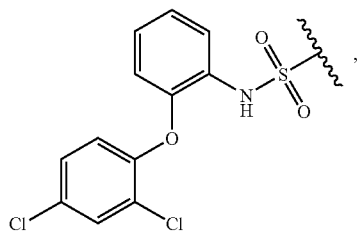
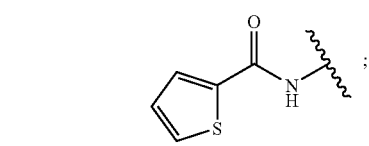
and
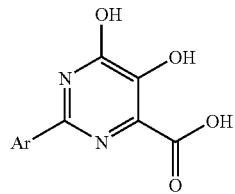
wherein Ar is selected from the group consisting of:
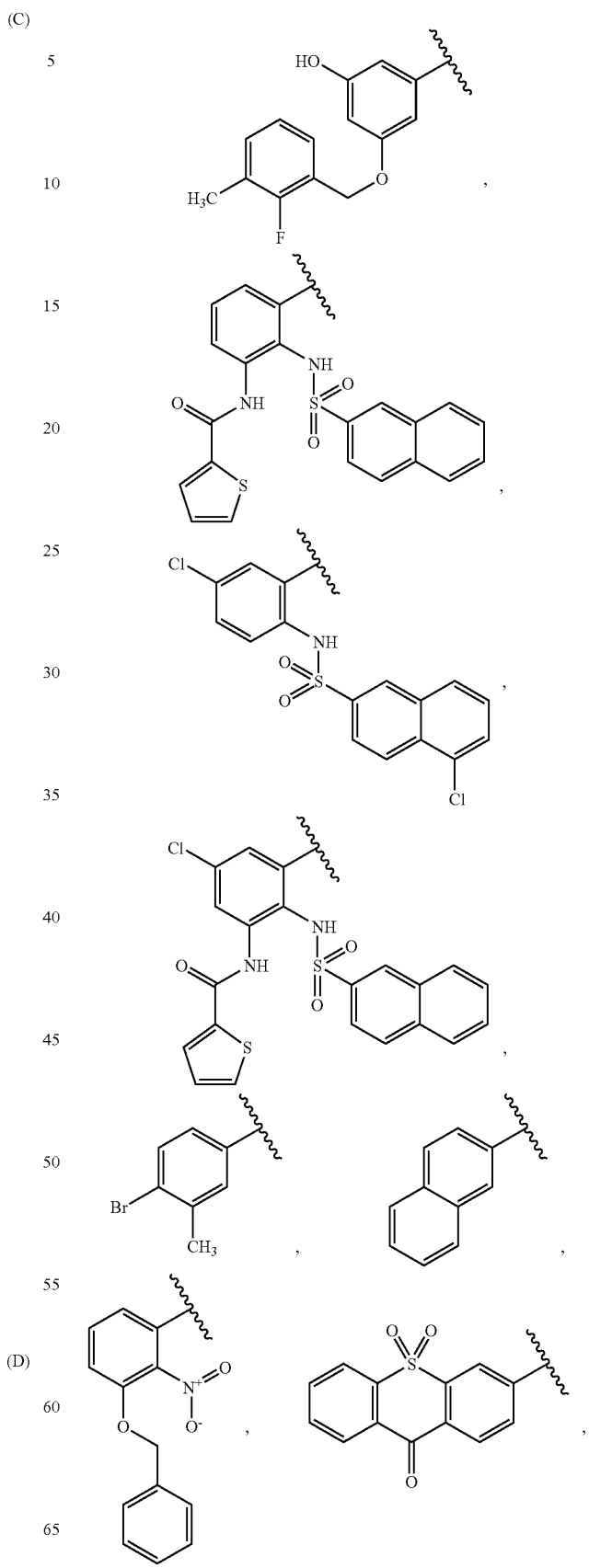

-continued wherein R¹ is selected from the group consisting of:

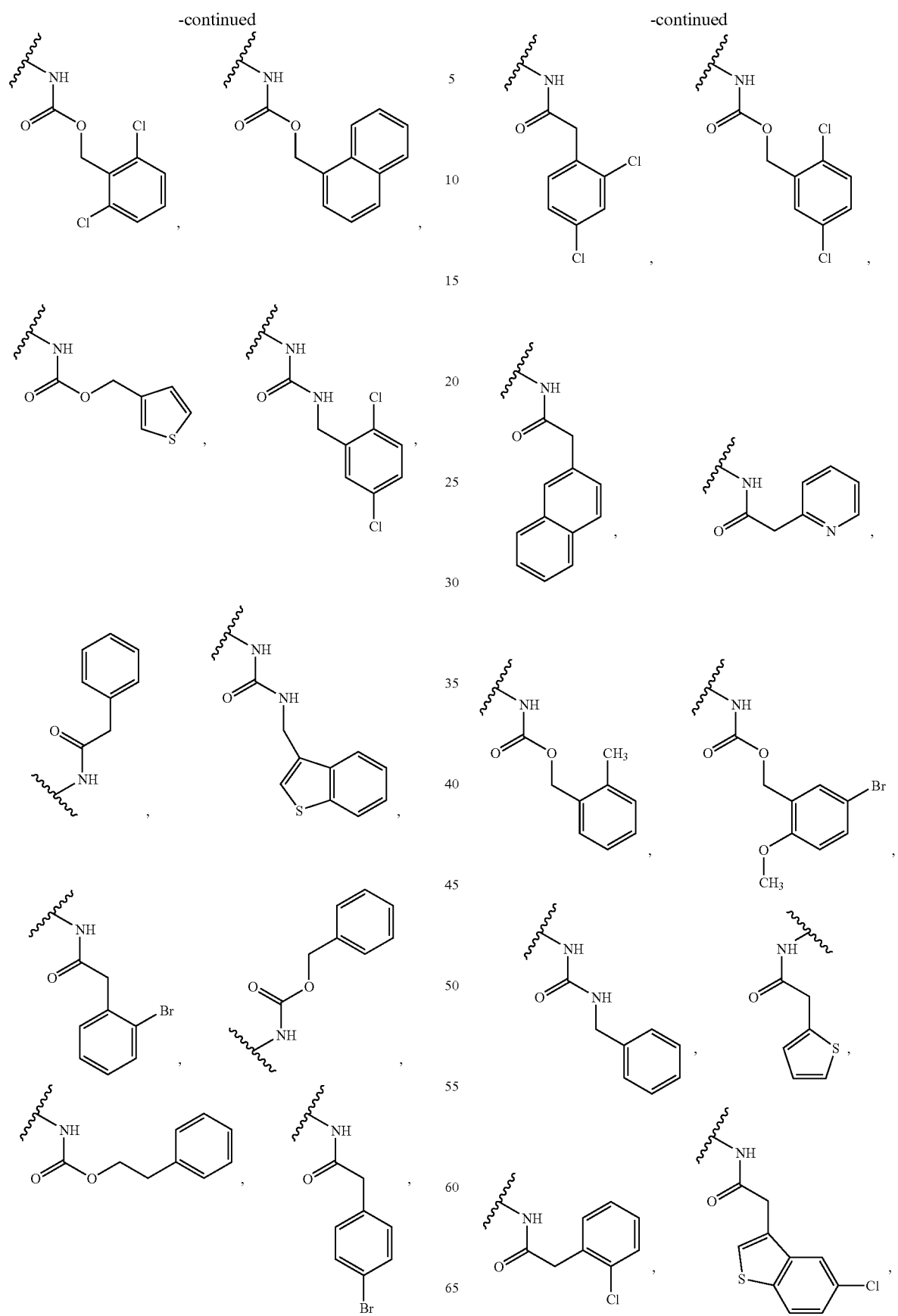

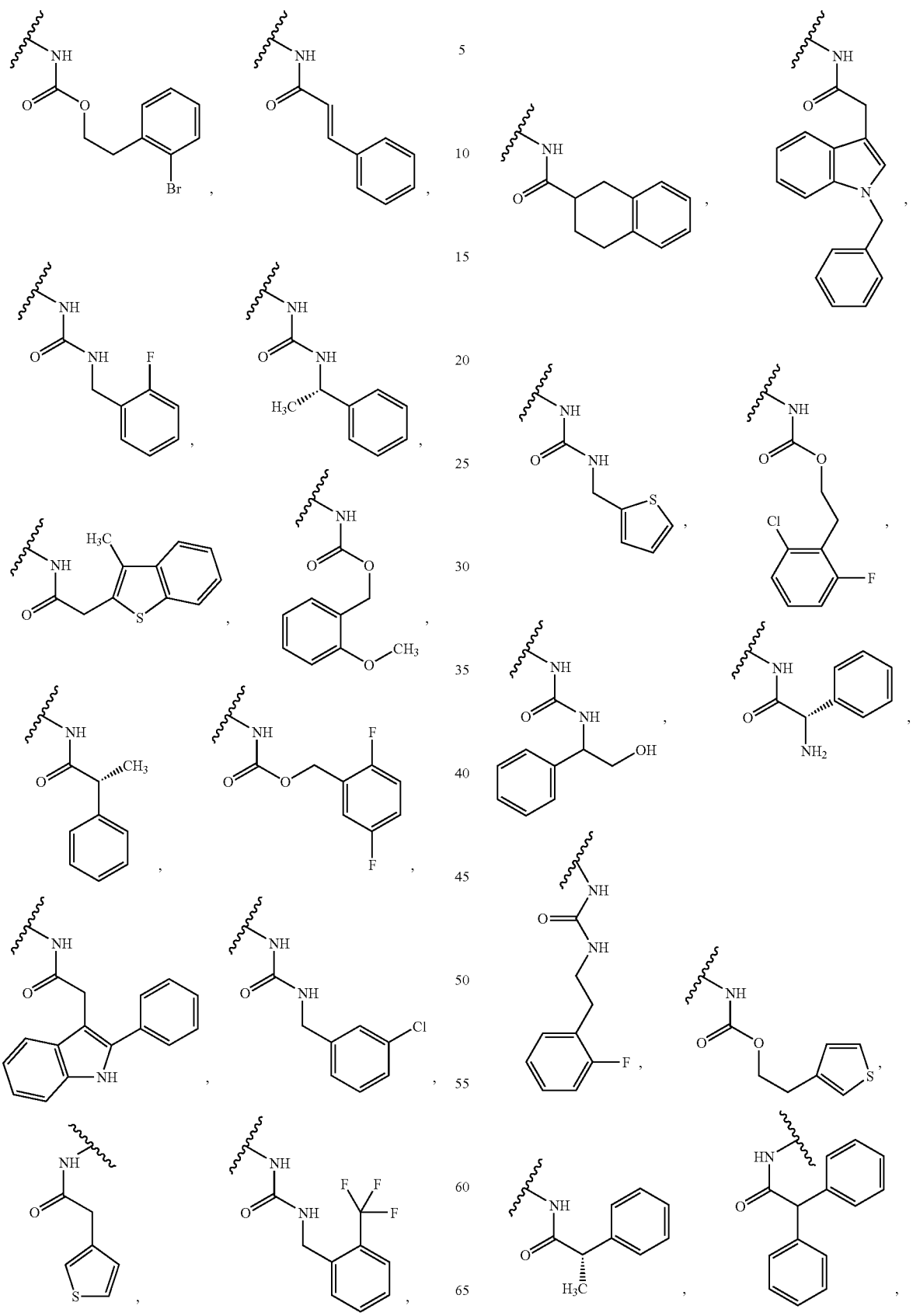

-continued

-continued
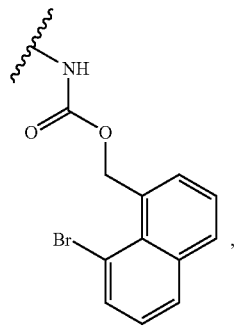,
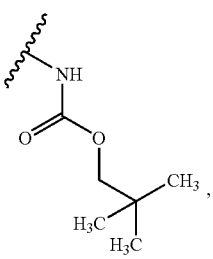,
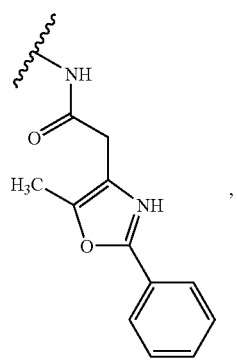,
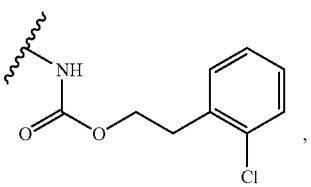,
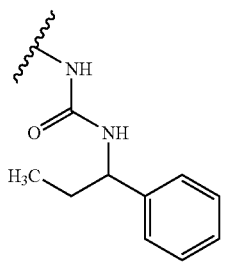, 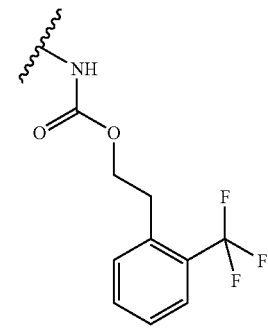,
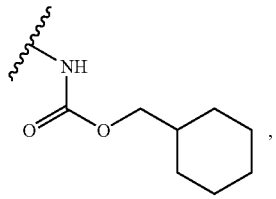,
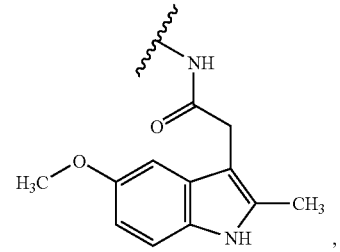,
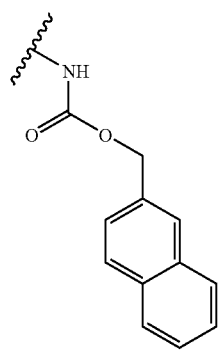, 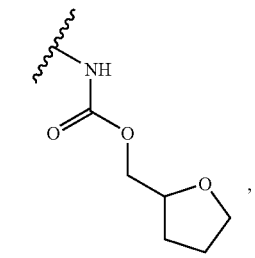,
-continued
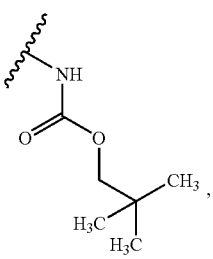, 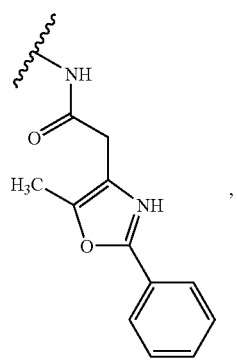,
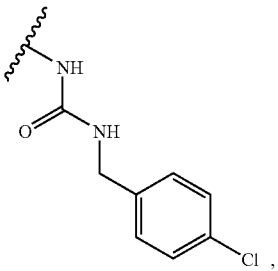, 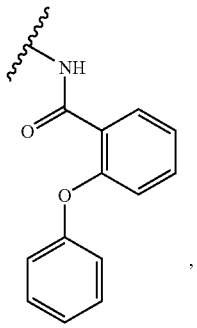,
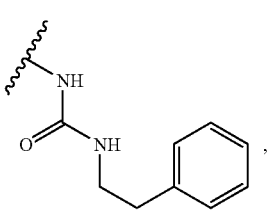, 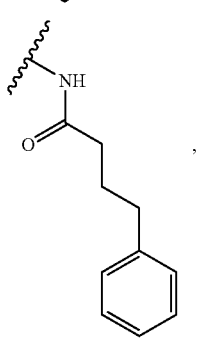,
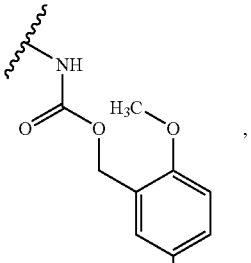, 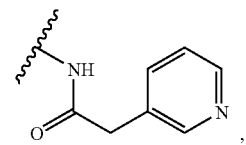,
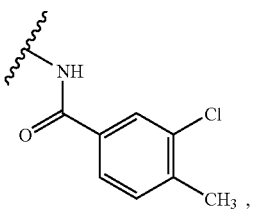, 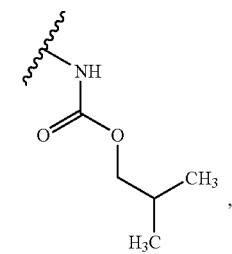,

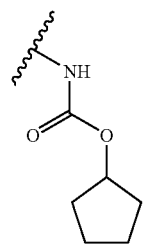 , 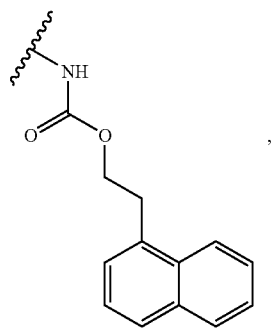 ,
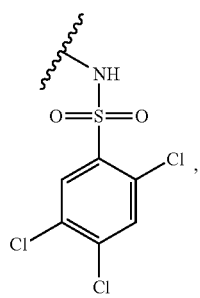 , 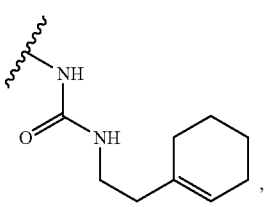 ,
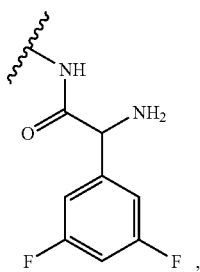 , 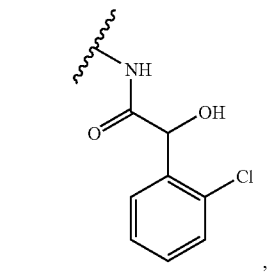 ,
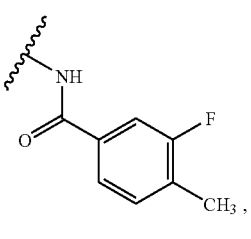 , 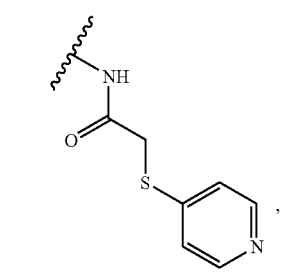 ,
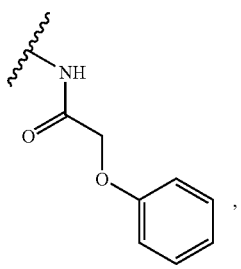 , 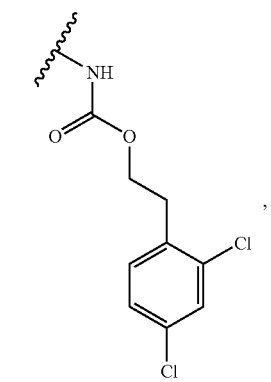 ,
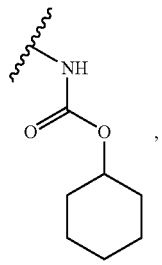 ,  ,
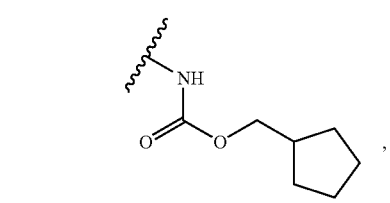 ,
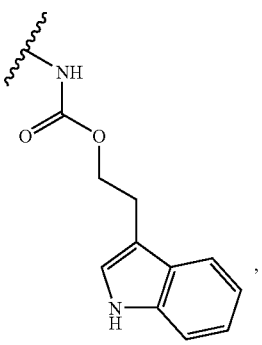 , 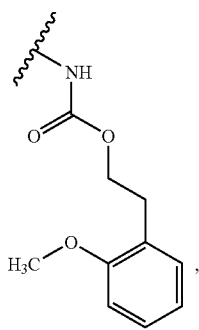 ,
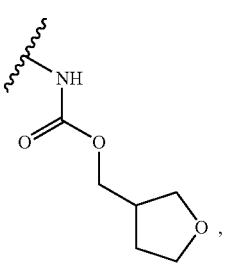 , 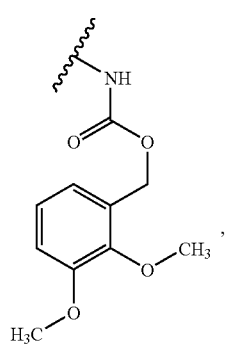 ,
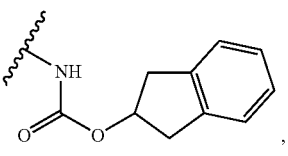 , 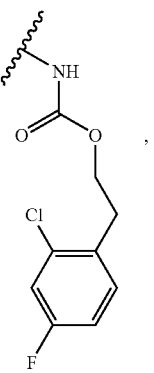 , 199
-continued
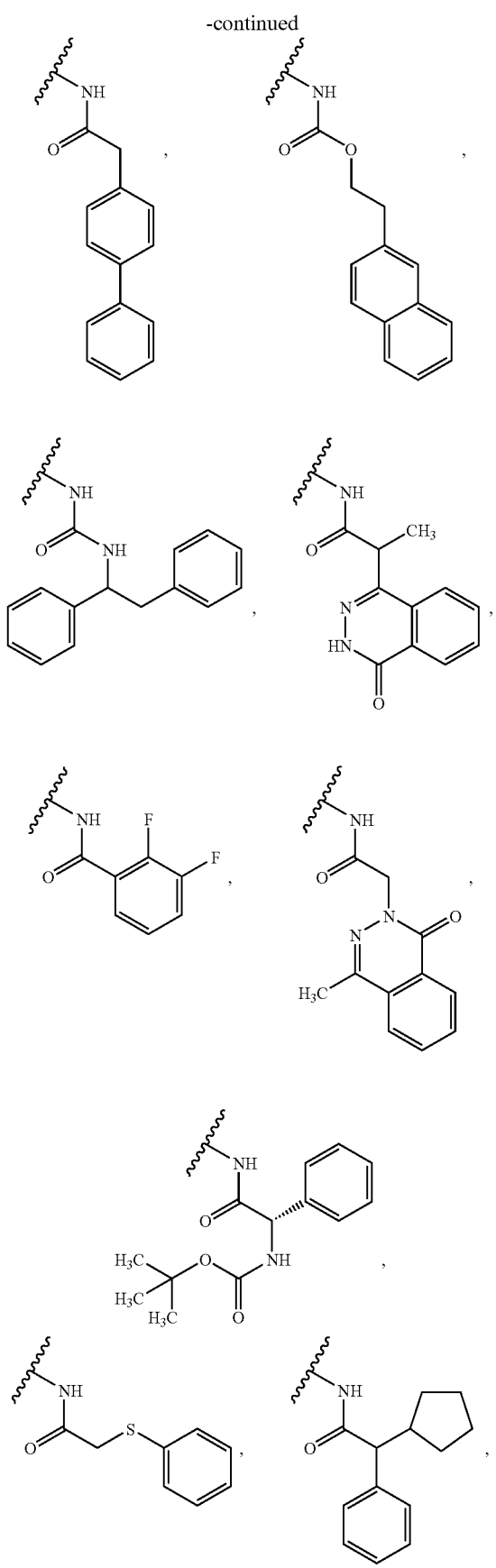
200
-continued
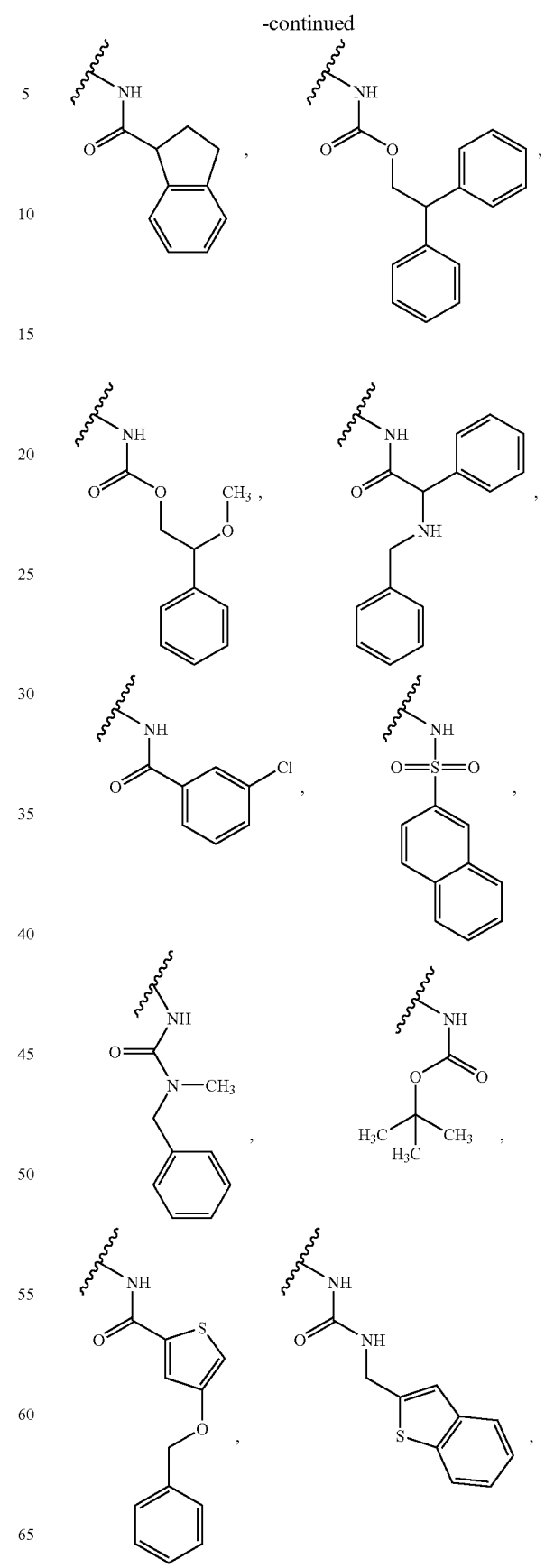

201
-continued
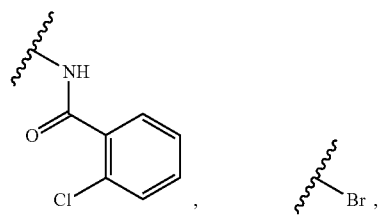
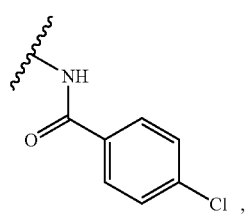
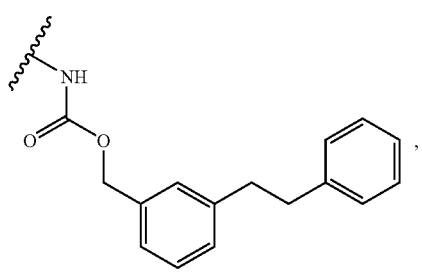
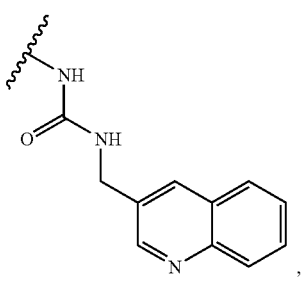
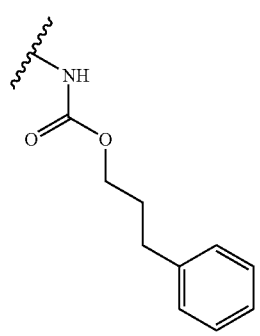
202
-continued
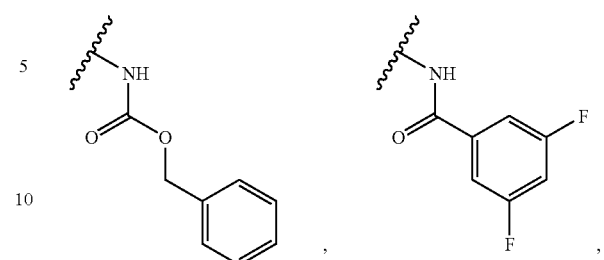
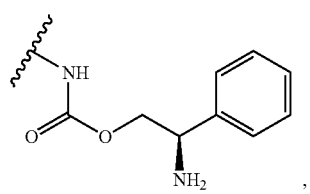
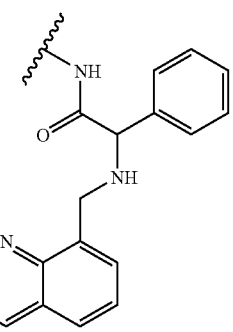
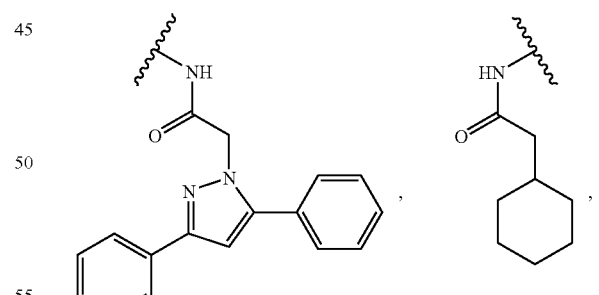
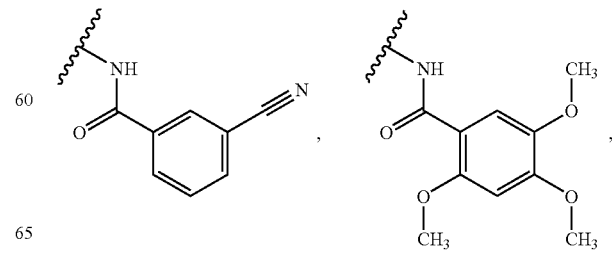

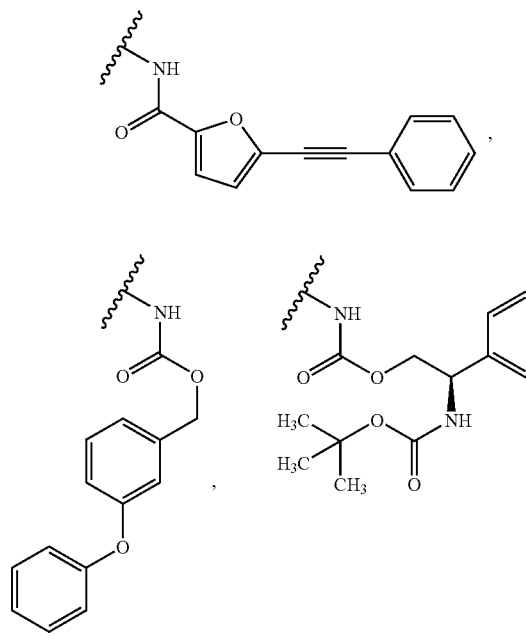
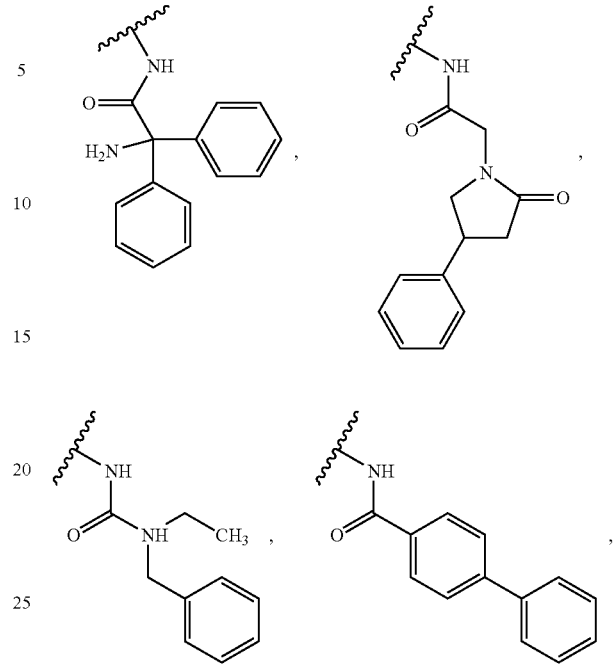
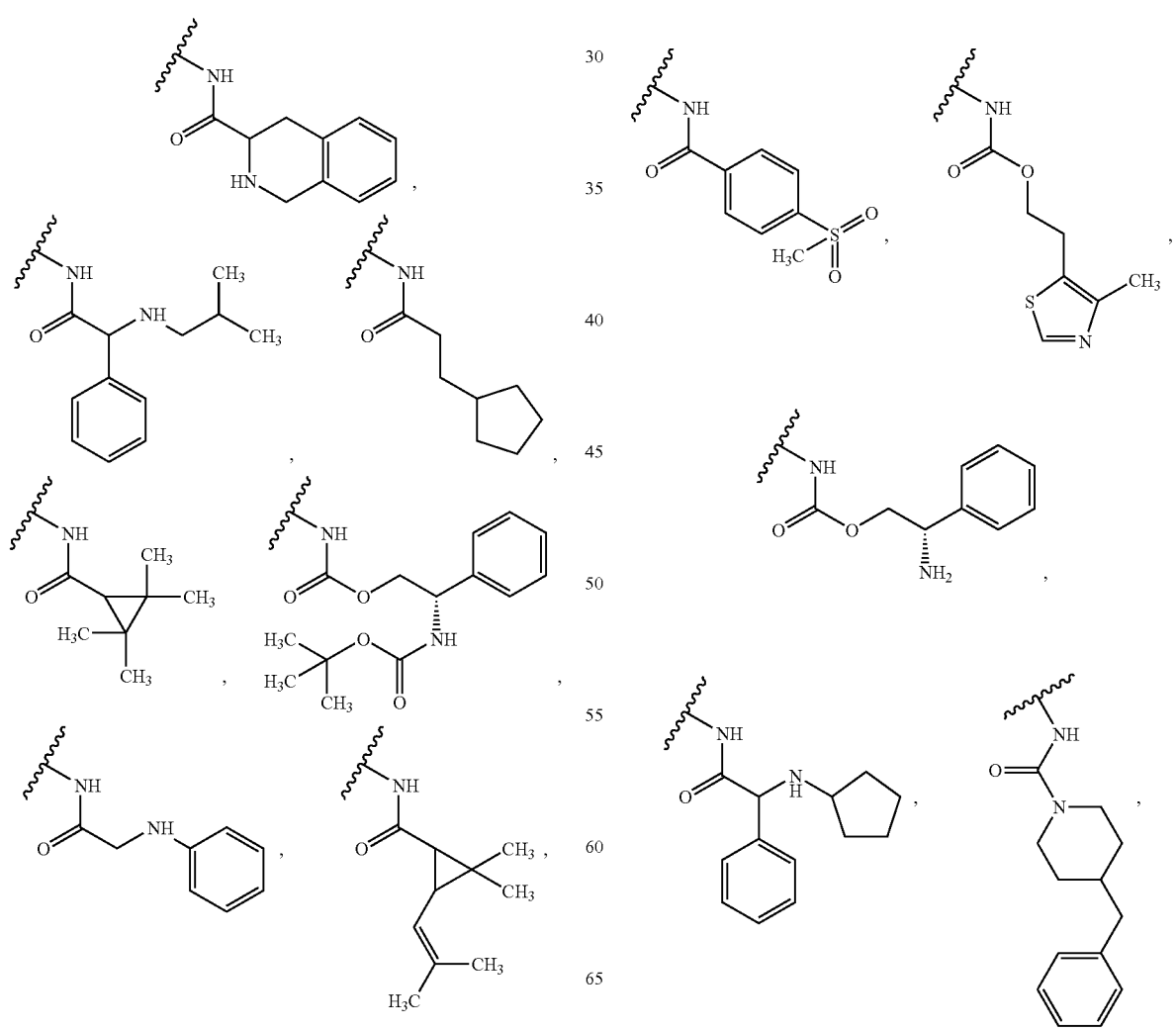

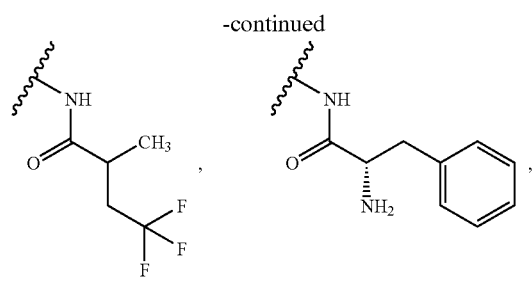
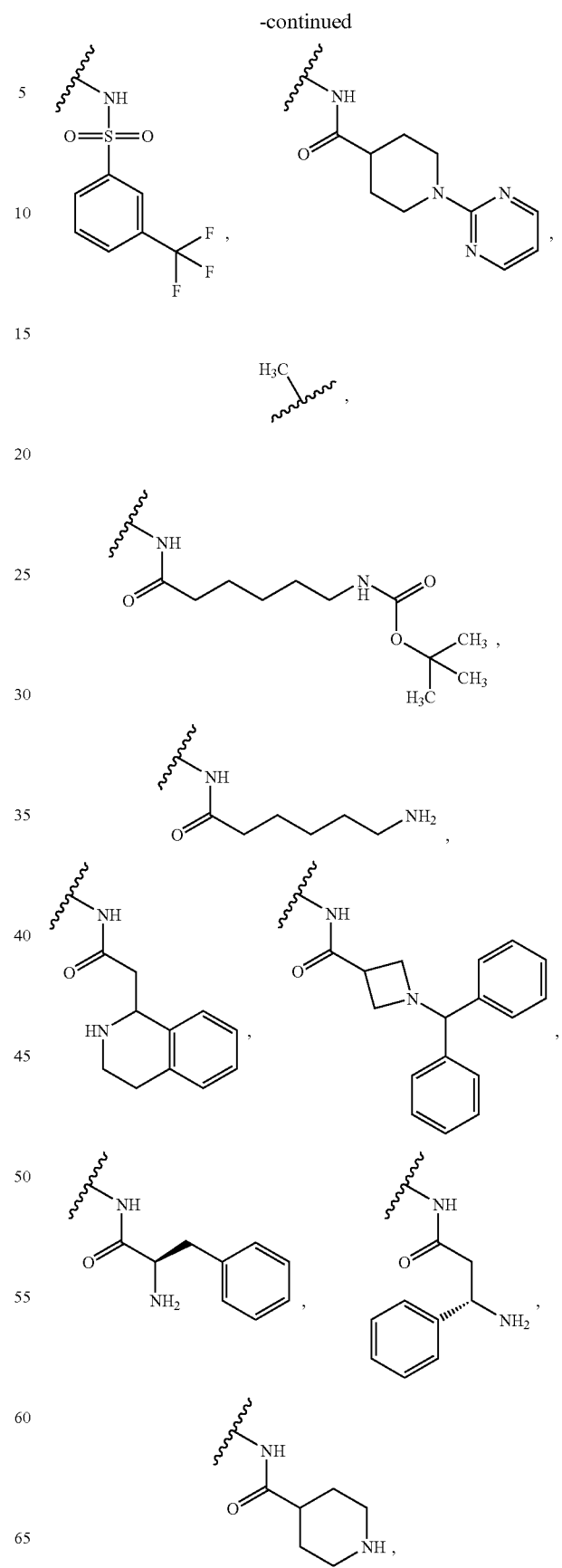

-continued
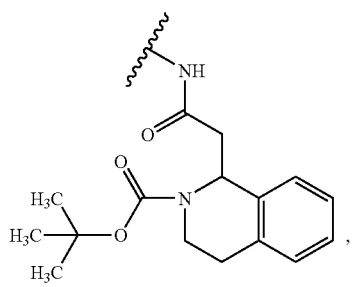
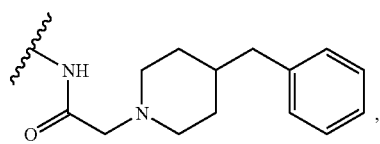
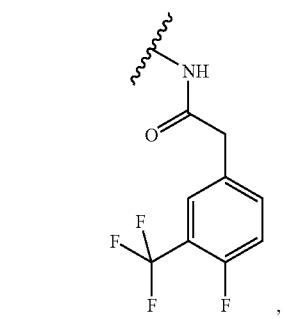
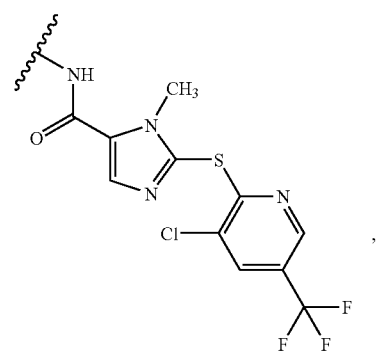
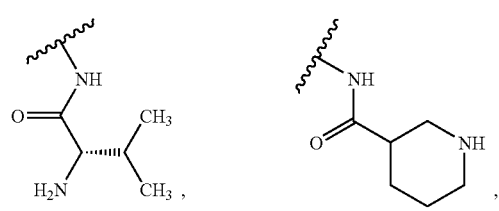
-continued
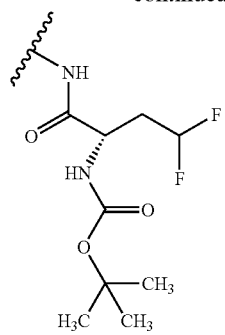
and
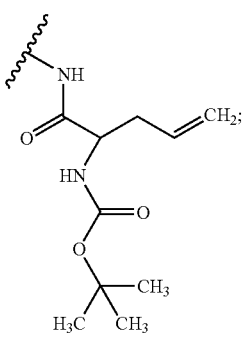
F)
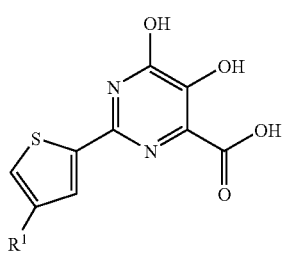
wherein R¹ is selected from the, group consisting of:
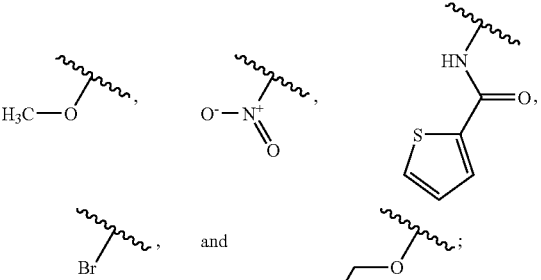
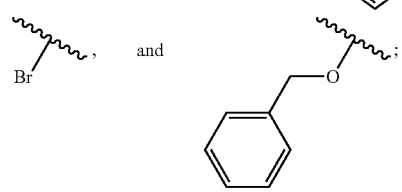

wherein R¹ is selected from the group consisting of:

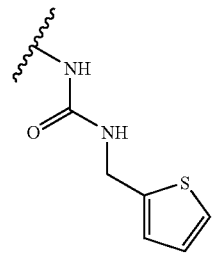 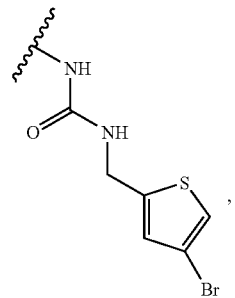 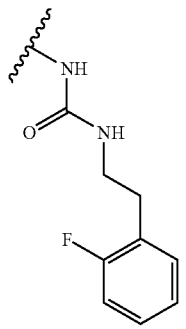 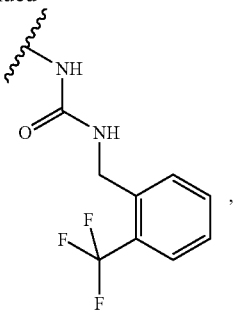
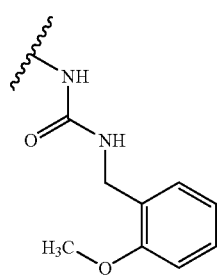 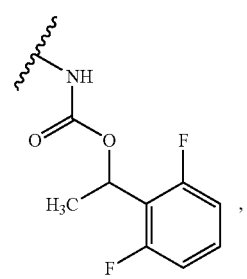 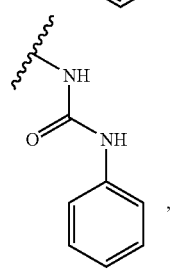 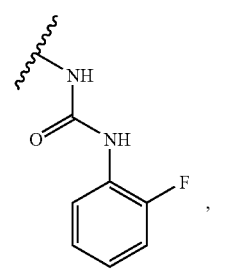
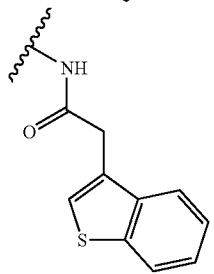
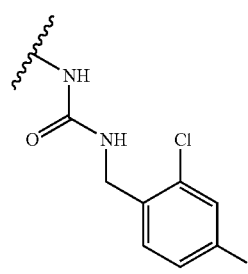 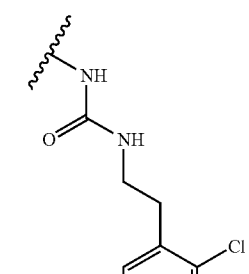 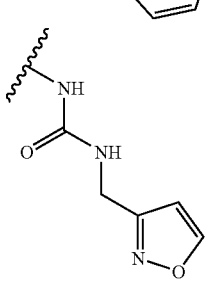 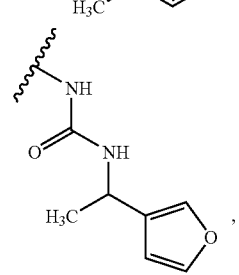
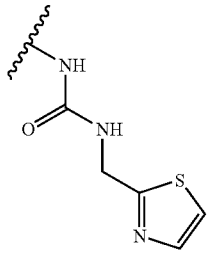 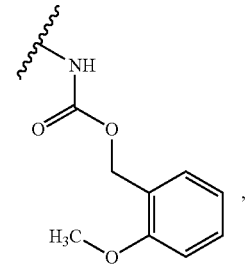 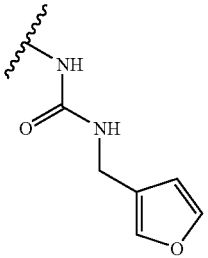 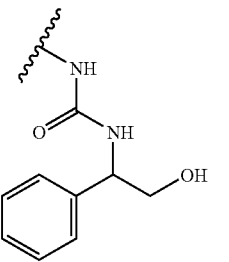
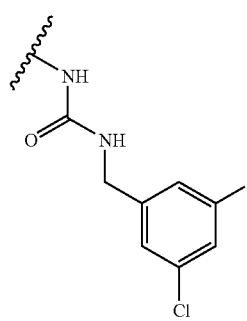 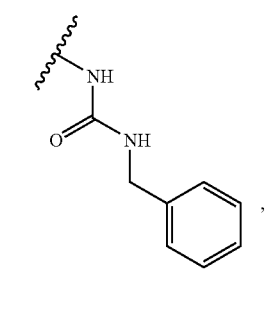 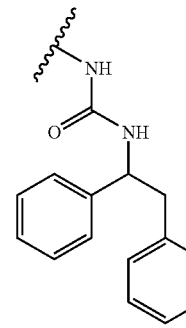 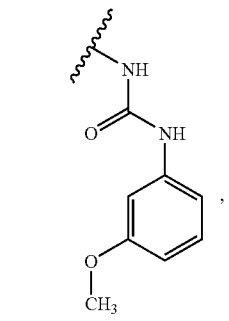

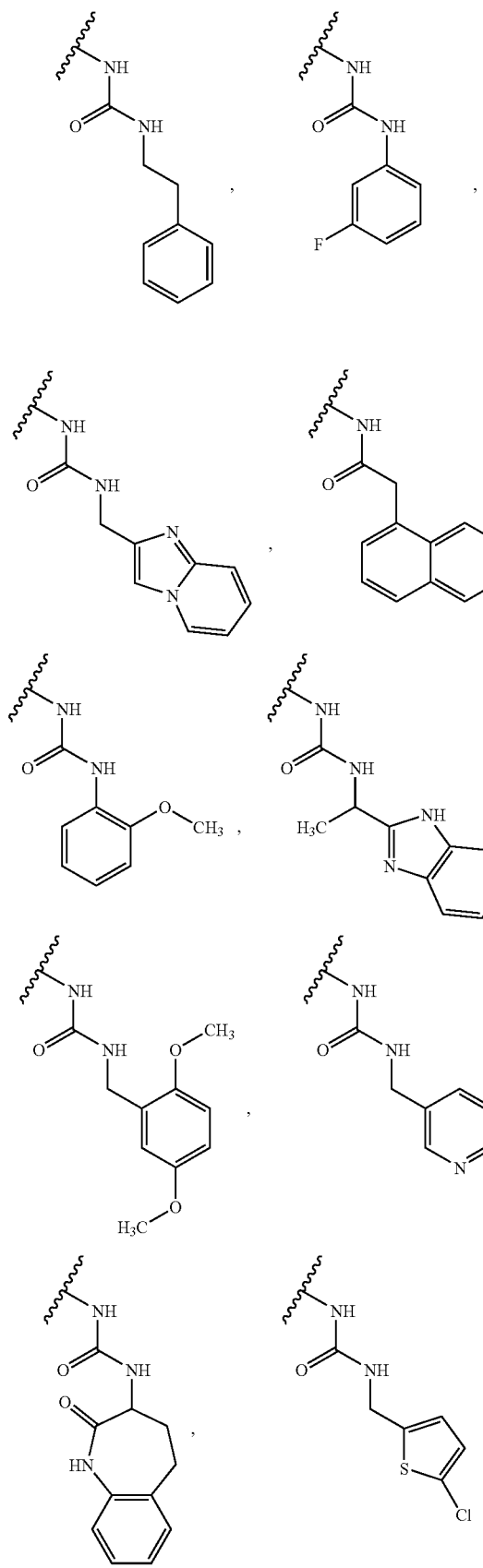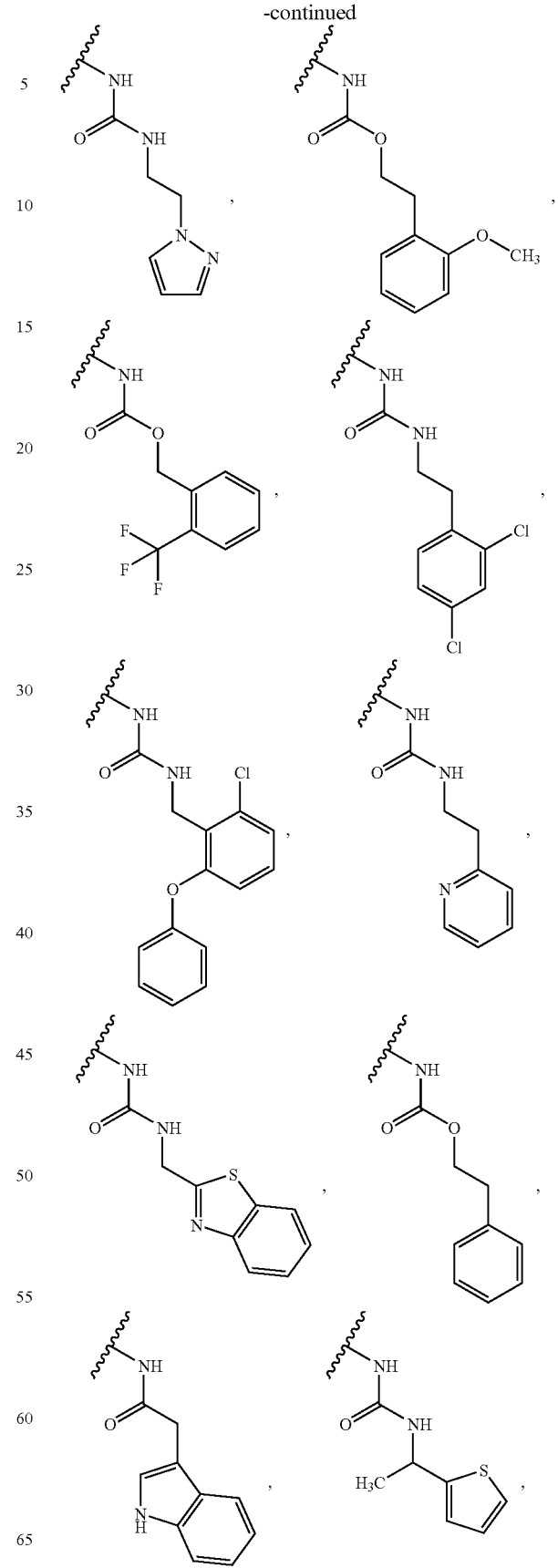

-continued
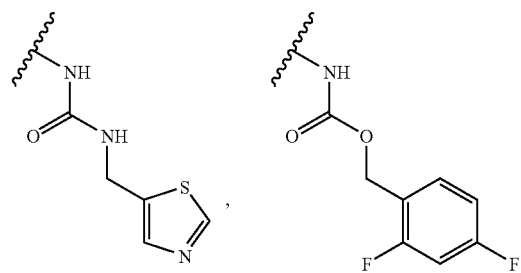
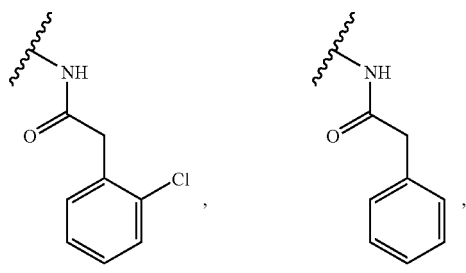
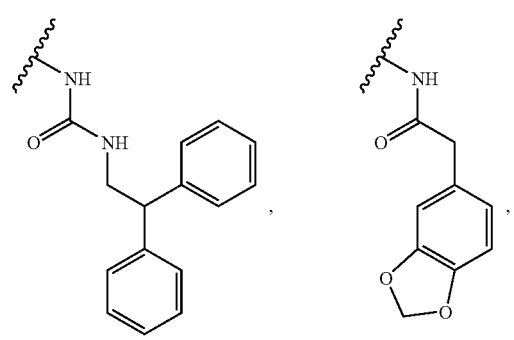
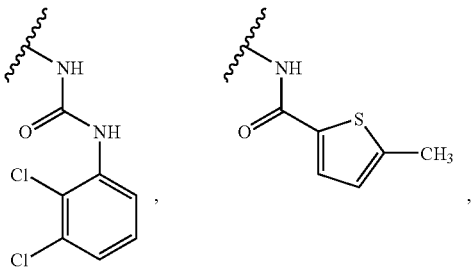
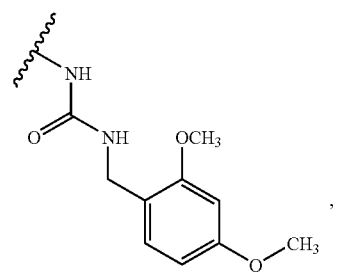
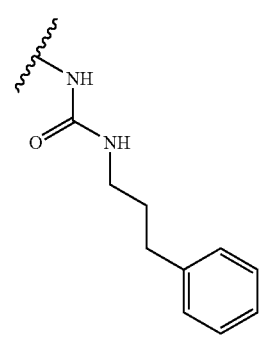
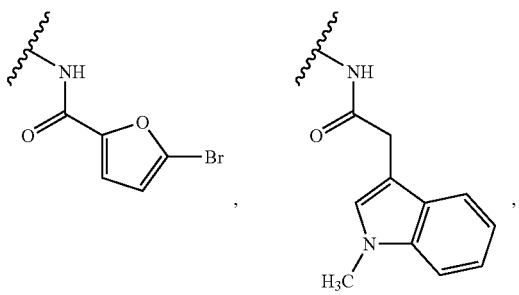
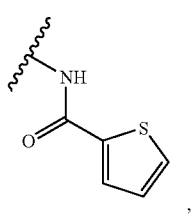
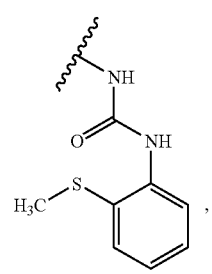
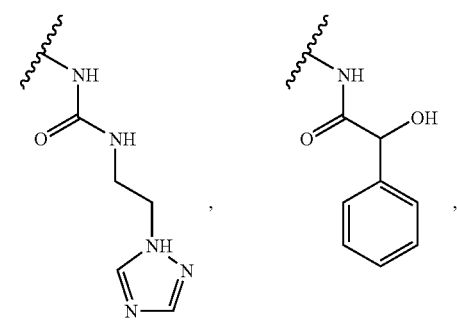
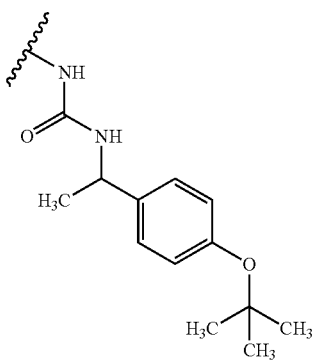

-continued
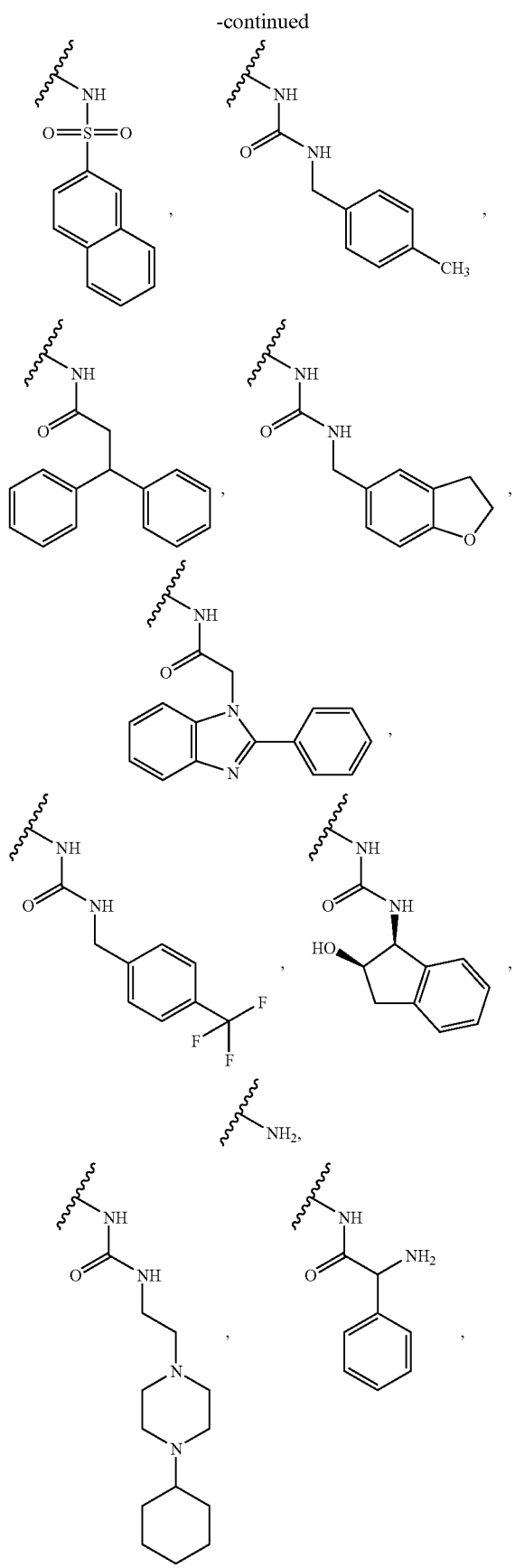
-continued
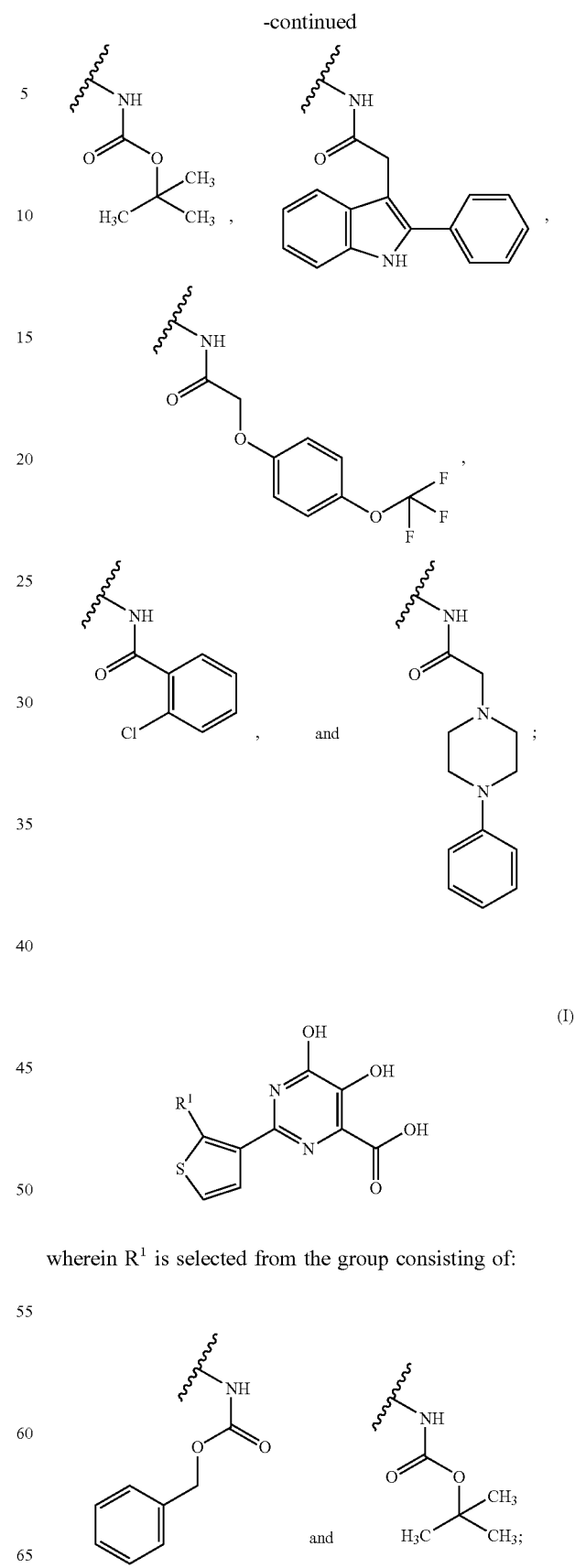
wherein R[1] is selected from the group consisting of:

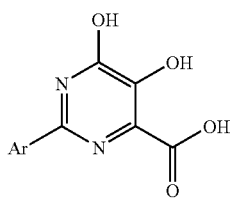
(J)
wherein Ar is:
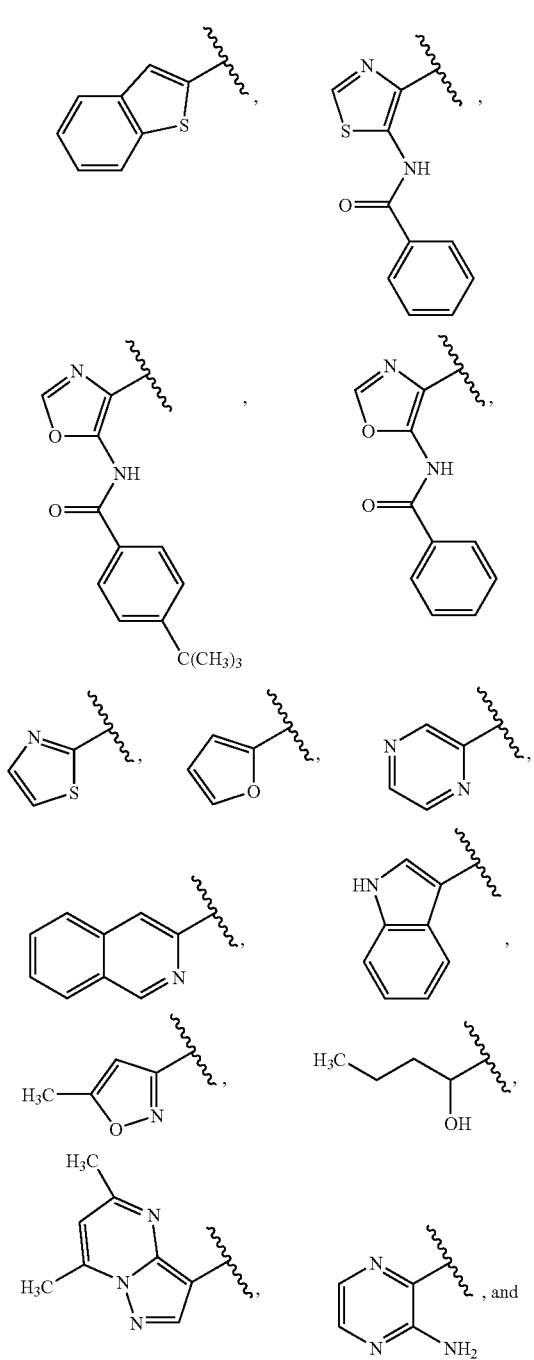
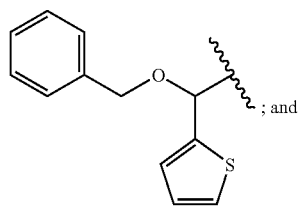; and
(K) a compound selected from the group consisting of:
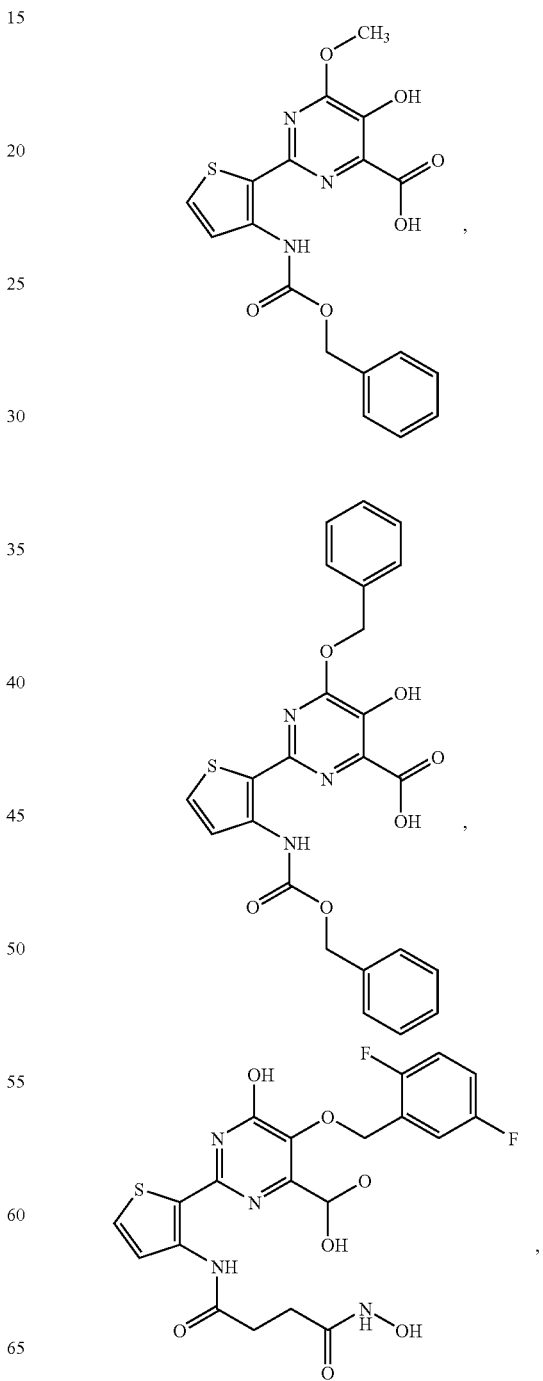

-continued
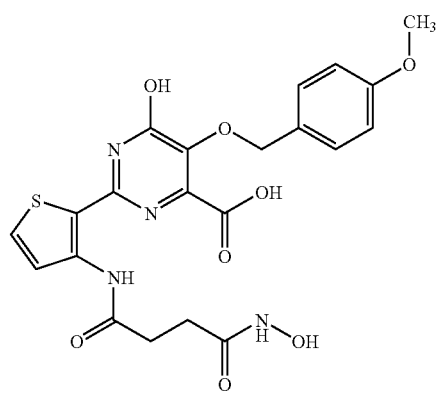
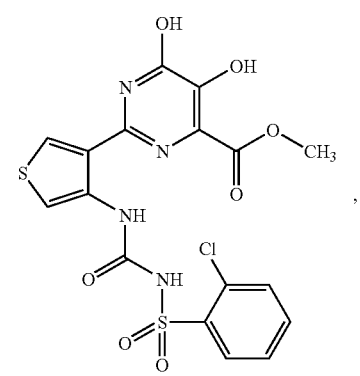
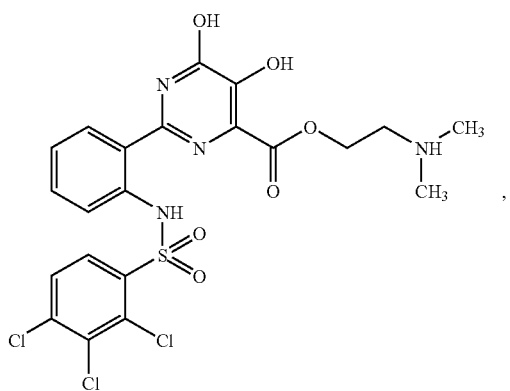
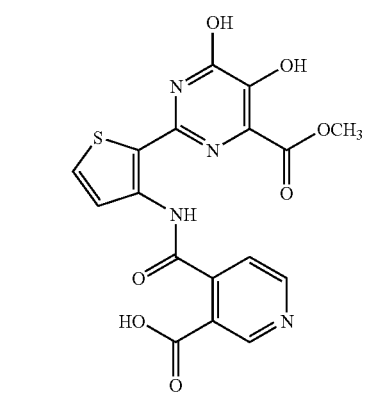
and
-continued
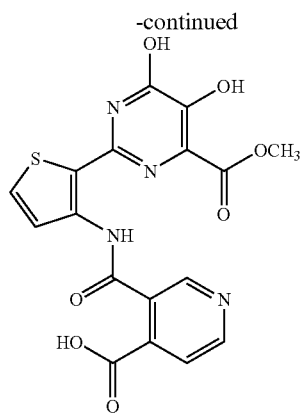
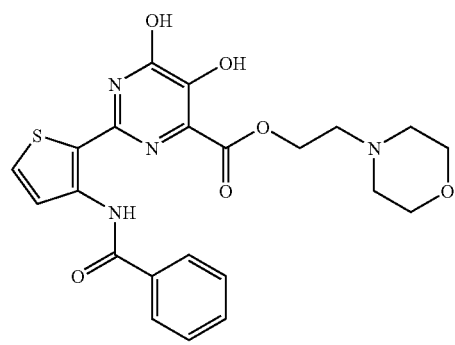
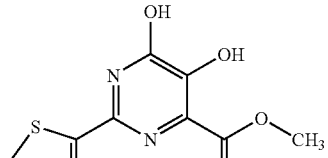
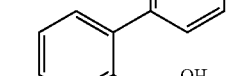
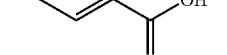
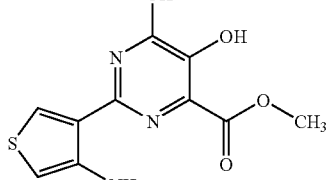
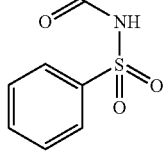
, 223
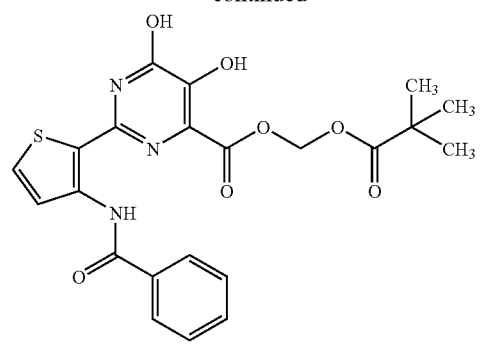
,
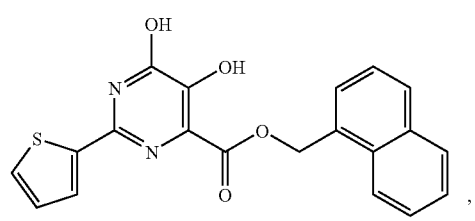
,
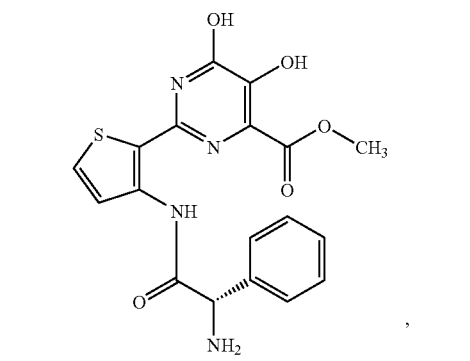
,
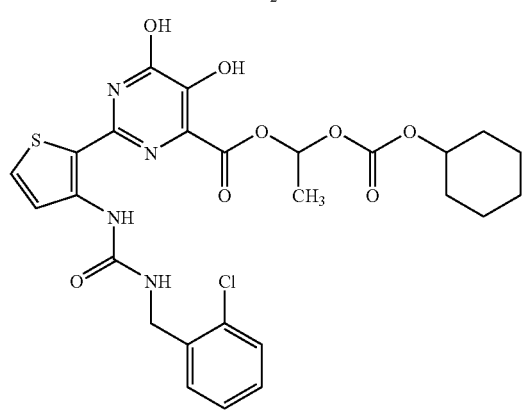
,
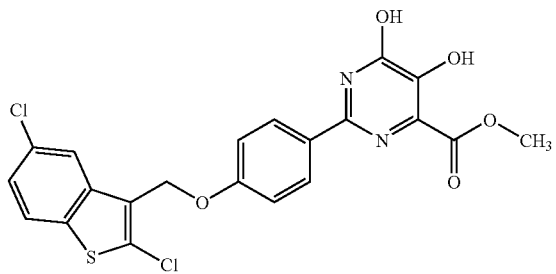
,
224
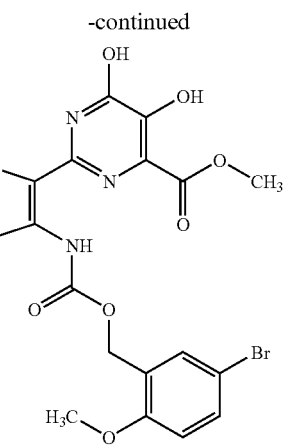
,
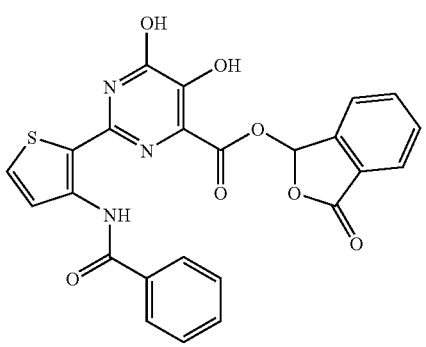
,
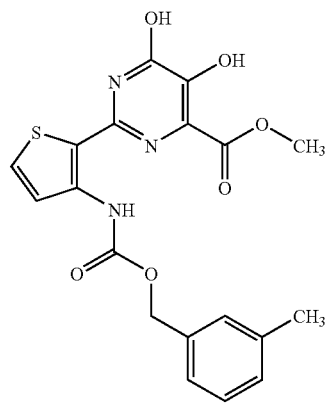
,
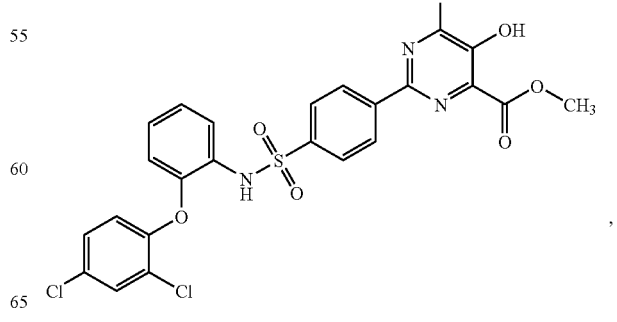

-continued
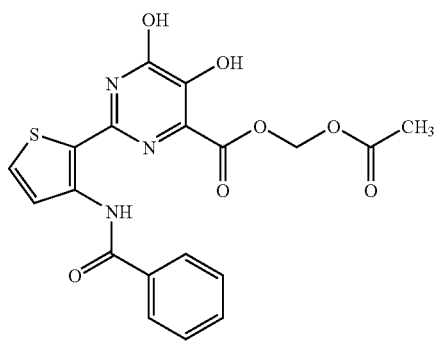
, and
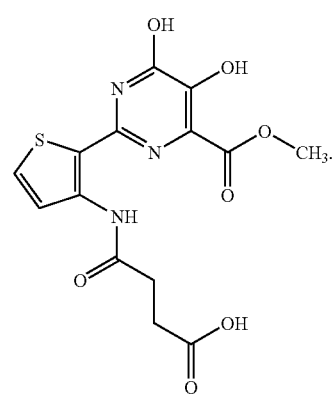
16. A compound, or a tautomer thereof, or a pharmaceutically acceptable salt or ester thereof, selected from the group consisting of:
(A)
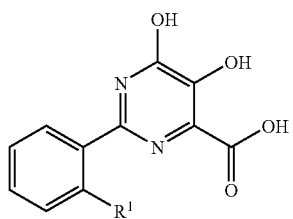
wherein R¹ is selected from the group consisting of:
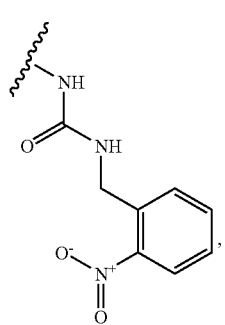
,
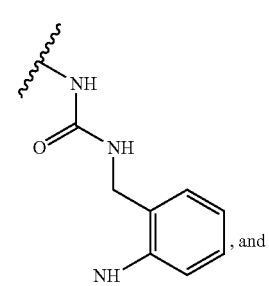
, and
-continued
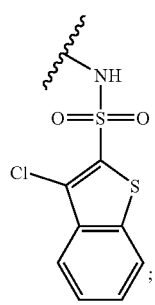
;
(B)
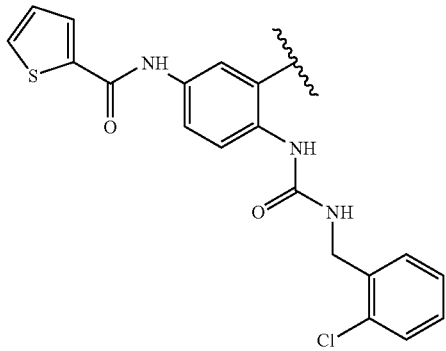
(C)
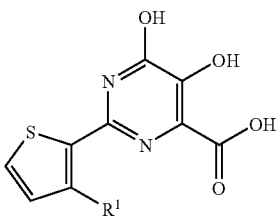
wherein R¹ is selected from the group consisting of:
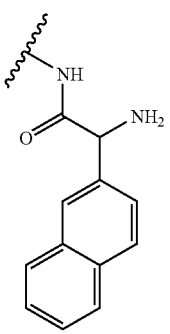
,
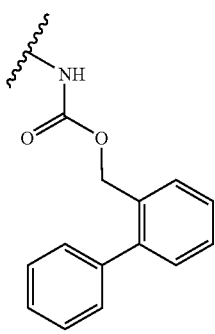
,

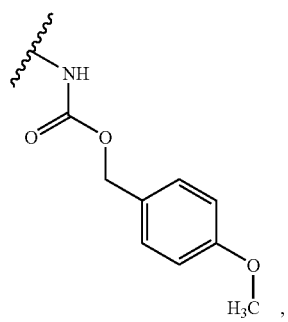
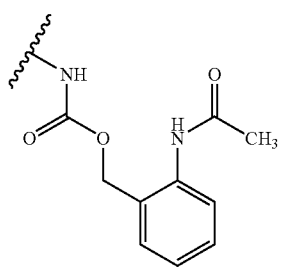
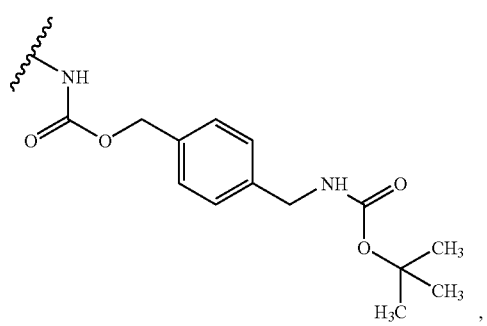
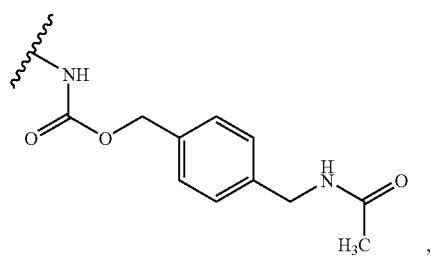
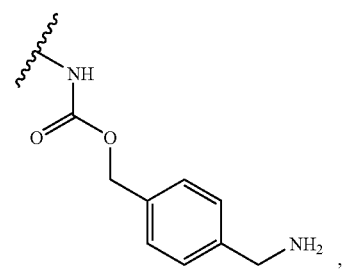
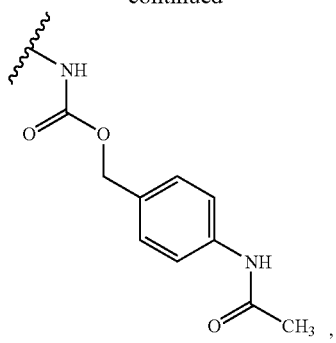
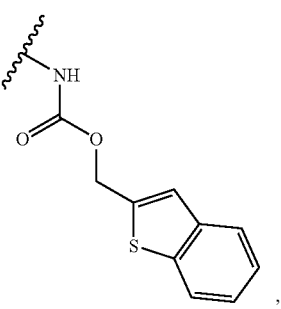
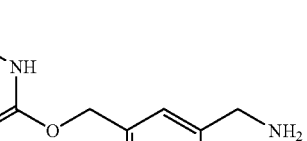
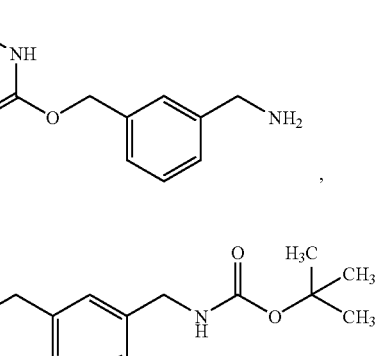
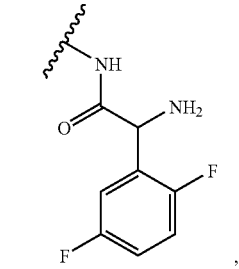
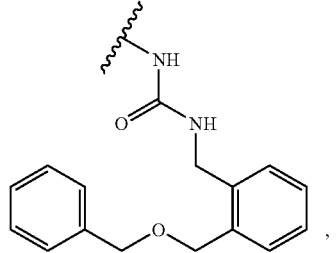

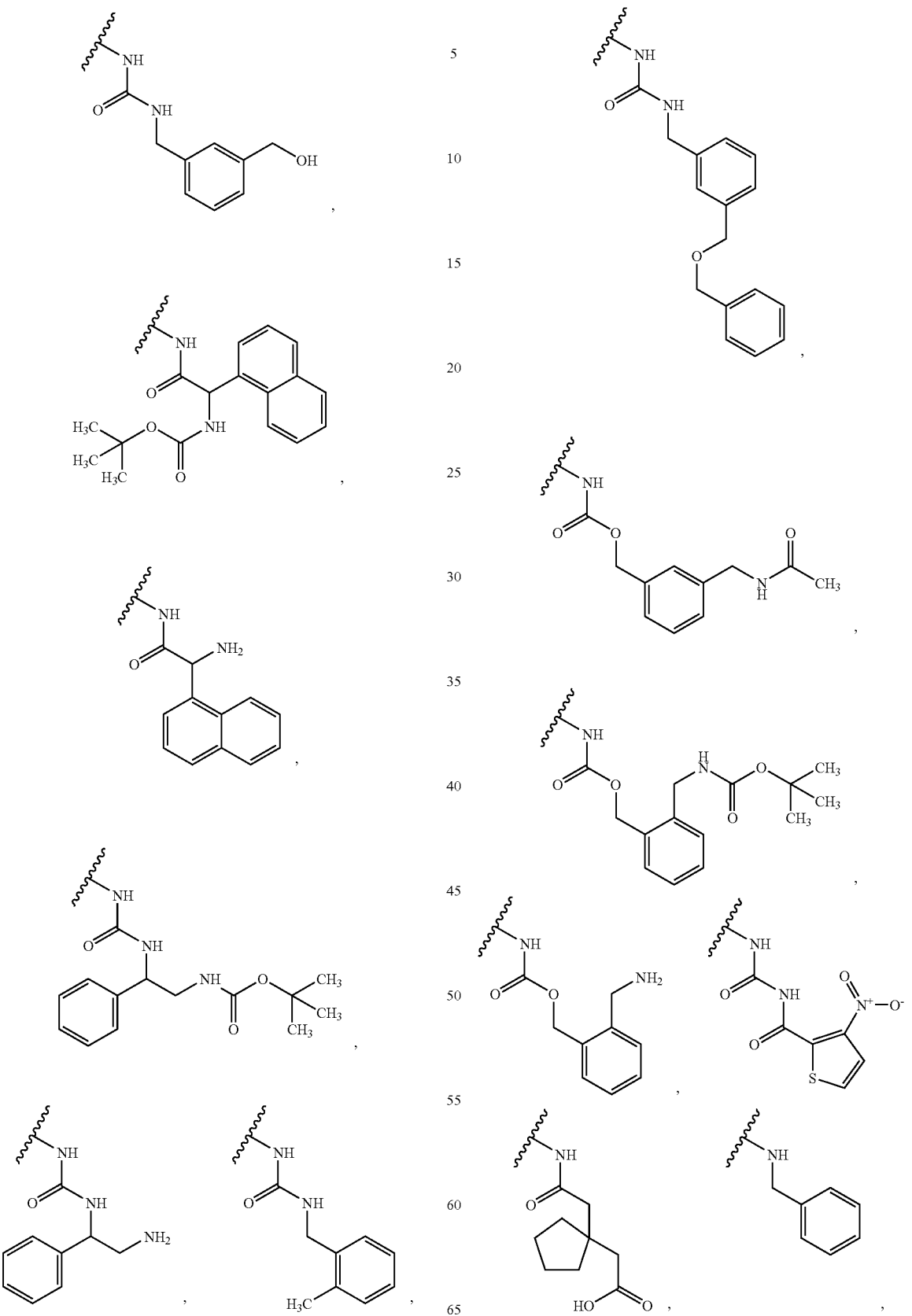

-continued
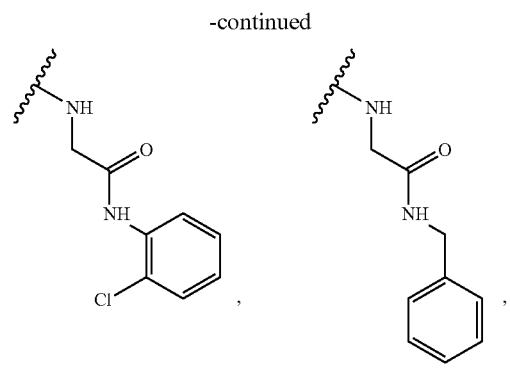
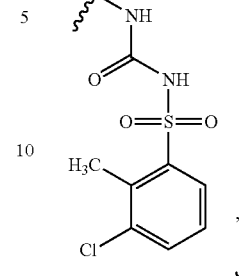
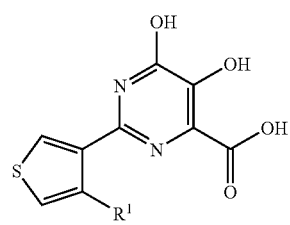
;
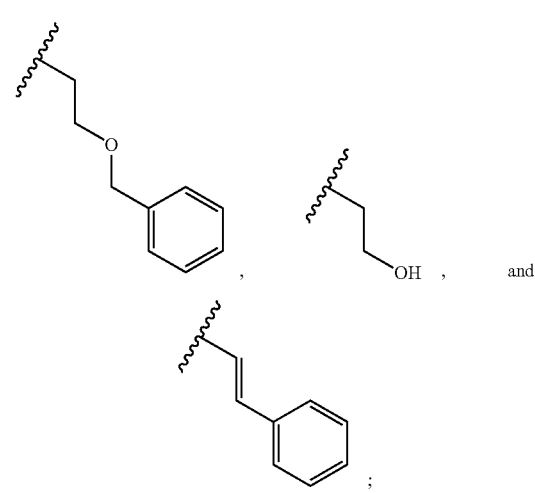
wherein $R_1$ is selected from the group consisting of:
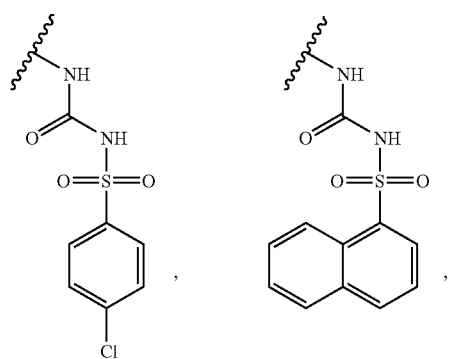
-continued
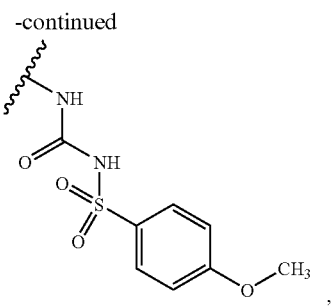
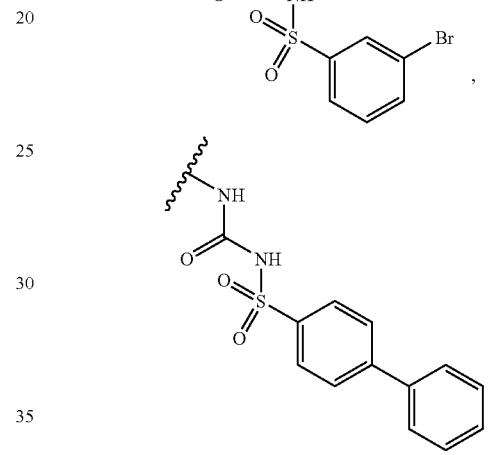
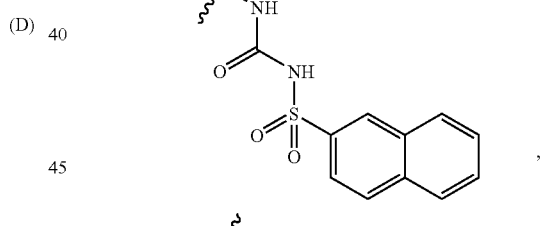
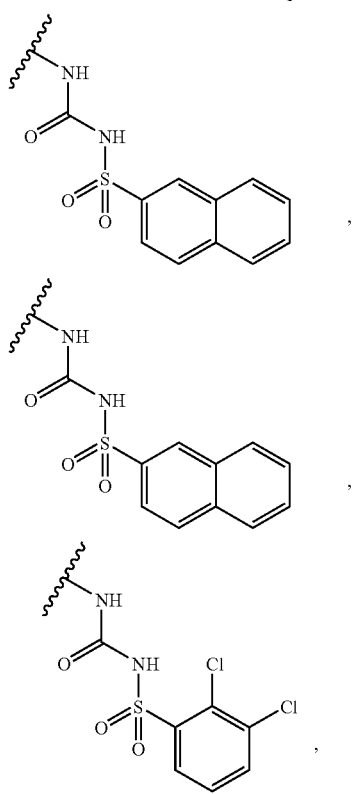

-continued
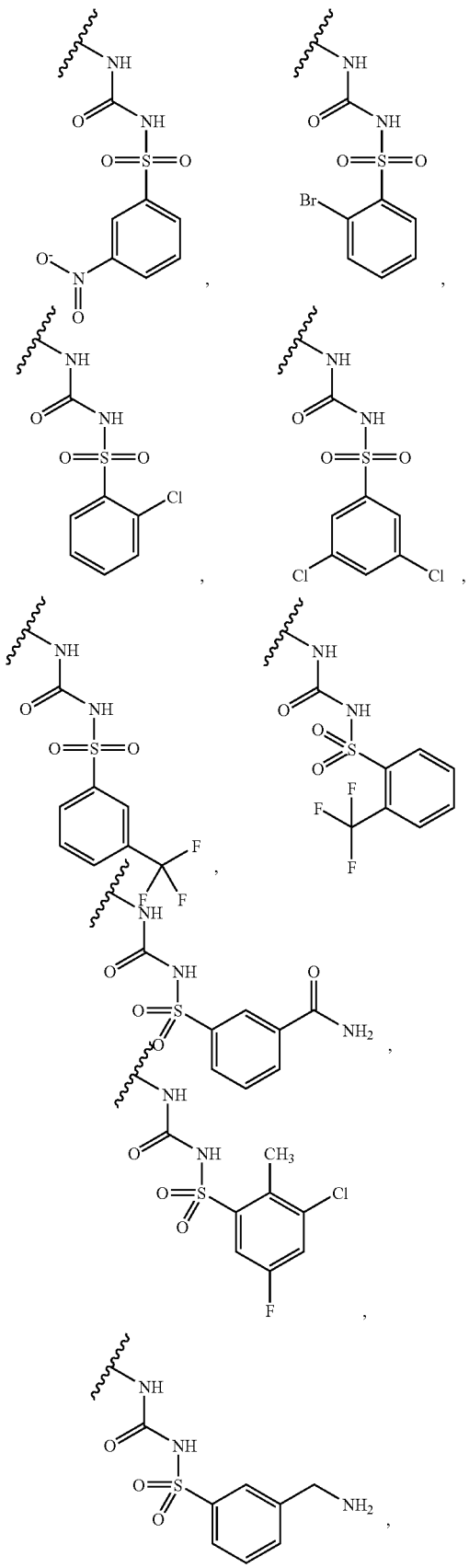
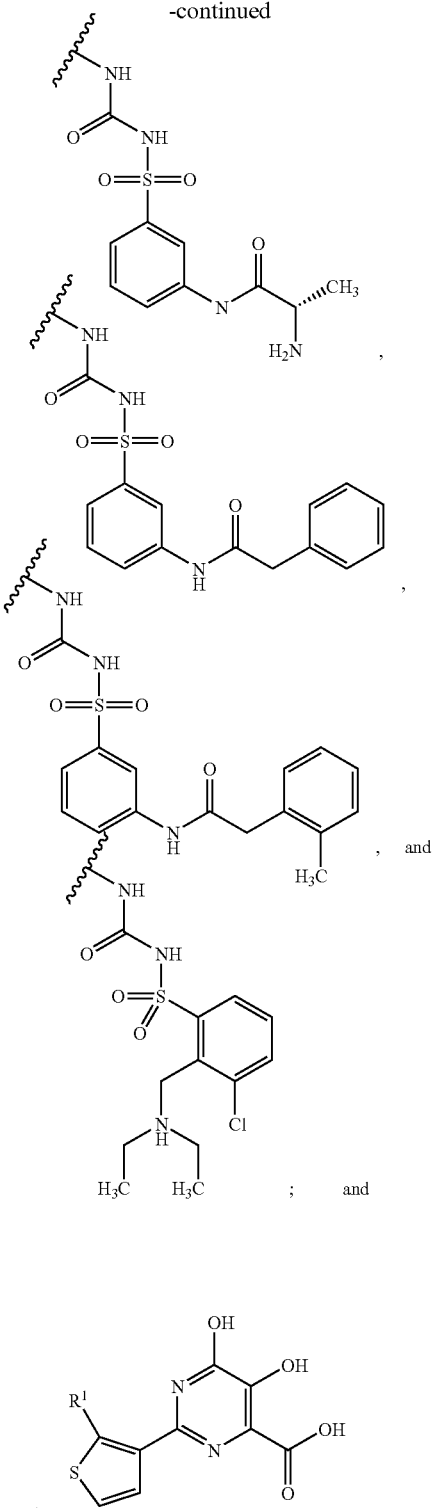
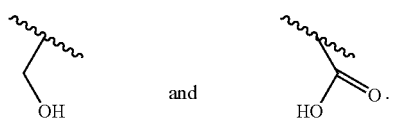
* * * * *

UNITED STATES PATENT AND TRADEMARK OFFICE
CERTIFICATE OF CORRECTION

| | | |
|---|---|---|
| PATENT NO. | : 7,091,209 B2 | Page 1 of 1 |
| APPLICATION NO. | : 10/333431 | |
| DATED | : August 15, 2006 | |
| INVENTOR(S) | : Cristina Gardelli et al. | |

It is certified that error appears in the above-identified patent and that said Letters Patent is hereby corrected as shown below:

On the cover page of the patent, item "(73) Assignee",
        Delete "Merck & Co., Inc., Rahway, NJ"
        and Insert therefor
        --Istituto di Ricerche di Biologia Molecolare P. Angeletti S.P.A., Pomezia (Rome), Italy--.

Signed and Sealed this
Fifth Day of April, 2011

David J. Kappos
*Director of the United States Patent and Trademark Office*